US007205296B2

(12) United States Patent  
Scarborough et al.

(10) Patent No.: US 7,205,296 B2
(45) Date of Patent: Apr. 17, 2007

(54) SUBSTITUTED 2H-1,3-BENZOXAZIN-4(3H)-ONES

(75) Inventors: Robert M. Scarborough, Half Moon Bay, CA (US); Meenakshi S. Venkatraman, Foster City, CA (US); Xiaoming Zhang, Sunnyvale, CA (US); Anjali Pandey, Fremont, CA (US)

(73) Assignee: Portola Pharmaceuticals, Inc., So. San Francisco, CA (US)

( * ) Notice: Subject to any disclaimer, the term of this patent is extended or adjusted under 35 U.S.C. 154(b) by 0 days.

(21) Appl. No.: 11/236,051

(22) Filed: Sep. 26, 2005

(65) Prior Publication Data

US 2006/0069093 A1 Mar. 30, 2006

Related U.S. Application Data

(60) Provisional application No. 60/614,564, filed on Sep. 29, 2004.

(51) Int. Cl.
C07D 409/12 (2006.01)
C07D 409/14 (2006.01)
A61K 31/538 (2006.01)

(52) U.S. Cl. .................. 514/230.5; 544/71; 544/92
(58) Field of Classification Search ............... 544/71, 544/92; 514/230.5
See application file for complete search history.

(56) References Cited

U.S. PATENT DOCUMENTS

| | | | |
|---|---|---|---|
| 5,288,726 A | 2/1994 | Koike et al. | |
| 6,248,729 B1 | 6/2001 | Coniglio et al. | |
| 6,509,348 B1 | 1/2003 | Ogletree | |
| 6,689,786 B2 | 2/2004 | Scarborough et al. | |
| 6,995,156 B2 | 2/2006 | Bryant et al. | |
| 2003/0109543 A1 | 6/2003 | Ogletree | |
| 2003/0124626 A1 | 7/2003 | Takasaki et al. | |

FOREIGN PATENT DOCUMENTS

| | | |
|---|---|---|
| WO | WO 99/05144 A1 | 2/1999 |
| WO | WO 99/36425 A1 | 7/1999 |
| WO | WO 098856 A2 | 12/2002 |

OTHER PUBLICATIONS

André, P. et al., "Anticoagulants (Thrombin Inhibitors) and Aspirin Synergize With $P2Y_{12}$ Receptor Antagonism in Thrombosis," *Circulation* (Nov. 25, 2003), pp. 2697-2703.
André, P. et al., "$P2Y_{12}$ Regulates Platelet Adhesion/Activation, Thrombus Growth, and Thrombus Stability in Injured Arteries," *J. Clinical Investigation* (Aug. 2003), vol. 112:3.
Berge, S. M. et al., "Pharmaceutical Salts," *J. Pharm. Sciences* (Jan. 1977), vol. 66:1.
Dorsam, R.T. et al., "Central Role of the $P2Y_{12}$ Receptor in Platelet Activation," *J. Clinical Investigation* (Feb. 2004), vol. 113:3.
Fox, K.A.A. et al., "Benefits and Risks of the Combination of Clopidogrel and Aspirin in Patients Undergoing Surgical Revascularization for Non-ST-Elevation Acute Coronary Syndrome," *Circulation* (Sep. 7, 2004), pp. 1202-1208.
Fratantoni, J. C. et al., "Measuring Platelet Aggregation with Microplate Reader—A new Technical Approach to Platelet Aggregation Studies," *Platelet Aggregation with Microplates*, (1989) vol. 94:5, pp. 613-617.
Fredholm, B. B. et al., "Towards a Revised Nomenclature for P1 and P2 Receptors," *TiPS* (Mar. 1997), vol. 18, pp. 79-82.
Gent, M. et al., "A Randomised, Blinded, Trial of Clopidogrel Versus Aspirin in Patients at Risk of Ischaemic Events (CAPRIE)," *The Lancet* (Nov. 16, 1996), vol. 348, pp. 1329-1339.
Hechler, B. et al., "The $P2Y_1$ Receptor is Necessary for Adenosine 5'-Diphosphate-Induced Platelet Aggregation," *Blood* (Jul. 1, 1998), vol. 92:1, pp. 152-159.
Hollopeter, G. et al., Identification of the Platelet ADP Receptor Targeted by Antithrombotic Drugs, *Nature* (Jan. 11, 2001), vol. 409, pp. 202-207.
Humphries, R. G. et al., A Novel Series of $P_{2T}$ Purinoceptor Antagonists: Definition of the Role of ADP in Arterial Thrombosis, *TiPS* (Jun. 1995), vol. 16, pp. 179-181.
Ingall, A. H. et al., Antagonists of the Platelet $P_{2T}$ Receptor: A Novel Approach to Antithrombotic Therapy, *J. Med. Chem.* (1999), vol. 42, pp. 213-220.
Jantzen, H. et al., "Evidence for Two Distinct G-Protein-Coupled ADP Receptors Mediating Platelet Activation," *Throm Haemost* (1999), vol. 81, pp. 111-117.
King, B. F. et al., "Metabotropic Receptors for ATP and UTP: Exploring the Correspondence Between Native and Recombinant Nucleotide Receptors," *TiPS* (Dec. 1998), vol. 19, pp. 506-514.
Kunapuli, S.P. et al., "$P_2$ Receptor Subtypes in the Cardiovascular System," *Biochem. J.* (1998), vol. 336, pp. 513-523.
Kunapuli, S.P., Multiple P2 Receptor Subtypes on Platelets: A New Interpretation of Their Function, *TiPS* (Oct. 1998), vol. 19, pp. 391-394.
Mehta, S. R. et al., "Effects of Pretreatment with Clopidogrel and Aspirin Followed by Long-Term Therapy in Patients Undergoing Percutaneous Coronary Intervention: The PCI-CURE Study," *The Lancet* (Aug. 18, 2001), vol. 358, pp. 527-533.
Mills, D. C. B., "ADP Receptors on Platelets," *Thrombosis and Haemostasis* (1996), vol. 76:6, pp. 835-856.
Quinn, M. J. et al., "Ticlopidine and Clopidogrel," *Circulation* (1999); vol. 100, pp. 1667-1672.

(Continued)

*Primary Examiner*—Kahsay Habte
(74) *Attorney, Agent, or Firm*—Townsend and Townsend and Crew LLP

(57) ABSTRACT

Substituted benzoxazin-4(3H)-ones are provided which are useful for treating thrombosis and for reducing the likelihood and/or severity of a secondary ischemic event in a patient.

27 Claims, No Drawings

OTHER PUBLICATIONS van Gestel, M.A. et al., "In Vivo Blockade of Platelet ADP Receptor $P2Y_{12}$ Reduces Embolus and Thrombus Formation but Not Thrombus Stability," *Arterioscler Thromb Vasc Biol.* (2003), vol. 23, pp. 518-523.

Wiviott, S. D. et al., Randomized Comparison of Prasugrel (CS-747, LY640315), a Novel Thienopyridine $P2Y_{12}$ Antagonist, with Clopidogrel in Percutaneous Coronary Intervention: Results of the Joint Utilization of Medications to Block Platelets Optimally (JUMBO)-TIMI 26 Trial, *Circulation* (2005), vol. 111, pp. 3366-3373.

Yusuf, S. et al., "Effects of Clopidogrel in Addition to Aspirin in Patients with Acute Coronary Syndromes Without ST-Segment Elevation: The Clopidogrel in Unstable Angina to Prevent Recurrent Events Trial Investigators," *N Engl J. Med* (Aug. 16, 2001), vol. 345:7, pp. 494-502.

SUBSTITUTED 2H-1,3-BENZOXAZIN-4(3H)-ONES

CROSS-REFERENCES TO RELATED APPLICATIONS

This application claims the benefit of U.S. Provisional Application Ser. No. 60/614,564 filed Sep. 29, 2004, the content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and protheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) *Thromb. Hemost.* 76:835–856). Therefore, platelet ADP receptors are members of the family of P2 receptors activated by purine and/or pyrimidine nucleotides (King, B. F., Townsend-Nicholson, A. & Burnstock, G. (1998) *Trends Pharmacol. Sci.* 19:506–514).

Recent pharmacological data using selective antagonists suggests that ADP-dependent platelet aggregation requires activation of at least two ADP receptors (Kunapuli, S. P. (1998), *Trends Pharmacol. Sci.* 19:391–394; Kunapuli, S. P. & Daniel, J. L. (1998) *Biochem. J.* 336:513–523; Jantzen, H. M. et al. (1999) *Thromb. Hemost.* 81:111–117). One receptor appears to be identical to the cloned P2Y$_1$ receptor, mediates phospholipase C activation and intracellular calcium mobilization and is required for platelet shape change. The second platelet ADP receptor important for aggregation mediates inhibition of adenylyl cyclase. Molecular cloning of the gene or cDNA for this receptor (P2Y$_{12}$) has recently been reported (Hollopeter, G. et. al. (2001) *Nature* 409: 202–207). Based on its pharmacological and signaling properties this receptor has been previously termed P2Y$_{ADP}$ (Fredholm, B. B. et al. (1997) *TIPS* 18:79–82), P2T$_{AC}$ (Kunapuli, S. P. (1998), *Trends Pharmacol. Sci.* 19:391–394) or P2Ycyc (Hechler, B. et al. (1998) Blood 92, 152–159).

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unstable and irreversible acting metabolite (Quinn, M. J. & Fitzgerald, D. J. (1999) *Circulation* 100:1667–1667). Some purine derivatives of the endogenous antagonist ATP, e.g., AR-C (formerly FPL or ARL) 67085MX and AR-C69931MX, are selective platelet ADP receptor antagonists which inhibit ADP-dependent platelet aggregation and are effective in animal thrombosis models (Humphries et al. (1995), *Trends Pharmacol. Sci.* 16, 179; Ingall, A. H. et al. (1999) J. Med. Chem. 42, 213–230). Novel triazolo[4,5-d]pyrimidine compounds have been disclosed as P$_{2T}$-antagonists (WO 99/05144). Tricyclic compounds as platelet ADP receptor inhibitors have also been disclosed in WO 99/36425. Piperazine derivatives are described in WO 02/098856. The target of these antithrombotic compounds appears to be the platelet ADP receptor mediating inhibition of adenylyl cyclase or P2Y$_{12}$.

Despite these compounds, there exists a need for more effective platelet ADP receptor inhibitors. In particular, there is a need for platelet ADP receptor inhibitors having antithrombotic activity that are useful in the prevention and/or treatment of cardiovascular diseases, particularly those related to thrombosis.

BRIEF SUMMARY OF THE INVENTION

The present invention provides compounds having the formula:

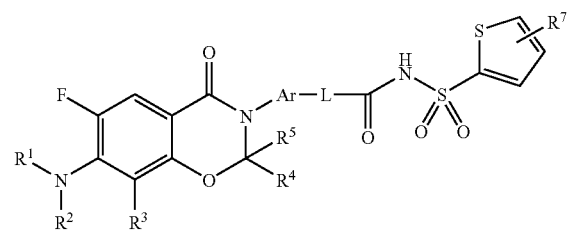

and pharmaceutically acceptable salts thereof, wherein R$^1$ represents a member selected from C$_{1-6}$ alkyl, C$_{1-6}$ haloalkyl, C$_{3-5}$ cycloalkyl, C$_{3-5}$ cycloalkyl-alkyl, benzyl, and substituted benzyl; R$^2$ represents a member selected from H and C$_{1-6}$ alkyl; R$^3$ represents a member selected from H, C$_{1-6}$ alkyl, C$_{2-6}$ alkenyl, C$_{2-6}$ alkynyl, C$_{3-5}$ cycloalkyl, C$_{3-5}$ cycloalkyl-alkyl, C$_{1-6}$ haloalkyl, C$_{1-6}$ hydroxyalkyl, halogen, cyano and —C(O)R$^{3a}$, wherein R$^{3a}$ is a member selected from H, hydroxy, C$_{1-6}$ alkyl, C$_{1-6}$ alkoxy, amino, C$_{1-6}$ alkylamino and di-C$_{1-6}$ alkylamino; R$^4$ represents a member selected from H and C$_{1-6}$ alkyl; R$^5$ represents a member selected from H, C$_{1-6}$ alkyl, C$_{1-6}$ haloalkyl, benzyl, aryl, C$_{1-6}$ alkylene-N—(R$^{5a}$)$_2$; C$_{1-6}$ alkylene-O—(R$^{5a}$); wherein each R$^{5a}$ is a member independently selected from H and C$_{1-6}$ alkyl, and optionally, two R$^{5a}$ groups attached to nitrogen are combined with the nitrogen atom to form an azetidine, pyrrolidine, piperidine or morpholine ring.

The symbol Ar represents an aromatic ring selected from benzene, pyridine, pyrazine and pyrimidine, each of which is optionally substituted with from 1–2 R$^6$ substituents, wherein each R$^6$ is independently selected from halogen, cyano, hydroxy, C$_{1-6}$ alkyl, C$_{2-6}$ alkenyl, C$_{2-6}$ alkynyl, C$_{1-6}$ alkoxy, C$_{1-6}$ haloalkyl, C$_{1-6}$ haloalkoxy, C$_{3-5}$ cycloalkyl-alkoxy, amino, C$_{1-6}$ alkylamino, di-C$_{1-6}$ alkylamino, —C(=NR$^{6a}$)—N(R$^{6b}$)$_2$, —C(O)R$^{6a}$, —O(CH$_2$)$_m$OR$^{6b}$, —(CH$_2$)$_m$OR$^{6b}$, —O(CH$_2$)$_m$N(R$^{6b}$)$_2$ and —(CH$_2$)$_m$N(R$^{6b}$)$_2$, wherein each subscript m is independently an integer of from 1 to 3, each R$^{6a}$ is a member independently selected from H, hydroxy, C$_{1-6}$ alkyl, C$_{1-6}$ alkoxy, amino, C$_{1-6}$ alkylamino and di-C$_{1-6}$ alkylamino, and each R$^{6b}$ is a member independently selected from H, C$_{1-4}$ alkyl and C$_{1-4}$ alkanoyl, and optionally, two R$^{6b}$ groups attached to nitrogen are combined with the nitrogen atom to form an azetidine, pyrrolidine, piperidine or morpholine ring.

The letter L represents a linking group that is a bond or —NH—.

The symbol R$^7$ represents a member selected from H, halogen, cyano, C$_{1-6}$ alkyl, C$_{2-6}$ alkenyl, C$_{2-6}$ alkynyl, C$_{1-6}$ alkoxy and C$_{1-6}$ haloalkyl.

In addition to the compounds provided herein, the present invention further provides pharmaceutical compositions comprising those compounds, as well as methods for the use of the compounds in treating thrombosis as well as preventing the occurrence of a secondary ischemic event.

BRIEF DESCRIPTION OF THE DRAWINGS

Not applicable.

DETAILED DESCRIPTION OF THE INVENTION

Definitions

The term "alkyl", by itself or as part of another substituent, means, unless otherwise stated, a straight or branched chain hydrocarbon radical, having the number of carbon atoms designated (i.e. C$_{1-8}$ means one to eight carbons). Examples of alkyl groups include, but not limit to methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more double bonds directly attached to carbon radicals. Similarly, the term "alkynyl" refers to an unsaturated alkyl group having one or more triple bonds. Examples of such unsaturated alkyl groups include, but not limit to vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., C$_{3-6}$cycloalkyl) and being fully saturated or having no more than one double bond between ring vertices. When "cycloalkyl" is used in combination with "alkyl", as in C$_{3-5}$ cycloalkyl-alkyl, the cycloalkyl portion is meant to have from three to five carbon atoms, while the alkyl portion is an alkylene moiety having from one to three carbon atoms (e.g., —CH$_2$—, —CH$_2$CH$_2$— or —CH$_2$CH$_2$CH$_2$—).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. For brevity, the term C$_{1-6}$alkylamino is meant to include straight chain, branched or cyclic alkyl groups or combinations thereof, such as methyl, ethyl, 2-methylpropyl, cyclobutyl and cyclopropylmethyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Exemplary aryl groups are phenyl, naphthyl, biphenyl and the like. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic ammonium, zinc or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an in vitro environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), phosphorous-32 ($^{32}$P or carbon-14 ($^{14}$C). All isotopic variations of the compounds of the present invention, whether radioactive or not, are intended to be encompassed within the scope of the present invention.

GENERAL DESCRIPTION OF THE EMBODIMENTS COMPOUND

In view of the above, the present invention provides, in one aspect, compounds having the formula:

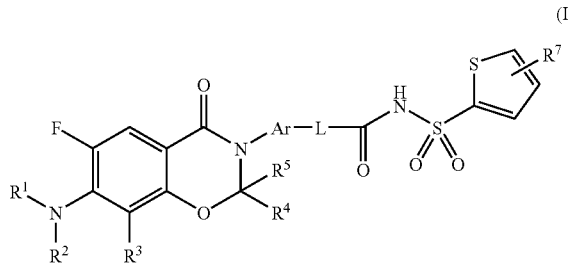

(I)

and pharmaceutically acceptable salts thereof, wherein $R^1$ represents a member selected from $C_{1-6}$ alkyl, $C_{1-6}$ haloalkyl, $C_{3-5}$ cycloalkyl, $C_{3-5}$ cycloalkyl-alkyl, benzyl, and substituted benzyl; $R^2$ represents a member selected from H and $C_{1-6}$ alkyl; $R^3$ represents a member selected from H, $C_{1-6}$ alkyl, $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, halogen, cyano and —C(O)$R^{3a}$, wherein $R^{3a}$ is a member selected from H, hydroxy, $C_{1-6}$ alkyl, $C_{1-6}$ alkoxy, amino, $C_{1-6}$ alkylamino and di-$C_{1-6}$ alkylamino; $R^4$ represents a member selected from H and $C_{1-6}$ alkyl; $R^5$ represents a member selected from H, $C_{1-6}$ alkyl, $C_{1-6}$ haloalkyl, benzyl, aryl, $C_{1-6}$ alkylene-N—($R^{5a}$)$_2$; $C_{1-6}$ alkylene-O—($R^{5a}$); wherein each $R^{5a}$ is a member independently selected from H and $C_{1-6}$ alkyl, and optionally, two $R^{5a}$ groups attached to nitrogen are combined with the nitrogen atom to form an azetidine, pyrrolidine, piperidine or morpholine ring.

The symbol Ar represents an aromatic ring selected from benzene, pyridine, pyrazine and pyrimidine, each of which is optionally substituted with from 1–2 $R^6$ substituents, wherein each $R^6$ is independently selected from halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl-alkoxy, amino, $C_{1-6}$ alkylamino, di-$C_{1-6}$ alkylamino, —C(=NR$^{6a}$)—N(R$^{6b}$)$_2$, —C(O)R$^{6a}$, —O(CH$_2$)$_m$OR$^{6b}$, —(CH$_2$)$_m$OR$^{6b}$, —O(CH$_2$)$_m$N(R$^{6b}$)$_2$ and —(CH$_2$)$_{m\ N(R}$$^{6b}$)$_2$, wherein each subscript m is independently an integer of from 1 to 3, each $R^{6a}$ is a member independently selected from H, hydroxy, $C_{1-6}$ alkyl, $C_{1-6}$ alkoxy, amino, $C_{1-6}$ alkylamino and di-$C_{1-6}$ alkylamino, and each $R^{6b}$ is a member independently selected from H, $C_{1-4}$ alkyl and $C_{1-4}$ alkanoyl, and optionally, two $R^{6b}$ groups attached to nitrogen are combined with the nitrogen atom to form an azetidine, pyrrolidine, piperidine or morpholine ring.

The letter L represent a linking group that is a bond or —NH—.

The symbol $R^7$ represents a member selected from H, halogen, cyano, $C_{1-6}$ alkyl, $C_{2-6}$ alkenyl, $C_{2-6}$ alkynyl, $C_{1-6}$ alkoxy and $C_{1-6}$ haloalkyl.

Certain groups of embodiments are preferred.

In one group of preferred embodiments, the compounds of the invention are represented by the formula:

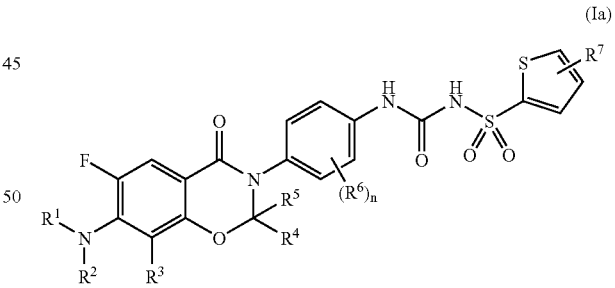

(Ia)

wherein the subscript n is an integer of from 0 to 2. The remaining R groups ($R^1$, $R^2$, $R^3$, $R^4$, $R^5$, $R^6$ and $R^7$) have the meanings provided above with reference to general formula I. Further preferred are those embodiments in which wherein n is 0 or 1; $R^1$ is $C_{1-4}$ alkyl, $C_{3-5}$ cycloalkyl, $C_{3-5}$ cycloalkyl-alkyl, or halosubstituted benzyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is H or $C_{1-4}$ alkyl, $C_{1-4}$ haloalkyl, —CN, —C≡CH or —CONH$_2$; $R^6$, when present is selected from the group consisting of halogen, $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N $(R^{6b})_2$ wherein the subscript m is 1 or 2 and each $R^{6b}$ is independently selected from the group consisting of H, $C_{1-4}$ alkyl and $C_{1-4}$ alkanoyl; $R^7$ is H, $C_{1-4}$ alkyl or halogen. Still further preferred are those embodiments in which $R^1$ is $C_{1-4}$ alkyl; $R^4$ is H or $CH_3$; $R^5$ is H or $CH_3$; $R^6$, when present is selected from the group consisting of halogen, $C_{1-4}$ alkyl and $C_{1-4}$ alkoxy; and $R^7$ is halogen or $C_{1-4}$ alkyl. Even further preferred are those embodiments in which $R^1$ is methyl; $R^4$ is H; $R^5$ is H or $CH_3$; $R^7$ is chloro, and is attached at the 5-position of the thienyl ring; n is 0 or 1, and $R^6$ when present is selected from the group consisting of halogen, $C_{1-4}$ alkyl, $-OCH_2CH_2OH$, $-OCH_2CH_2OCH_3$, $-OCH_2OCH_3$, $-OCH_2CH_2OC(O)CH_3$ and $-O(CH_2)_2N(CH_3)_2$.

In another group of preferred embodiments, the compounds of the invention are represented by the formula:

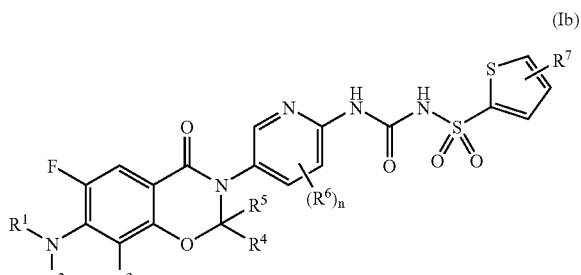

(Ib)

wherein the subscript n is an integer of from 0 to 2. The remaining R groups ($R^1$, $R^2$, $R^3$, $R^4$, $R^5$, $R^6$ and $R^7$) have the meanings provided above with reference to general formula I.

In yet another group of preferred embodiments, the compounds of the invention are represented by the formula:

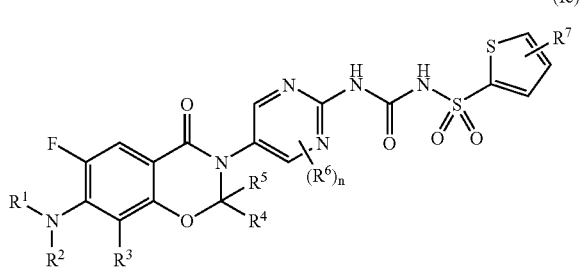

(Ic)

wherein the subscript n is an integer of from 0 to 2. The remaining R groups ($R^1$, $R^2$, $R^3$, $R^4$, $R^5$, $R^6$ and $R^7$) have the meanings provided above with reference to general formula I.

In still another group of preferred embodiments, the compounds of the invention are represented by the formula:

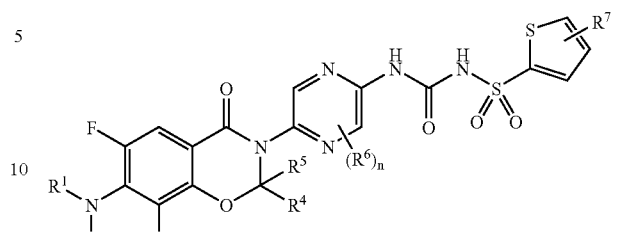

(Id)

wherein the subscript n is an integer of from 0 to 2. The remaining R groups ($R^1$, $R^2$, $R^3$, $R^4$, $R^5$, $R^6$ and $R^7$) have the meanings provided above with reference to general formula I.

In another group of preferred embodiments, the compounds of the invention are represented by the formula:

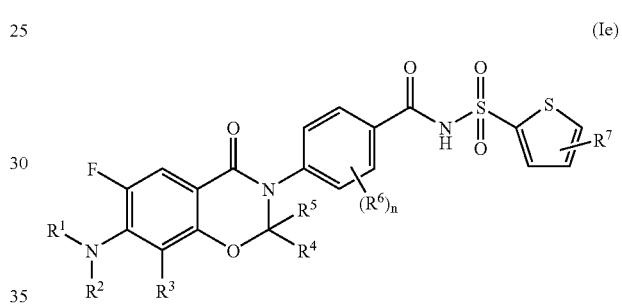

(Ie)

wherein the subscript n is an integer of from 0 to 2. The remaining R groups ($R^1$, $R^2$, $R^3$, $R^4$, $R^5$, $R^6$ and $R^7$) have the meanings provided above with reference to general formula I. In some preferred compounds, $R^6$ is fluoro.

Some particularly preferred compounds of the invention are those having the formulae:

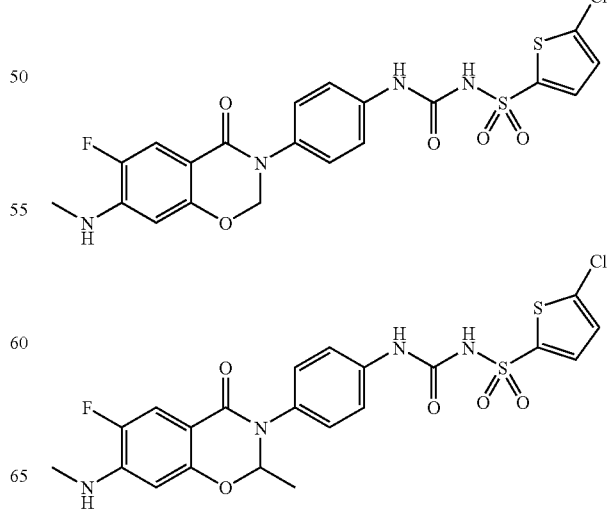

-continued
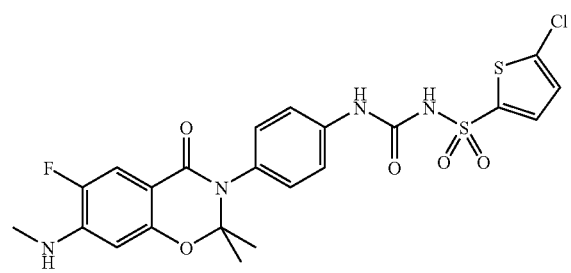
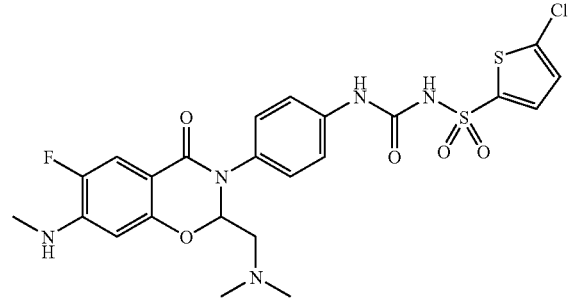
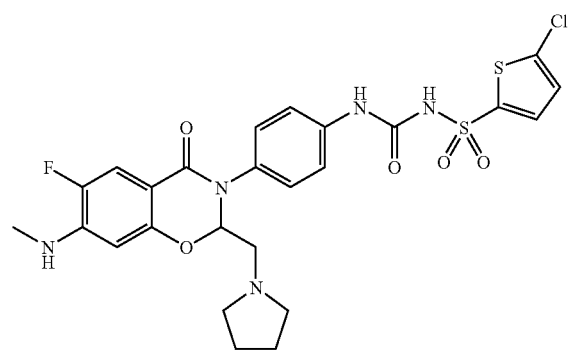
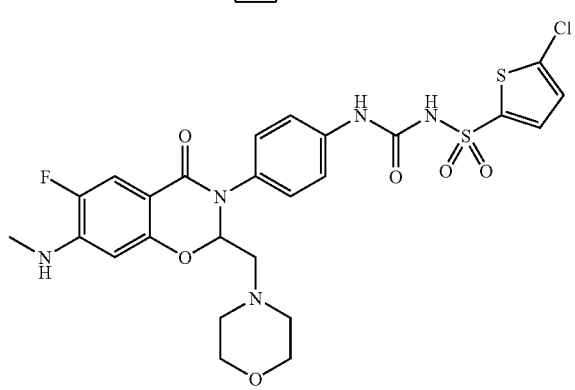
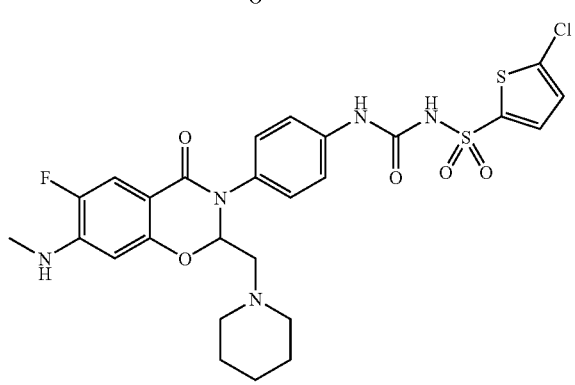
-continued
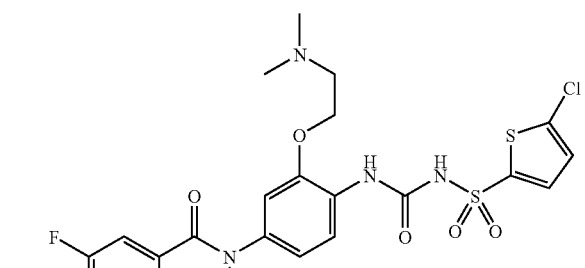
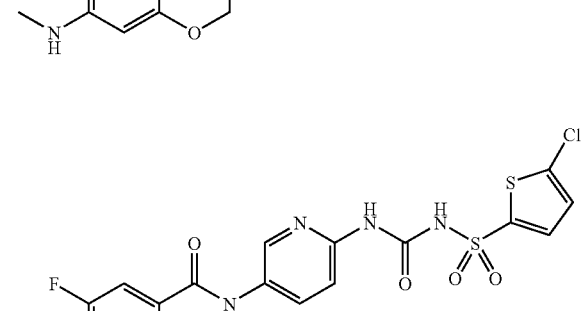
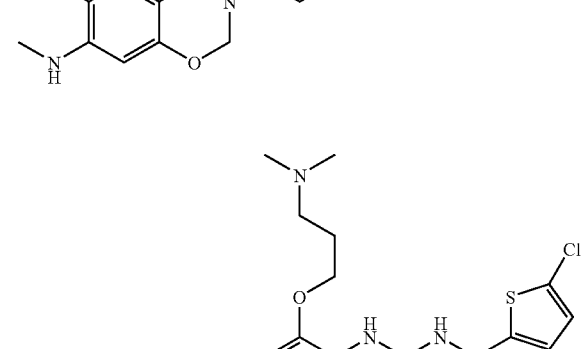
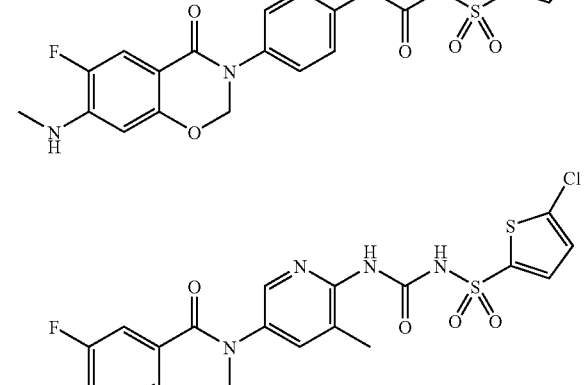
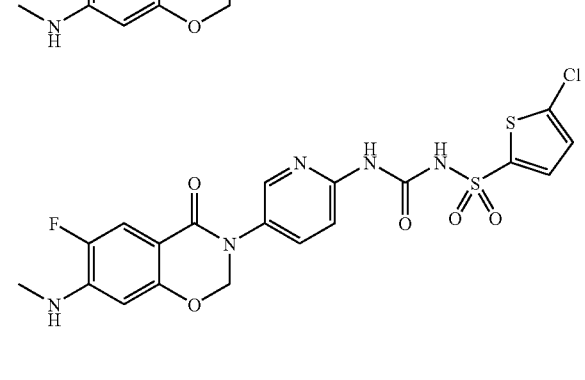

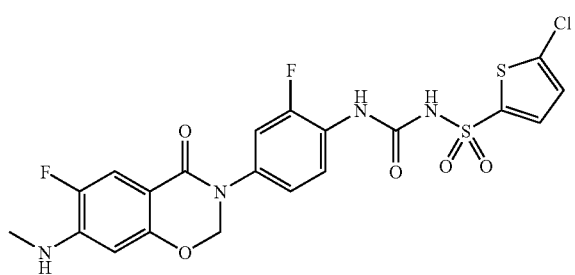
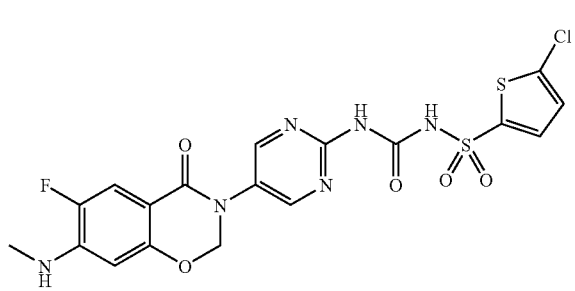
Still other preferred compounds of the present invention are those represented by the formulae:
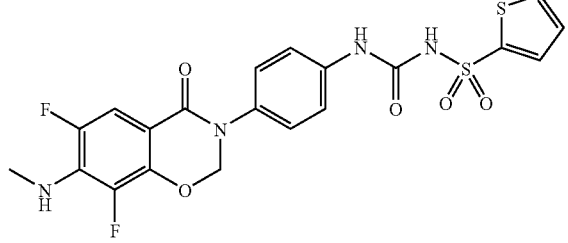
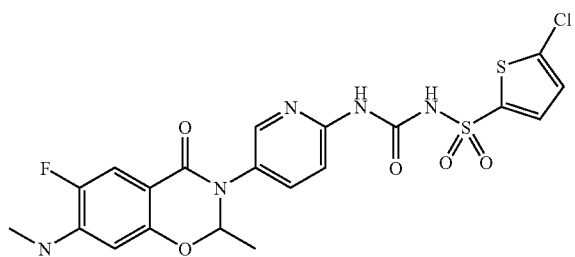
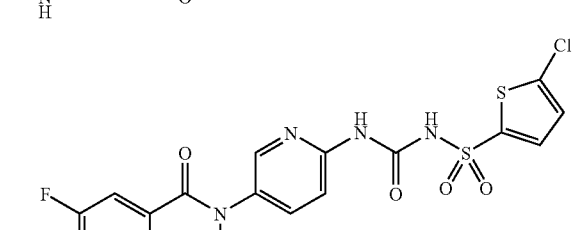
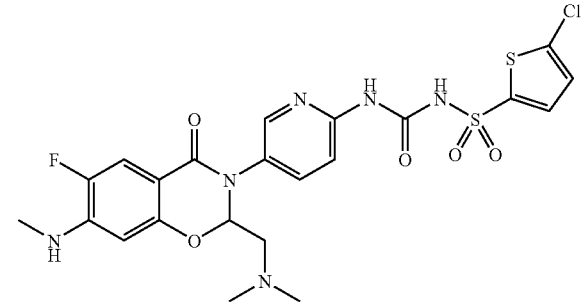
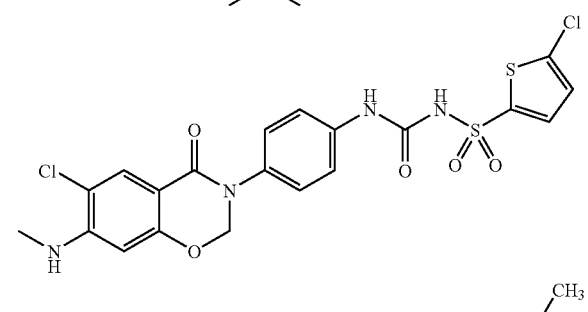
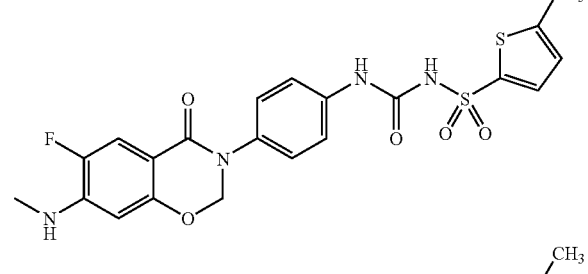
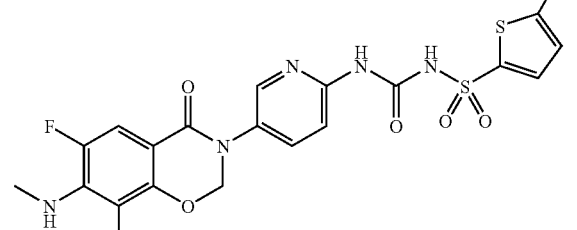
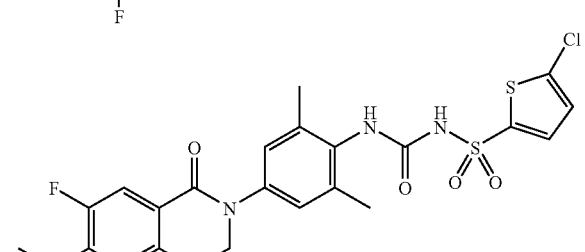
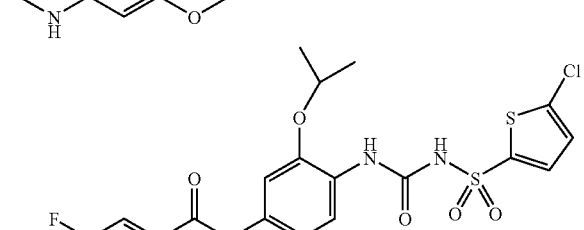

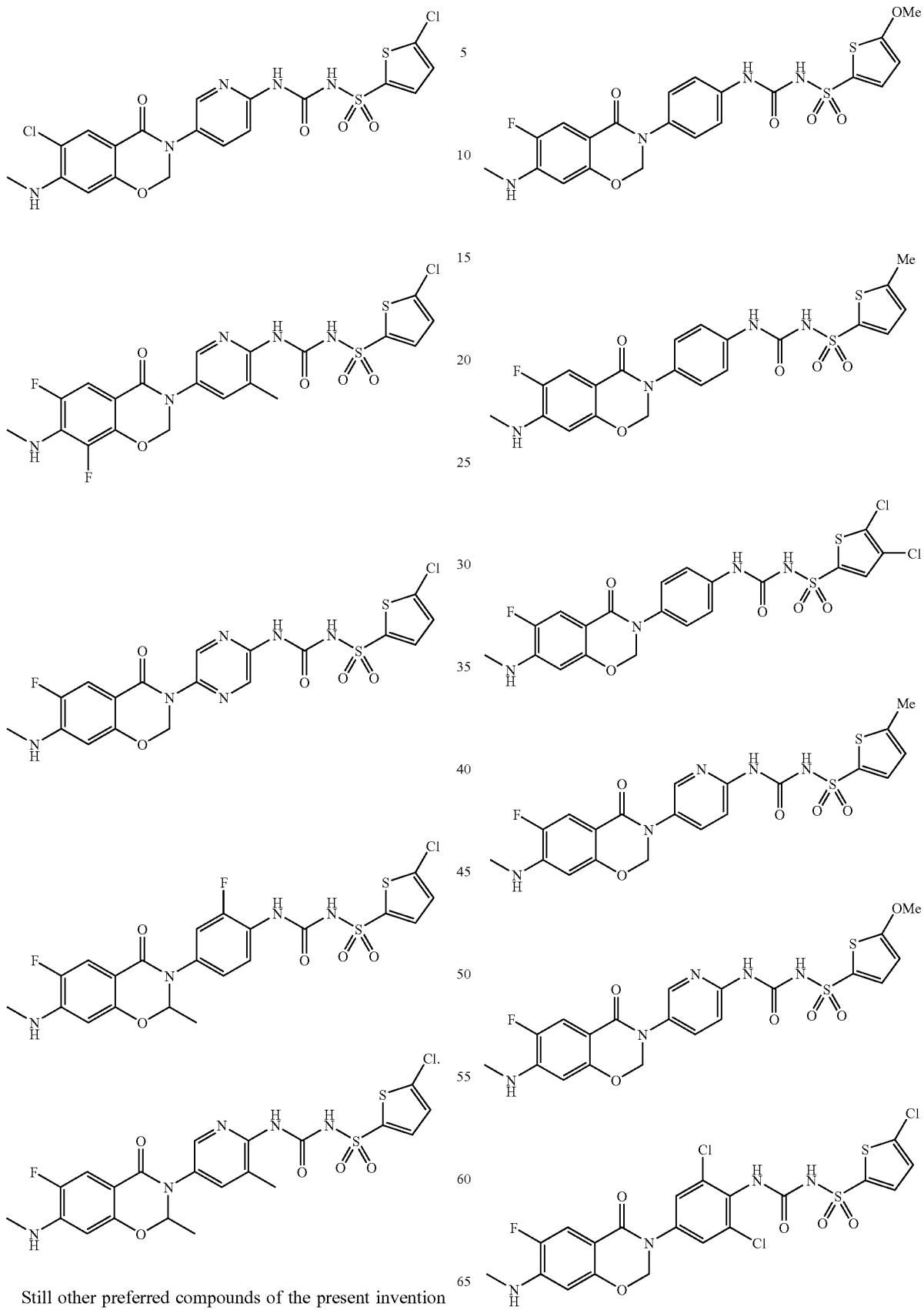
Still other preferred compounds of the present invention are those represented by the formulae:

-continued

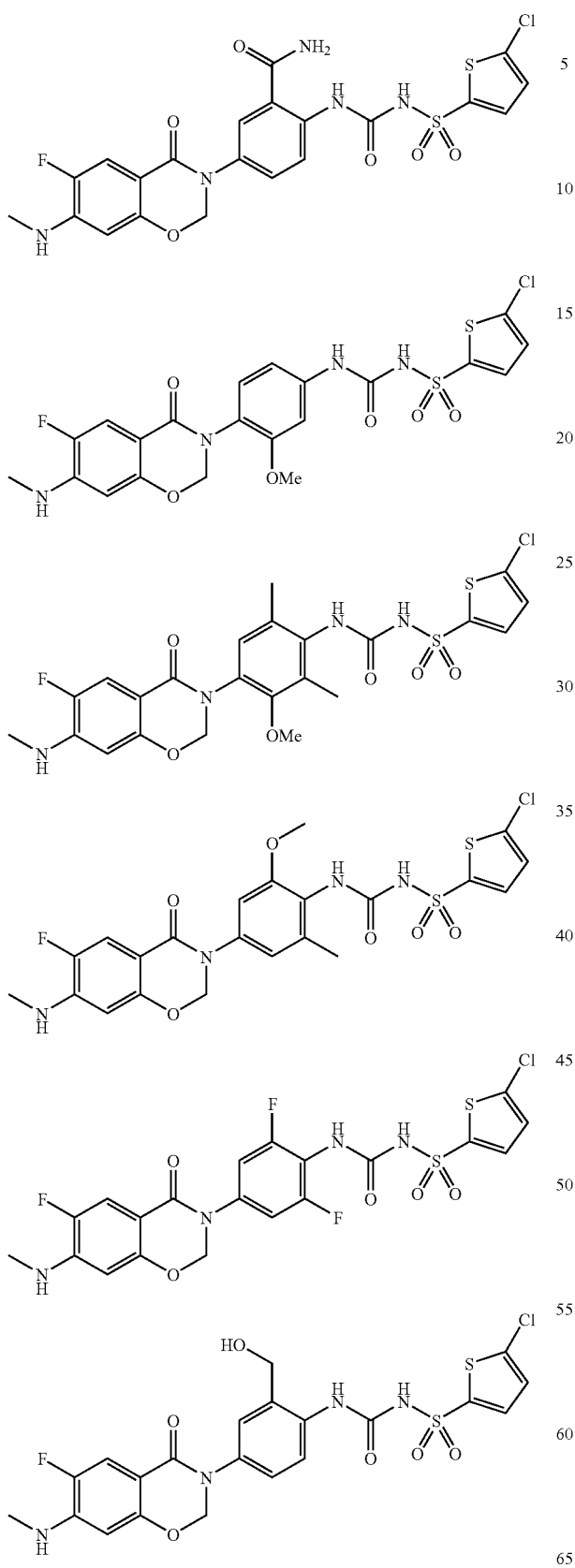

-continued

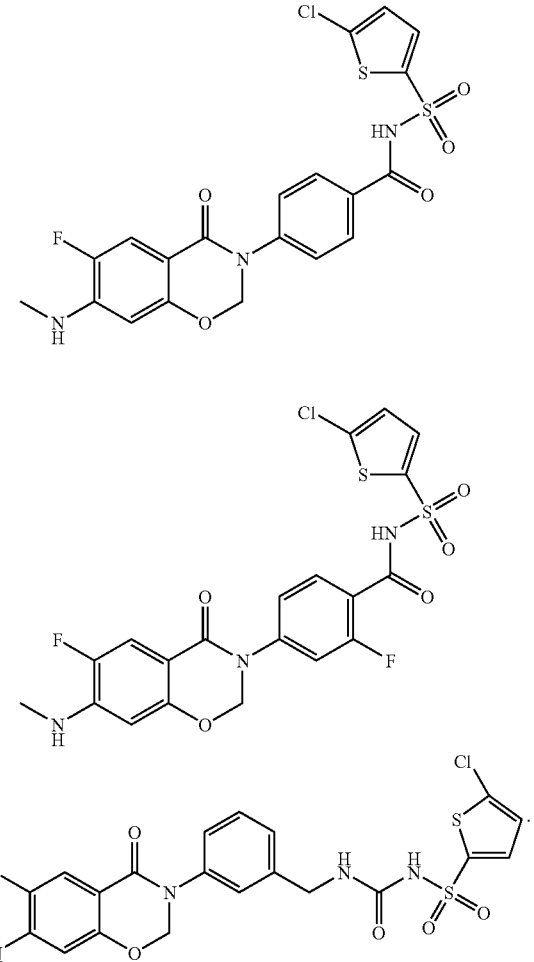

Consistent with the practice of those of skill in the art, unlabeled bonds (e.g., those with an unlabeled terminus) are meant to illustrate methyl ($CH_3$) groups.

General Synthetic Schemes

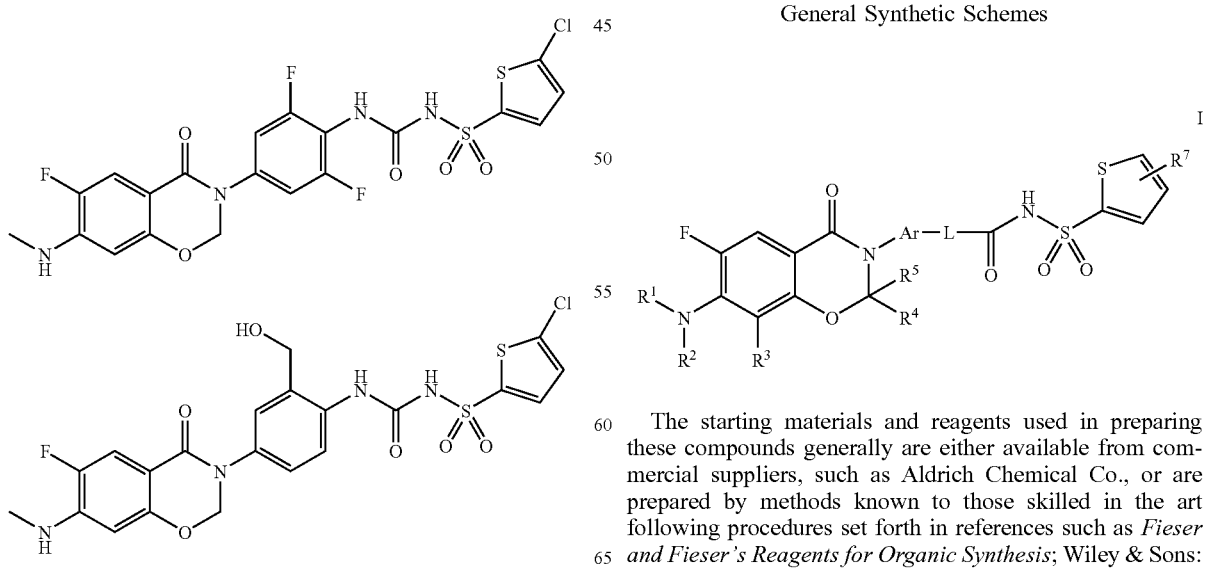

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A describes a method of preparing a compound of formula I wherein $R^3$, $R^4$ and $R^5$=H; $R^1$, $R^2$, $R^6$ can be as described hereinbefore, Ar is substituted aryl and heteroaryl and $R^7$ is chloro.

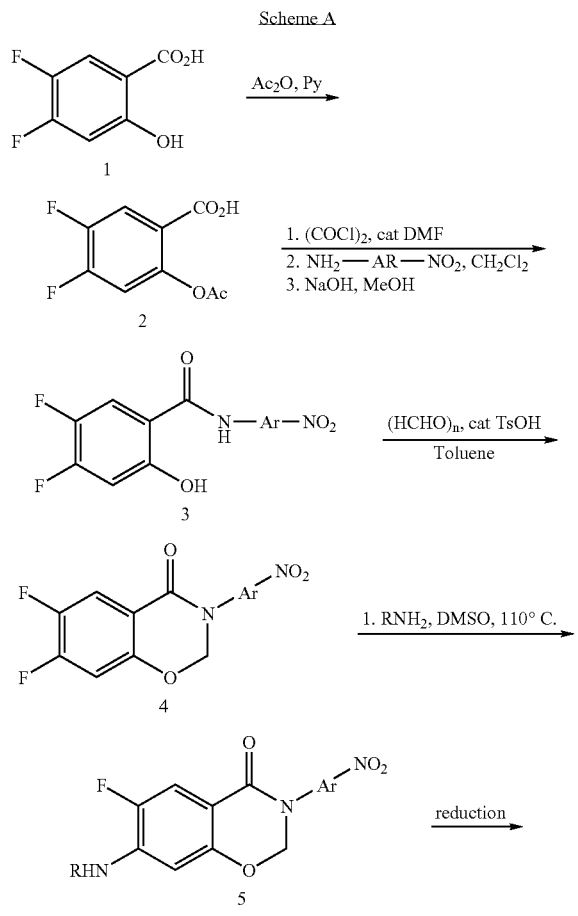

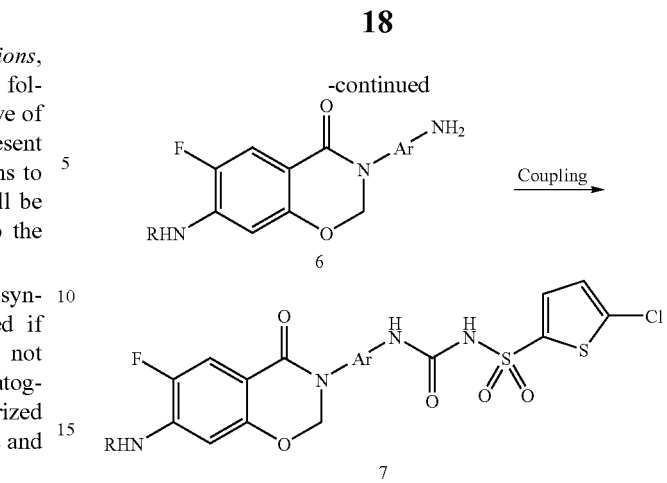

A compound of Formula I can be prepared by reacting 4,5-difluorosalicylic acid with acetic anhydride followed by acid chloride formation with oxalyl chloride which was converted to amides by reaction with various nitroaryl compounds. Deacetylation under basic conditions to affords salicylamides 3. The intermediate salicylamides 3 were cyclized with paraformaldehyde to benzoxazinone compounds 4. The 7-fluoro group can be displaced with various amines or anilines in dimethyl sulfoxide at 100–120° C. to afford intermediate 5. The nitro group of compound 5 can be reduced by procedures known to one skilled in the art to yield free amino group. For example, a method of reduction can be carried out by hydrogenation, with a suitable catalyst (e.g., 10% palladium on carbon) in an appropriate solvent, typically an alcohol. The formation of sulfonylurea linkage can be accomplished by treating the reduced product amine 6 with a pre-mixed solution of 5-chlorothiophene-2-sulfonamide, N,N'-disuccinimidyl carbonate and tetramethylguanidine in dichloromethane at room temperature to afford the sulfonylurea 7 or by treating amine 6 with the ethyl carbamate of 5-chloro-thiophene-2-sulfonamide in refluxing toluene to afford the sulfonylurea 7.

Scheme B illustrates the preparation of compounds of formula I, wherein L is —NH—; $R^3$, $R^4$ and $R^5$=H; $R^1$, $R^2$, $R^6$ can be as described hereinbefore, Ar is substituted aryl and heteroaryl and $R^7$ is chloro.

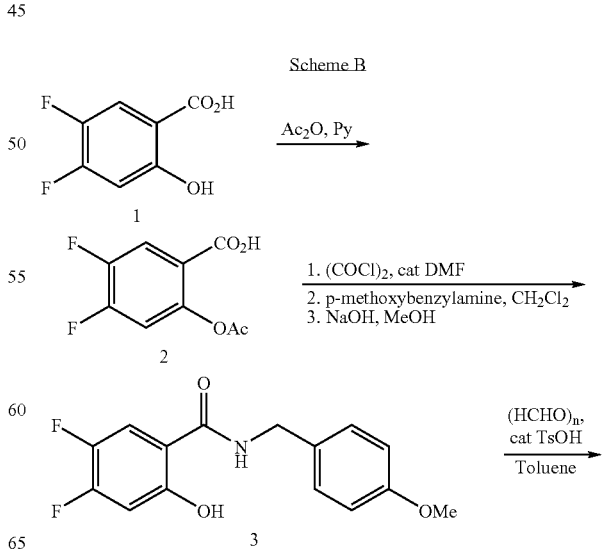

19

-continued

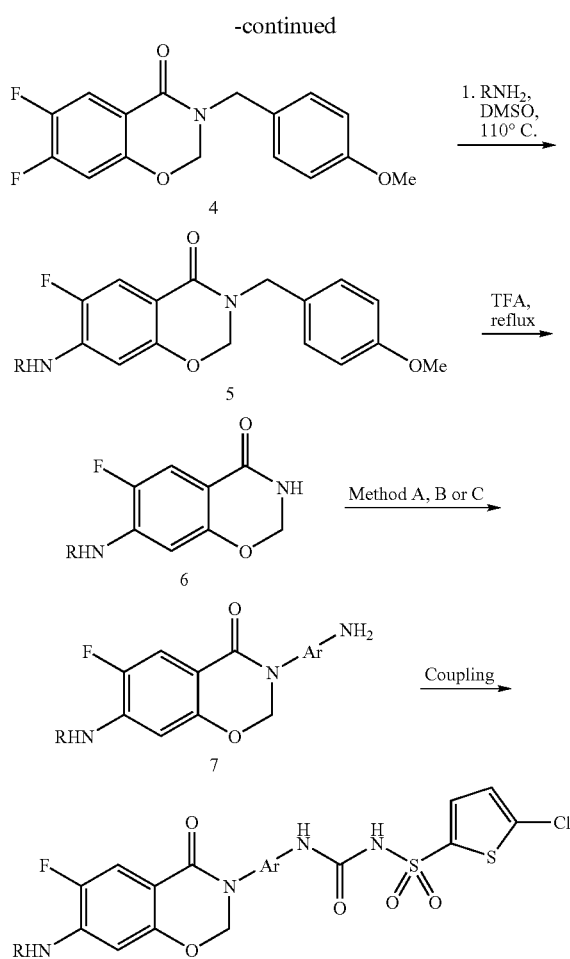

A compound of Formula I with varying Ar groups can be prepared by first synthesizing the common intermediate 6 in 5 steps (Scheme B). The acid chloride from Scheme A can be treated with p-methoxybenzylamine followed by cyclization with paraformaldehyde to afford the benzoxazinone ring system. The difluoro intermediate 4 can be treated with various amines or anilines specifically with methylamine to displace the 7-fluoro group to afford intermediate 5. The p-methoxybenzyl functionality can then be hydrogenolyzed to afford common intermediate 6. A variety of halo-substituted nitroaromatic compounds can be coupled with 6 using Method A, conditions which are alkylation in presence of base such as cesium carbonate, followed by reduction of the nitro group using catalytic hydrogenation or tin(II) dichloride dihydrate to give 7. Also, a variety of halo-substituted arylamines can be coupled to 6 using Method B, conditions which are copper catalyzed coupling to give 7. The formation of sulfonylurea linkage can be accomplished by treating the product amine 7 with the ethyl carbamate of 5-chlorothiophene-2-sulfonamide in refluxing toluene to afford the sulfonylurea 8 or treating with 5-chlorothiophene-2-sulfonamide, N,N'-disuccinimidyl carbonate and tetramethylguanidine in dichloromethane at room temperature to afford the sulfonylurea 8. The examples provided in detail below illustrate compounds prepared by the general methods provided.

20

Scheme C illustrates the preparation of compounds of formula I, wherein L is a bond; $R^3$, $R^4$ and $R^5$=H; $R^1$, $R^2$, $R^6$ can be as described hereinbefore, Ar is substituted aryl and heteroaryl and $R^7$ is chloro.

Scheme C

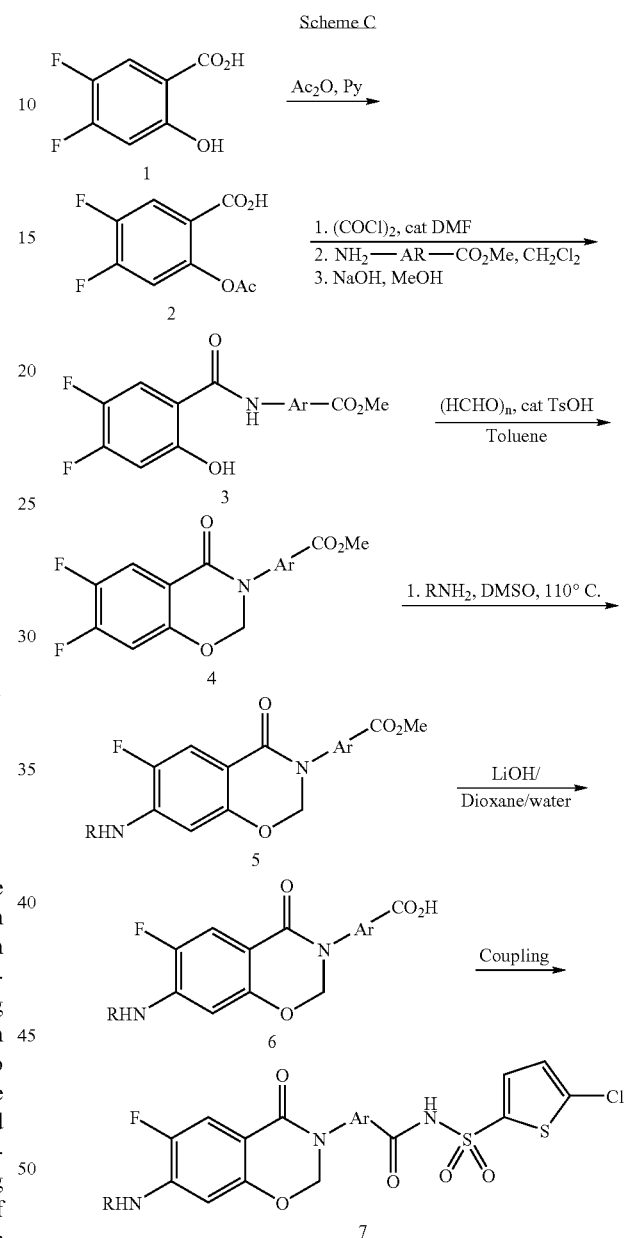

A compound of Formula I, wherein acylsulfonamide is the linker, can be prepared by treating acid chloride of 2 with appropriately substituted methyl-4-aminobenzoate to provide amide intermediate. Deacetylation under basic conditions affords salicylamides 3. The intermediate salicylamides 3 were cyclized with paraformaldehyde to benzoxazinone compounds 4. The 7-fluoro group can be displaced with various amines or anilines in dimethyl sulfoxide at 100–120° C. to afford intermediate 5. The ester of compound 5 can be converted to the carboxylic acid by treatment with lithium hydroxide in an appropriate solvent or solvent mixture such as dioxane/water or THF/water. Conversion of the carboxylic acid to acyl sulfonamide 7 is accomplished by treatment with EDC, DMAP and a suitably substituted sulfonamide in either dichloromethane or DMF as the solvent.

Compositions

In another aspect of the invention, pharmaceutical compositions are provided in which compounds of formulae I, Ia, Ib, Ic, Id or Ie, alone or in combination, are combined with a pharmaceutically acceptable carrier.

The pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles.

Typical adjuvants which may be incorporated into tablets, capsules and the like include, but are not limited to, binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Additionally, dosage formulations of compounds of formulae I, Ia, Ib, Ic, Id or Ie, or pharmaceutical compositions containing a compound of the invention, to be used for therapeutic administration must be sterile. Sterility can be readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formulae I, Ia, Ib, Ic, Id or Ie, or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formulae I, Ia, Ib, Ic, Id or Ie, and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be provided in the form of liposome delivery systems, such as small unilamellar vesicles, large unilamellar vesicles and multilamellar vesicles. Liposomes can be formed from a variety of lipids, such as cholesterol, stearylamine or phosphatidylcholines, used methods well known to one of skill in the art.

Methods of Treatment/Administration

In yet another aspect, the present invention provides methods for preventing or treating thrombosis in a mammal by administering to the mammal a therapeutically effective amount of a compound of formulae I, Ia, Ib, Ie, Id or Ie, alone or as part of a pharmaceutical composition of the invention as described above. Compounds of formulae I, Ia, Ib, Ie, Id or Ie, and pharmaceutical compositions of the invention containing a compound of formulae I, Ia, Ib, Ie, Id or Ie, of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Still other agents that can be administered with the compounds of the present invention include antiplatelet compounds, fibrinolytics, anti-inflammatory compounds, cholesterol-lowering agents, blood-pressure-lowering agents and serotonin blockers. Suitable antiplatelet compounds include GPIIB-IIIa antagonists, aspirin, phosphodiesterase III inhibitors and thromboxane A2 receptor antagonists. Suitable anticoagulants include thrombin inhibitors, coumadin (Warfarin), heparin and enoxaparin sodium injection. Suitable anti-inflammatory compounds include non-steroidal anti-inflammatory agents, cyclooxygenase-2 inhibitors and rheumatoid arthritis agents. Coadministrations of these agents with the compounds of the invention may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

In related methods, the compounds of the invention are useful for the prevention of a secondary ischemic event. In these methods, compounds of the invention or their pharmaceutical compositions are administered to a patient who has suffered a primary ischemic event in an amount sufficient to prevent or reduce the likely occurrence of a secondary event. Generally, the primary and/or secondary ischemic event is selected from myocardial infraction, stable or unstable angina, acute reocclusion after percutaneous transluminal coronary angioplasty, restenosis, thrombotic stroke, transient ischemic attack, reversible ischemic neurological deficit and intermittent claudication.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formulae I, Ia, Ib, Ic, Id or Ie, employed, the specific use for which the compound or pharmaceutical composition is employed, and other factors which those skilled in the medical arts will recognize.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formulae I, Ia, Ib, Ic, Id or Ie, is combined with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

The following preparations and examples are given to enable those skilled in the art to more clearly understand and to practice the present invention. They should not be considered as limiting the scope of the invention, but merely as being illustrative and representative thereof.

EXAMPLES

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Example 1

4,5-difluoro-2-hydroxy-N-(4-nitrophenyl)benzamide

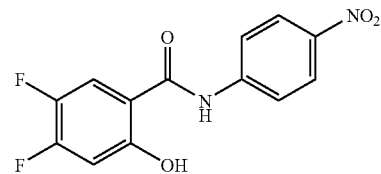

To a solution 4,5-difluoro-2-hydroxybenzoic acid (1 g, 6 mmol, prepared by the method of Kazuto Umezv, U.S. Pat. No. 6,166,246) in pyridine (2 mL) was added acetic anhydride (0.8 mL, 7 mol) and the mixture was stirred at room temperature for 2 hr. To this added 10% HCl (10 mL) and extracted with ethyl acetate. The ethyl acetate was evaporated and the residue taken up in dichloromethane (10 mL). To this solution was added oxalyl chloride (1 mL) and few drops of dimethylformamide and stirred for 1 hr at room temperature. The solvent was removed and the acid chloride was re-dissolved in dichloromethane (10 mL) followed by the slow addition to a dichloromethane solution (10 mL) of p-nitroaniline (0.880 mL, 6.5 mmol). The reaction mixture after 2 hr showed new peak by HPLC and complete disappearance of the starting material. The dichloromethane was removed and the residue dissolved in methanol and to it added 10% aqueous NaOH solution (3 mL) and mixture stirred for 1 hr. The methanol was removed and the residue acidified and extracted with ethyl acetate. The ethyl acetate layer was dried, filtered and evaporated to yield 1.5 g (85%) of N-(4-methoxybenzyl)-4,5-difluoro-2-hydroxybenzamide as a white solid. RP-HPLC: 2.67 min; ES-MS (M+H)$^+$ =295.0; 1H-NMR (DMSO-d$_6$) δ (ppm): 6.8 (dd, 1 H), 7.9 (dd, 1 H), 7.94 (d, 2 H), 8.24 (d, 2 H).

Example 2

6,7-difluoro-3-(4-nitrophenyl)-2,3-dihydrobenzo[e][1,3]oxazin-4-one

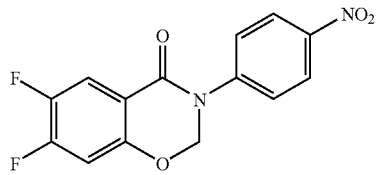

To 4,5-difluoro-2-hydroxy-N-(4-nitrophenyl)benzamide (0.13 g, 0.44 mmol) in toluene (5 ml) was added paraformadehyde (0.3 g, 10 mmol) and p-toluenesulfonic acid (0.01 g, 0.05 mmol) and the reaction heated to 120° C. for 3 hr with azeotropic removal of water. Saturated sodium bicarbonate (10 ml) was added and product extracted with ethyl acetate, dried over anhydrous sodium sulfate and concentrated to give 0.11 mg (81%) of 6,7-difluoro-3-(4-nitrophenyl)-2,3-dihydrobenzo[e][1,3]oxazin-4-one. RP-HPLC: 2.54 min; ES-MS (M+H)$^+$=307.0; 1H-NMR (MeOH-d$_4$) δ (ppm): 5.78 (s, 2 H), 7.04 (dd, 1 H), 7.64 (d, 2 H), 7.82 (dd, 1 H), 8.3 (d, 2 H).

Example 3

6-fluoro-7-(methylamino)-3-(4-nitrophenyl)-2,3-dihydrobenzo[e][1,3]oxazin-4-one

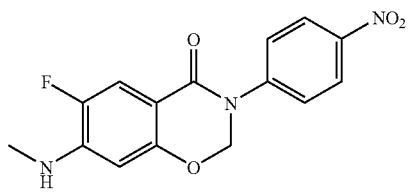

To 6,7-difluoro-3-(4-nitrophenyl)-2,3-dihydrobenzo[e][1,3]oxazin-4-one (0.05 g, 0.16 mmol) in dimethyl sulfoxide (0.5 ml) was added methyl amine (0.3 ml, 2M solution in tetrahydrofuran) and the reaction heated to 140° C. for 1 hr. Water was added and product extracted with ethyl acetate, dried over anhydrous sodium sulfate and concentrated to give 0.42 mg (81%) of 6-fluoro-7-(methylamino)-3-(4-nitrophenyl)-2,3-dihydrobenzo[e][1,3]oxazin-4-one. RP-HPLC: 2.38 min; ES-MS (M+H)$^+$=318.0; 1H-NMR (DMSO-d$_6$) δ (ppm): 3.1 (s, 3 H), 5.73 (s, 2 H), 6.2 (d, 1 H), 7.38 (d, 1 H), 7.61 (d, 1 H), 8.2 (d, 2 H).

Example 4

3-(4-aminophenyl)-6-fluoro-7-(methylamino)-2,3-dihydrobenzo[e][1,3]oxazin-4-one

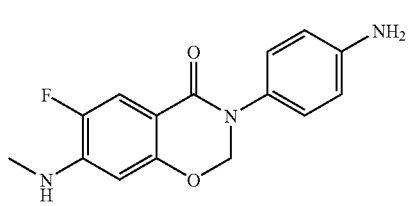

To a suspension of 6-fluoro-7-(methylamino)-3-(4-nitrophenyl)-2,3-dihydrobenzo[e][1,3]oxazin-4-one (0.108 g, 0.33 mmol) in ethanol (6 mL) under Ar was added 10% Pd/C (0.04 g, 0.03 mmol Pd). The mixture was hydrogenated under 1 atm H2 overnight, filtered through Celite and concentrated to give 0.096 g (98%) of 3-(4-aminophenyl)-6-fluoro-7-(methylamino)-2,3-dihydrobenzo[e][1,3]oxazin-4-one. RP-HPLC: 1.37 min; ES-MS (M+H)$^+$=288.0; 1H-NMR (MeOH-d$_4$) δ (ppm): 2.8 (s, 3 H), 5.5 (s, 2 H), 6.2 (d, 1 H), 7.2 (d, 2 H), 7.3 (d, 2 H), 7.4 (d, 1 H).

Example 5

1-(5-chlorothiophen-2-ylsulfonyl)-3-(4-(6-fluoro-7-(methylamino)-4-oxo-2H-benzo[e][1,3]oxazin-3(4H)-yl)phenyl)urea

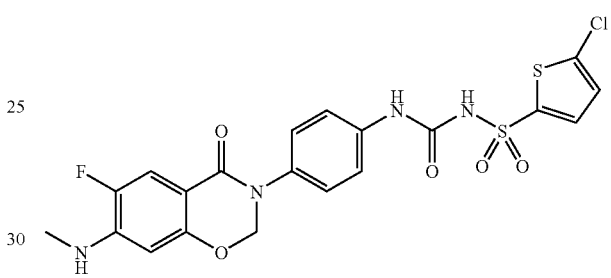

A mixture of 3-(4-aminophenyl)-6-fluoro-7-(methylamino)-2,3-dihydrobenzo[e][1,3]oxazin-4-one (Ex. 4) (130 mg, 0.45 mmol) and (5-Chloro-thiophene-2-sulfonyl)-carbamic acid ethyl ester (150 mg, 0.53 mmol, 1.2 eq) in dry 1,4-dioxan (3 mL) was heated at 110° C. for 2 hr. Upon cooling, the reaction was concentrated in vacuo and the crude residue was purified by HPLC (C-18) to give 86 mg (37%) of pure 1-(5-chlorothiophen-2-ylsulfonyl)-3-(4-(6-fluoro-7-(methylamino)-4-oxo-2H-benzo[e][1,3]oxazin-3(4H)-yl)phenyl)urea. RP-HPLC: 2.49 min; ES-MS (M+H)$^+$=511.0; 1H-NMR (MeOH-d$_4$) δ (ppm): 2.8 (s, 3 H), 5.4 (s, 2 H), 6.2 (d, 1 H), 6.9 (d, 2 H), 7.1 (d, 2 H), 7.3 (d, 1 H), 7.4 (d, 1 H), 7.5 (d, 2 H).

Example 6

4,4-difluoro-2-hydroxy-N-(3-methyl-4-nitrophenyl)benzamide

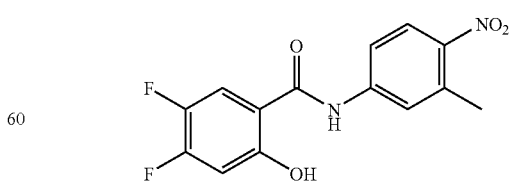

RP-HPLC: 2.8 min; ES-MS (M+H)$^+$=309.0; 1H-NMR (MeOH-d$_4$) δ (ppm): 2.6 (s, 3 H), 6.9 (dd, 1 H), 7.7 (m, 2 H), 7.9 (dd, 1 H), 8.0 (d, 1 H).

Example 7

6,7-difluoro-3-(3-methyl-4-nitrophenyl)-2,3-dihydrobenzo[e][1,3]oxazin-4-one

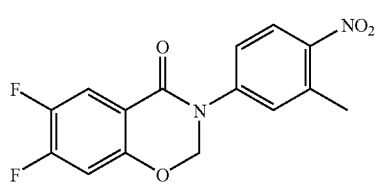

RP-HPLC: 2.69 min; ES-MS (M+H)$^+$=321.0; 1H-NMR (MeOH-d$_4$) δ (ppm): 2.6 (s, 3 H), 5.7 (s, 2 H), 7.1 (dd, 1 H), 7.45 (d, 1 H), 7.48 (d, 1 H), 7.8 (dd, 1 H), 8.0 (d, 2 H).

Example 8

6-fluoro-3-(3-methyl-4-nitrophenyl)-7-(methylamino)-2,3-dihydrobenzo[e][1,3]oxazin-4

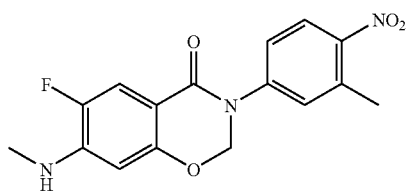

RP-HPLC: 2.54 min; ES-MS (M+H)$^+$=332.0; 1H-NMR (MeOH-d$_4$) δ (ppm): 2.2 (s, 3 H), 2.8 (s, 3 H), 5.6 (s, 2 H), 6.2 (d, 1 H), 7.0 (d, 1 H), 7.4 (d, 1 H), 7.7 (d,1 H) 8.1 (d, 1 H).

Example 9

3-(4-amino-3-methylphenyl)-6-fluoro-7-(methylamino)2,3-dihydro[e][1,3]oxazin-4-one

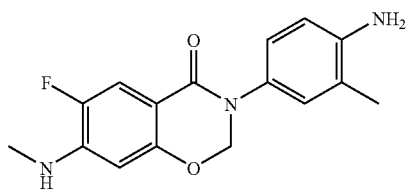

RP-HPLC: 1.36 min; ES-MS (M+H)$^+$=291.0.

Example 10

1-(5-chlorothiophen-2-ylsulfonyl)-3-(4-(6-fluoro-7-(methylamino)-4-oxo-2H-benzo [e][1,3]oxazin-3 (4H)-yl)-2-methylphenyl)urea

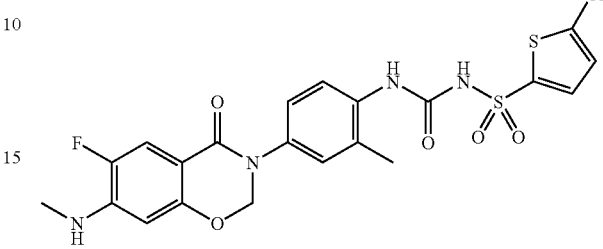

An analogous amide coupling procedure to that described in Ex. 1 was performed with 2-(chlorocarbonyl)-4,5-difluorophenyl acetate (Ex. 1) and 3-methyl-4-nitrobenzenamine. Ring cyclization was performed using paraformaldehyde as described in Ex 2. Methyl amine displacement of the fluorine was performed analogous to the procedure outlined in Ex. 3. Reduction of the nitro group was effected using the procedure outlined in Ex. 4. Coupling to form the sulfonylurea urea was achieved using the method described in Ex. 5 to give 1-(5-chlorothiophen-2-ylsulfonyl)-3-(4-(6-fluoro-7-(methylamino)-4-oxo-2H-benxo [e][1,3]oxazin-3(4H)-yl)-2-methylphenyl)urea. RP-HPLC: 2.54 min; ES-MS (M+H)$^+$=524.0; 1H-NMR (MeOH-d$_4$) δ (ppm): 2.2 (s, 3 H), 2.8 (s, 3 H), 5.4 (s, 2 H), 6.2 (d, 1 H), 6.9 (d, 1 H), 7.05 (dd, 1 H), 7.1 (d, 1 H), 7.35 (d, 1 H), 7.39 (d, 1 H), 7.7 (d, 1 H).

Example 11

4,4-difluoro-2-hydroxy-N-(2-methoxy-4-nitrophenyl)benzamide

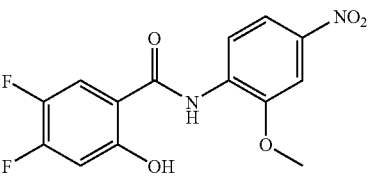

RP-HPLC: 2.8 min; ES-MS (M+H)$^+$=325.0.

Example 12

6,7-difluoro-3-(2-methoxy-4-nitrophenyl)-2,3-dihydrobenzo[e][1,3]oxazin-4-one

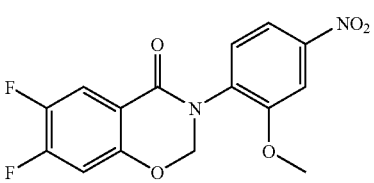

RP-HPLC: 2.6 min; ES-MS (M+H)$^+$=337.0

Example 13

6-fluoro-3-(2-methoxy-4-nitrophenyl)-7-(methylamino)-2,3-dihydrobenzo[e][1,3]oxazin-4-one

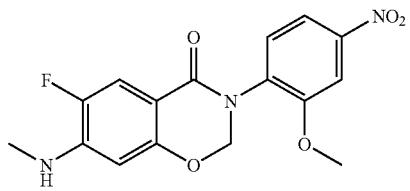

RP-HPLC: 2.42 min; ES-MS (M+H)$^+$=348.3

Example 14

3-(4-amino-2-methoxyphenyl)-6-fluoro-7-(methylamino)2,3-dihydro[e][1,3]oxazin-4-one

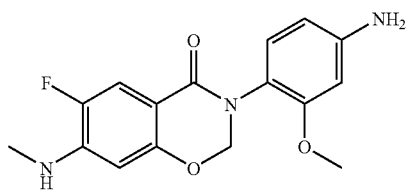

RP-HPLC: 1.39 min; ES-MS (M+H)$^+$=318.0

Example 15

1-(5-chlorothiophen-2-ylsulfonyl)-3-(4-(6-fluoro-7-(methylamino)-4-oxo-2H-benzo [e][1,3]oxazin-3 (4H)-yl)-3-methoxyphenyl)urea

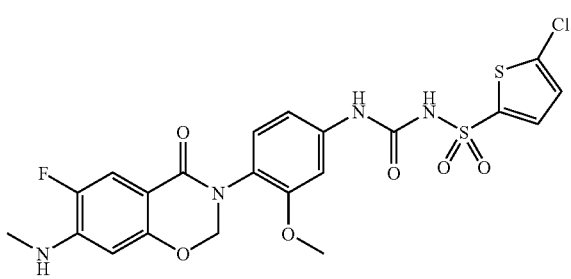

An analogous amide coupling procedure to that described in Ex. 1 was performed on 2-(chlorocarbonyl)-4,5-difluorophenyl acetate (Ex. 1) and 2-methoxy-4-nitrobenzenamine. Ring cyclization was performed using paraformaldehyde as described in Ex 2. Methyl amine displacement of the fluorine was performed analogous to the procedure outlined in Ex. 3. Reduction of the nitro group was effected using the procedure outlined in Ex. 4. Coupling to form the sulfonyl urea was achieved using the method described in Ex. 5 to give 1-(5-chlorothiophen-2-ylsulfonyl)-3-(4-(6-fluoro-7-(methylamino)-4-oxo-2H-benzo[e][1,3]oxazin-3 (4H)-yl)-3-methoxyphenyl)urea. RP-HPLC: 2.6 min; ES-MS (M+H)$^+$=540.9; 1H-NMR (MeOH-d$_4$) δ (ppm): 2.8 (s, 3 H), 3.82 (s, 3 H), 5.3 (s, 2 H), 6.2 (d, 1 H), 6.9 (dd, 1 H), 7.1 (d, 1 H), 7.18 (d, 1 H), 7.3 (d, 1 H), 7.36 (d, 1 H), 7.6 (d, 1 H).

Example 16

N-(2-(2-ethoxyethoxy)-4-nitrophenyl)-4,5-difluoro-2-hydroxybenzamide

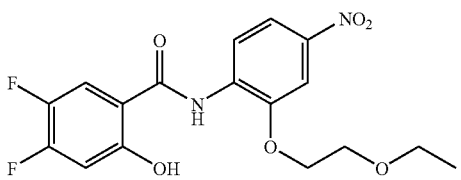

RP-HPLC: 3.4 min; ES-MS (M+H)$^+$=383.3; 1H-NMR (DMSO-d$_6$) δ (ppm): 1.0 (t, 3 H), 3.52 (q, 2 H), 3.8 (t, 2 H), 4.3 (t, 2 H), 7.0 (dd, 1 H), 7.9 (m, 3 H), 8.6 (d, 1 H), 11.1 (bs, 1 H).

Example 17

3-(2-ethoxyethoxy)-4-nitrophenyl)-6,7-difluoro-2,3-dihydrobenzo[e][1,3]oxazin-4-one

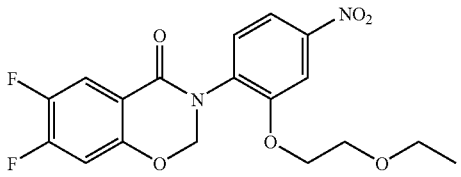

RP-HPLC: 3.3 min; ES-MS (M+H)$^+$=395.0; 1H-NMR (DMSO-d$_6$) δ (ppm): 0.98 (t, 3 H), 3.42 (q, 2 H), 3.6 (t, 2 H), 4.2 (t, 2 H), 5.5 (s, 2 H), 7.4 (dd, 1 H), 7.6 (d, 1 H), 7.8 (dd, 1 H), 7.9 (d, 1 H), 7.97 (d, 1 H).

Example 18

6-fluoro-3-(2-ethoxyethoxy-4-nitrophenyl)-7-(methylamino)-2,3-dihydrobenzo[e][1,3]oxazin-4-one

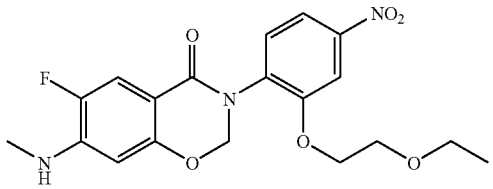

RP-HPLC: 3.05 min; ES-MS (M+H)$^+$=406.2; 1H-NMR (DMSO-d$_6$) δ (ppm): 1.04 (t, 3 H), 3.28 (s, 3 H), 3.42 (q, 2 H), 3.6 (t, 2 H), 4.2 (t, 2 H), 5.4 (s, 2 H), 6.2 (d, 1 H), 7.3 (d, 1 H), 7.5 (d, 1 H), 7.8 (dd, 1 H), 7.9 (d, 1 H).

Example 19

3-(4-amino-2-ethoxyethoxyphenyl)-6-fluoro-7-(methylamino)2,3-dihydro[e][1,3]oxazin-4-one

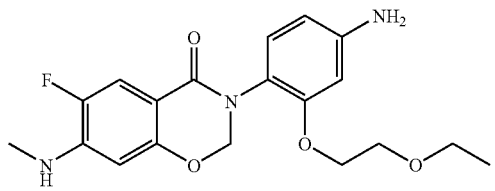

RP-HPLC: 1.9 min; ES-MS (M+H)+=376.

Example 20

1-(5-chlorothiophen-2-ylsulfonyl)-3-(3-(2-ethoxyethoxy)-4-(6-fluoro-7-(methylamino)-4-oxo-2H-benzo[e][1,3]oxazin-3(4H)-yl)phenyl)urea

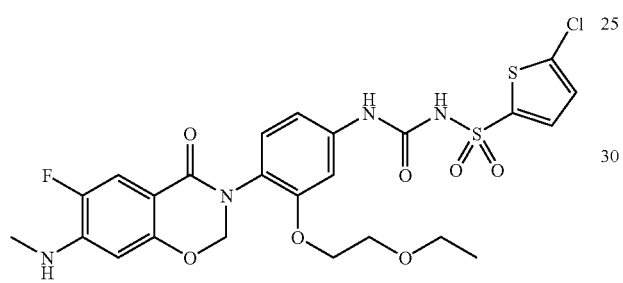

An analogous amide coupling procedure to that described in Ex. 1 was performed on 2-(chlorocarbonyl)-4,5-difluorophenyl acetate (Ex. 1) and 2-(2-ethoxyethoxy)-4-nitrobenzenamine. Ring cyclization was performed using paraformaldehyde as described in Ex 2. Methyl amine displacement of the fluorine was performed analogous to the procedure outlined in Ex. 3. Reduction of the nitro group was effected using the procedure outlined in Ex. 4. Coupling to form the sulfonyl urea was achieved using the method described in Ex. 5 to give 1-(5-chlorothiophen-2-ylsulfonyl)-3-(3-(2-ethoxyethoxy)-4-(6-fluoro-7-(methylamino)-4-oxo-2H-benzo[e][1,3]oxazin-3(4H)-yl)phenyl)urea. RP-HPLC: 3.14 min; ES-MS (M+H)+=599.2, 601.3 (Cl); 1H-NMR (DMSO-$d_6$) δ (ppm): 1.04 (t, 3 H), 2.8 (s, 3H), 3.42 (q, 2 H), 3.7 (t, 2 H), 4.1 (t, 2 H), 5.3 (s, 2 H), 6.8 (dd, 1 H), 6.9 (d 1 H), 7.0 (d, 1 H), 7.3 (d, 1 H), 7.39 (d, 1 H), 7.49 (d, 1 H).

Example 21

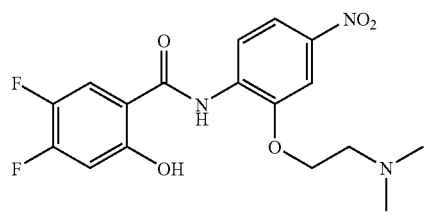

RP-HPLC: 3.43 min; ES-MS (M+H)+=382.2.

Example 22

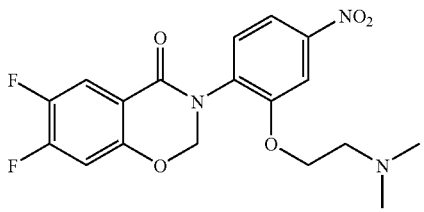

RP-HPLC: 2.18 min; ES-MS (M+H)+=394.2.

Example 23

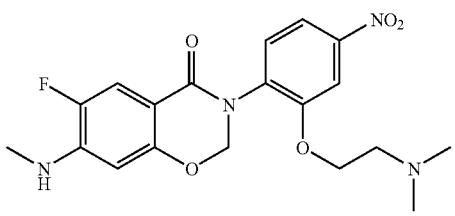

RP-HPLC: 2.1 min; ES-MS (M+H)+=405.0.

Example 24

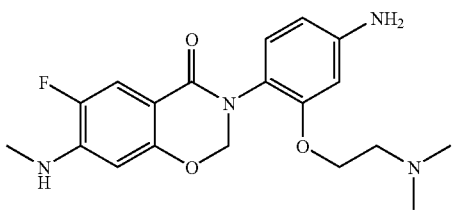

RP-HPLC: 1.44 min; ES-MS (M+H)+=375.1

Example 25

1-(5-chlorothiophen-2-ylsulfonyl)-3-(3-(2-(dimethylamino)ethoxy)-4-(6-fluoro-7-(methylamino)-4-oxo-2H-benzo[e][1,3]oxazin-3(4H)-yl)phenyl)urea

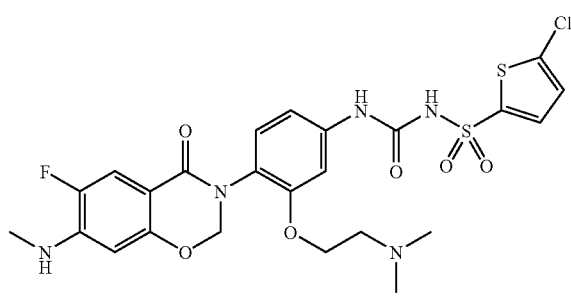

An analogous amide coupling procedure to that described in Ex. 1 was performed on 2-(chlorocarbonyl)-4,5-difluorophenyl acetate (Ex. 1) and 2-(2-(dimethylamino)ethoxy)-

4-nitrobenzenamine. Ring cyclization was performed using paraformaldehyde as described in Ex 2. Methyl amine displacement of the fluorine was performed analogous to the procedure outlined in Ex. 3. Reduction of the nitro group was effected using the procedure outlined in Ex. 4. Coupling to form the sulfonylurea urea was achieved using the method described in Ex. 5 to give 1-(5-chlorothiophen-2-ylsulfonyl)-3-(3-(2-(dimethylamino)ethoxy)-4-(6-fluor-7-(methylamino)-4-oxo-2H-benzo[e][1,3]oxazin-3(4H)-yl)phenyl) urea. RP-HPLC: 2.46 min; ES-MS (M+H)$^+$=598.2; 1H-NMR (MeOH-d$_4$) δ (ppm): 2.82 (s, 3), 2.86 (s, 3 H), 3.46 (t, 2 H), 4.4 (t, 2 H), 5.4 (s, 2 H), 6.2 (d, 1 H), 6.9 (dd, 1 H), 7.1 (d, 1 H), 7.2 (d, 1 H), 7.4 (d, 1 H), 7.6 (d, 1 H), 7.64 (d, 1 H).

Example 26

(5-chlorothiophen-2-ylsulfonyl)-3-(4-(6-fluoro-7-(methylamino)-4-oxo-2H-benzo[e][1,3]oxazin-3(4H)-yl)-2,6-dimethylphenyl)urea

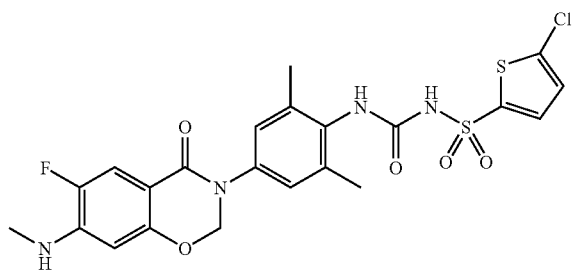

An analogous amide coupling procedure to that described in Ex. 1 was performed on 2-(chlorocarbonyl)-4,5-difluorophenyl acetate (Ex. 1) and 3,5-dimethyl-4-nitrobenzenamine. Ring cyclization was performed using paraformaldehyde as described in Ex 2. Methyl amine displacement of the fluorine was performed analogous to the procedure outlined in Ex. 3. Reduction of the nitro group was effected using the procedure outlined in Ex. 4. Coupling to form the sulfonyl urea was achieved using the DSC method described in Ex. 34 to give 1-(5-chlorothiophen-2-ylsulfonyl)-3-(4-(6-fluoro-7-(methylamino)-4-oxo-2H-benxo[e][1,3]oxazin-3(4H)-yl)-2,6-dimethylphenyl)urea. RP-HPLC: 3.03 min; ES-MS (M+H)$^+$=539; 1H-NMR (MeOH-d$_4$) δ (ppm): 2.17 (s, 6), 2.8 (s, 3), 5.4 (s, 2), 6.2 (d, 1), 6.85 (d, 1), 6.95 (d, 1), 7.3 (d, 1), 7.36 (d, 1).

Example 27

1-(5-chlorothiophen-2-ylsulfonyl)-3-(4-(6-fluoro-7-(methylamino)-4-oxo-2H-benzo[e][1,3]oxazin-3(4H)-yl)-2-methoxyphenyl)urea

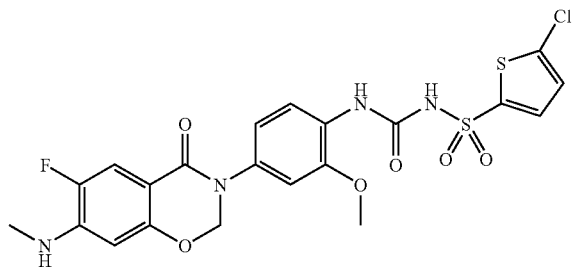

An analogous amide coupling procedure to that described in Ex. 1 was performed on 2-(chlorocarbonyl)-4,5-difluorophenyl acetate (Ex. 1) and 3-methoxy-4-nitrobenzenamine. Ring cyclization was performed using paraformaldehyde as described in Ex 2. Methyl amine displacement of the fluorine was performed analogous to the procedure outlined in Ex. 3. Reduction of the nitro group was effected using the procedure outlined in Ex. 4. Coupling to form the sulfonyl urea was achieved using the method described in Ex. 34 to give 1-(5-chlorothiophen-2-ylsulfonyl)-3-(4-(6-fluoro-7-(methylamino)-4-oxo-2H-benzo[e][1,3]oxazin-3(4H)-yl)-2-methoxyphenyl)urea. RP-HPLC: 3.12 min; ES-MS (M+H)$^+$=540.9; 1H-NMR (DMSO-d$_6$) δ (ppm): 2.8 (s, 3), 3.82 (s, 3), 5.3 (s, 2), 6.2 (d, 1), 6.9 (dd, 1), 7.1 (d, 1), 7.28 (d, 1), 7.3 (d, 1), 7.7 (d, 1), 7.8 (d, 1), 8.4 (s, 1).

Example 28

1-(5-chlorothiophene-2-ylsulfonyl)-3-(4-(6-fluoro-7-(methylamino)-4-oxo-2H-benzo[e][1,3]oxazin-3(4H)-yl)-2-(2-methoxyethoxy)phenyl)urea

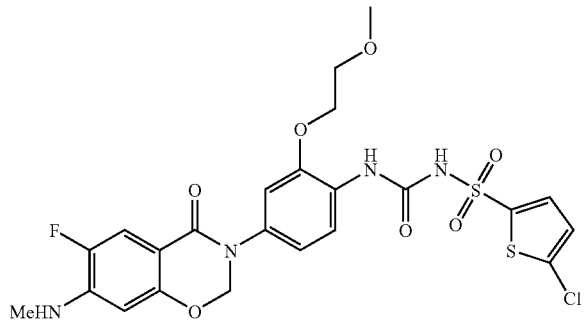

An analogous amide coupling procedure to that described in Ex. 1 was performed on 2-(chlorocarbonyl)-4,5-difluorophenyl acetate (Ex. 1) and 3-(2-methoxyethoxy-4-nitrobenzenamine. Ring cyclization was performed using paraformaldehyde as described in Ex 2. Methyl amine displacement of the fluorine was performed analogous to the procedure outlined in Ex. 3. Reduction of the nitro group was effected using the procedure outlined in Ex. 4. Coupling to form the sulfonyl urea was achieved using the DSC method described in Ex. 34 to give 1-(5-chlorothiophen-2-ylsulfonyl)-3-(4-(6-fluoro-7-(methylamino)-4-oxo-2H-benxo[e][1,3]oxazin-3(4H)-yl)-2-(2-methoxyethoxy)phenyl)urea. RP-HPLC: 3.18 min; ES-MS (M+H)$^+$=585; 1H-NMR (DMSO-d$_6$) δ (ppm): 2.76 (s, 3), 3.40 (s, 3), 3.6 (t, 2), 4.18 (t, 2), 5.5 (s, 2), 6.2 (d, 1), 6.84 (dd, 1), 7.1 (d, 1), 7.28 (d, 1), 7.3 (d, 1), 7.7 (d,1), 7.9 (d, 1), 8.3 (s, 1).

Example 29

N-(4-methoxybenzyl)-4,5-difluoro-2-hydroxybenzamide

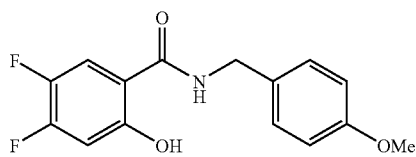

To a solution 4,5-difluoro-2-hydroxybenzoic acid (1 g, 6 mmol, US0061666246) in pyridine (2 mL) was added acetic anhydride (0.8 mL, 7 mol) and the mixture was stirred at room temperature for 2 hr. To this added 10% HCl (10 mL) and extracted the acetate intermediate with ethyl acetate. The ethyl acetate was evaporated and the residue taken up in dichloromethane (10 mL). To this solution added oxalyl chloride (1 mL) and few drops of dimethylformamide and stirred for 1 hr. The solvent was removed and the acid chloride was re-dissolved in dichloromethane (10 mL) and added slowly to dichloromethane solution (10 mL) of p-methoxybenzylamine (0.855 mL, 6.5 mmol). The reaction mixture after 2 hr showed new peak by HPLC and complete disappearance of the starting material. The dichloromethane was removed and the residue dissolved in methanol and to it added 10% aqueous NaOH solution (3 mL) and mixture stirred for 1 hr. The methanol was removed and the residue acidified and extracted with ethyl acetate. The ethyl acetate layer was dried, filtered and evaporated to yield 1.5 g (85%) of N-(4-methoxybenzyl)-4,5-difluoro-2-hydroxybenzamide as a white solid. RP-HPLC: 2.70 min; ES-MS (M+H)$^+$=294; 1H-NMR (CD$_3$OD) δ (ppm) 7.8 (dd, 1), 7.4 (d, 2), 6.8 (d, 2), 6.6 (dd, 1), 4.6 (s, 2), 3.8 (s, 3).

Example 30

3-(4-methoxybenzyl)6,7-difluor-2,3-dihydrobenzo[e][1,3]oxazin-4-one

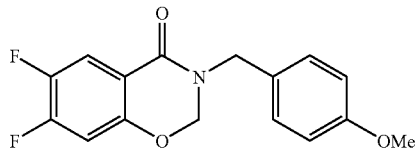

To a toluene solution (25 mL) of N-(4-methoxybenzyl)-4,5-difluoro-2-hydroxybenzamide (1.5 g, 5 mmol) was added paraformaldehyde (0.450 g, 15 mmol) and para-toluenesulfonic acid (0.01 g, 0.05 mmol) and the reaction heated to 110° C. for 3 hr with azeotropic removal of water. Saturated sodium bicarbonate (50 ml) was added and product extracted with ethyl acetate, dried over anhydrous sodium sulfate and concentrated to give 1.3 g (86%) of 3-(4-methoxybenzyl)6,7-difluor-2,3-dihydrobenzo[e][1,3]oxazin-4-one. RP-HPLC: 2.64 min; ES-MS (M+H)$^+$=307.0; 1H-NMR (MeOH-d$_4$) δ (ppm): 7.8 (dd, 1 H), 7.4 (d, 2 H), 6.8 (d, 2 H), 5.1 (s, 2 H), 4.6 (s, 2 H), 3.8 (s, 3 H).

Example 31

3-(4-methoxybenzyl)6-fluoro-7-(methylamino)2,3-dihydrobenzo[e][1,3]oxazin-4-one

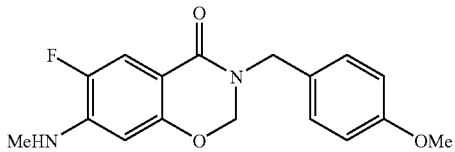

To 3-(4-methoxybenzyl)6,7-difluor-2,3-dihydrobenzo[e][1,3]oxazin-4-one (1.15 g, 3.7 mmol) in dimethyl sulfoxide (10 mL) was added methyl amine (2.5 mL, 5 mmol, 2M solution in tetrahydrofuran) and the reaction heated to 120° C. for 1 hr. Water was added and product extracted with ethyl acetate, dried over anhydrous sodium sulfate and concentrated to give 1 g (85%) of 3-(4-methoxybenzyl)6-fluoro-7-(methylamino)2,3-dihydrobenzo[e][1,3]oxazin-4-one. RP-HPLC: 2.82 min; ES-MS (M+H)$^+$=318.0; 1H-NMR (DMSO-d$_6$) δ (ppm): 7.6 (d, 1), 6.8 (d, 2), 6.4 (d, 1H), 5.0 (s, 2), 4.6 (s, 2), 3.7 (s, 3), 2.8 (s, 3).

Example 32

6-Fluoro-7-(methylamino)-2,3-dihydrobenzo[e][1,3]oxazin-4-one

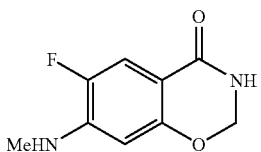

To 3-(4-methoxybenzyl)6-fluoro-7-(methylamino)2,3-dihydrobenzo[e][1,3]oxazin-4-one (1 g, 3.5 mmol) added trifluoroacetic acid ((5 mL) and heated the reaction at 80° C. for 4 hr. RP-HPLC showed formation of new peak and disappearance of SM peak. The trifluoroacetic acid was removed under vacuum and the residue suspended in ethyl acetate and washed with saturated sodium bicarbonate solution. The ethyl acetate was dried, filtered and evaporated to afford 6-Fluoro-7-(methylamino)-2,3-dihydrobenzo[e][1,3]oxazin-4-one as off-white solid (0.500 g, 72%) after triturating with diethyl ether. RP-HPLC: 1.58 min; ES-MS (M+H)$^+$=198.0; 1H-NMR (CDCl$_3$) δ (ppm): 7.5 (d, 1), 6.4 (s, 1), 6.15 (d, 1), 5.17 (s, 2), 2.91 (s, 3)

Example 33

3-(3-(2-(dimethylamino)ethoxy)-4-nitrophenyl)-6-fluoro-7-(methylamino)-2,3-dihydrobenzo[e][1,3]oxazin-4-one

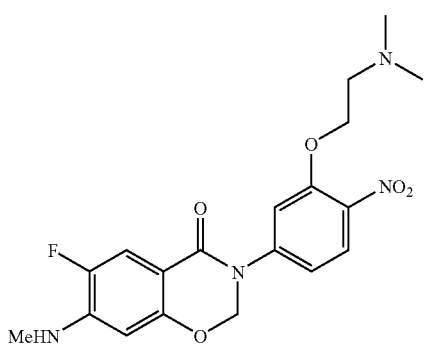

Method A: Using Substituted 4-fluoronitrobenzenes.

To a solution 6-Fluoro-7-(methylamino)-2,3-dihydrobenzo[e][1,3]oxazin-4-one (Ex. 32) (54 mg, 0.27 mmol) and 3-2-(5-fluoro-2-nitrophenoxy)-N,N-dimethylethanamine (67.7 mg, 0.297 mmol, 1.1 eq) in dry dimethylformamide (2 mL) was added powdered cesium carbonate (0.351 g, 1.08 mmol, 4 eq). The mixture was stirred vigorously at 65–70° C. for 5 hr, after cooling added water and extracted the desired product with ethylacetate. This crude residue was purified by flash chromatography to give 70 mg (65%) of pure nitro-aryl product. RP-HPLC: 2.08 min; ES-MS (M+H)$^+$=405;

Example 34

1-(5-chlorothiophene-2-ylsulfonyl)-3-(2-(2-(dimethylamino)ethoxy)-4-(6-fluoro-7-(methylamino)-4-oxo-2H-benzo[e][1,3]oxazin-3-(4H)phenyl)urea

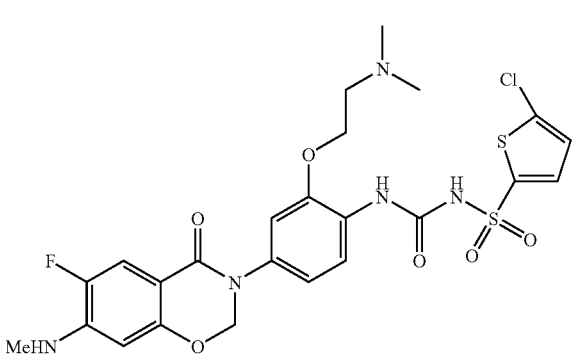

The above nitro intermediate (60 mg, 0.145 mmol) was reduced under catalytic hydrogenation conditions using 1 atm H$_2$, 10% Pd/C (26 mg, 0.024 mmol Pd) in ethyl acetate (2 mL) for 6 hr to give 50 mg (87%) of 3-(4-amino-3-(2-(dimethylamino)ethoxyphenyl)-6-fluor-7-(methylamino)-2,3-dihydrobenzo[e][1,3]oxazin-4-one. ES-MS (M+H)$^+$=375.

To a suspension of 5-chlorothiophene-2-sulfonamide (0.036 g, 0.180 mmol) and N,N'-disuccinimidyl carbonate (DSC, 0.050 g, 0.195 mmol) in dichloromethane (5 mL) was added tetramethylguanidine (TMG, 0.040 mL). The resulting solution was stirred at room temperature for 15 hr. The reaction was concentrated and a solution of 3-(4-amino-3-(2-(dimethylamino)ethoxyphenyl)-6-fluor-7-(methylamino)-2,3-dihydrobenzo[e][1,3]oxazin-4-one (0.055 g, 0.15 mmol) in acetonitrile (3 mL) was added. The resulting solution was stirred at 70° C. for 9 hr. The reaction was diluted with dichloromethane, washed with 0.5 N HCl, dried over sodium sulfate and concentrated to give crude sulfonylurea. This was purified by HPLC (C-18) to give 1-(5-chlorothiophene-2-ylsulfonyl)-3-(2-(2-(dimethylamino)ethoxy)-4-(6-fluoro-7-(methylamino)-4-oxo-2H-benzo[e][1,3]oxazin-3-(4H)phenyl) urea (44 mg, 50%). RP-HPLC: 2.56 min; ES-MS (M+H)$^+$=598; 1H-NMR (MeOH-d$_4$) δ (ppm): 2.82 (s, 6), 2.86 (s, 3), 3.46 (t, 2), 4.4 (t, 2), 5.4 (s, 2), 6.2 (d, 1), 6.9 (dd, 1), 7.1 (d, 1), 7.2 (d, 1), 7.4 (d,1), 7.6 (d, 1), 7.64 (d, 1).

Example 35

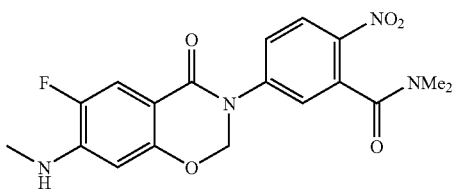

RP-HPLC: 2.02 min; ES-MS (M+H)$^+$=389.0; 1H-NMR (DMSOd$_6$) δ (ppm): 2.76 (d, 3), 2.8 (s, 3), 2.9 (s, 3), 5.7 (s, 2), 6.2 (d, 1), 6.7 (m, 1), 7.3 (d, 1), 7.4 (d, 1), 7.6 (dd, 1), 8.2 (d, 1).

Example 36

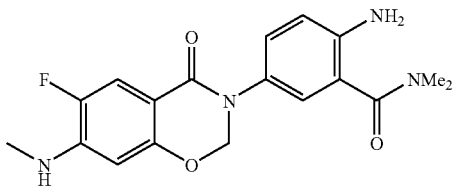

RP-HPLC: 1.59 min; ES-MS (M+H)$^+$=359.0.

Example 37

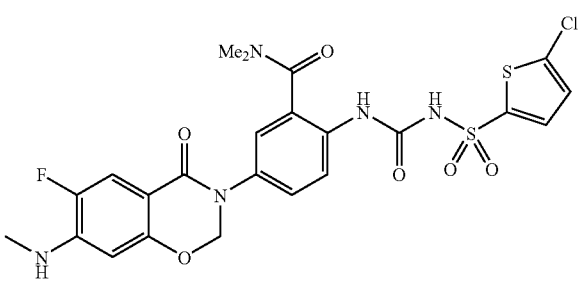

An analogous fluorine displacement procedure to that described in Ex. 33 (Method A) was performed on 6-fluoro- 7-(methylamino)-2,3-dihydrobenzo[e][1,3]oxazin-4-one (Ex. 32) and 5-fluoro-N,N-dimethyl-2-nitrobenzamide. Reduction of the nitro group was effected using the procedure outlined in Ex. 4. Coupling to form the sulfonyl urea was achieved using the method described in Ex. 5 to give 1-(5-chlorothiophen-2-ylsulfonyl)-3-(2-(dimethylcarbamoyl)-4-(6-fluoro-7-(methylamino)-4-oxo-2H-benzo[e][1,3]oxazin-3(4H)-yl)phenyl)urea. RP-HPLC: 2.44 min; ES-MS (M+H)⁺=582.0; 1H-NMR (MeOH-d₄) δ (ppm): 2.8 (s, 3), 2.9 (s, 3), 3.0 (s, 3), 5.5 (s, 2), 6.2 (d, 1), 6.9 (m, 1), 7.2 (d, 1), 7.28 (dd, 1), 7.3 (d, 1), 7.39 (d, 1), 8.0 (d, 1).

Example 38

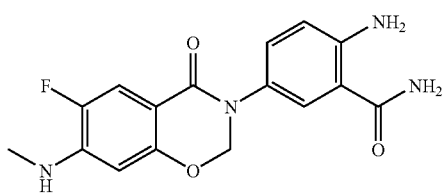

RP-HPLC: 1.4 min; ES-MS (M+H)⁺=331.0

Example 39

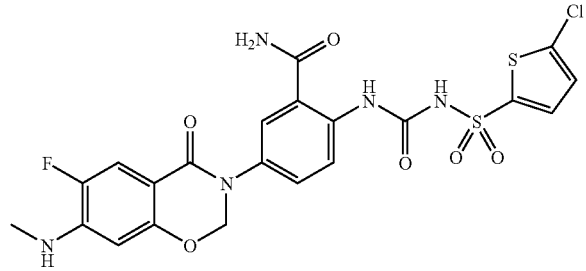

An analogous fluorine displacement procedure to that described in Ex. 33 was performed on 6-fluoro-7-(methylamino)-2,3-dihydrobenzo[e][1,3]oxazin-4-one (Ex. 32) and 5-fluoro-N,N-dimethyl-2-nitrobenzamide. Reduction of the nitro group was effected using the procedure outlined in Ex. 4. Coupling to form the sulfonylurea urea was achieved using the method described in Ex. 5 to give 1-(2-carbamoyl-4-(6-fluoro-7-(methylamino)-4-oxo-2H-benzo[e][1,3]oxazin-3(4H)-yl)phenyl)-3-(5-chlorothiophen-2-ylsulfonyl)urea. RP-HPLC: 2.4 min; ES-MS (M+H)⁺=554.0; 1H-NMR (MeOH-d₄) δ (ppm): 2.8 (s, 3), 5.5 (s, 2), 6.2 (d, 1), 7.1 (d, 1), 7.43 (d, 1), 7.46 (dd, 1), 7.6 (m, 2), 8.2 (d, 1).

Example 40

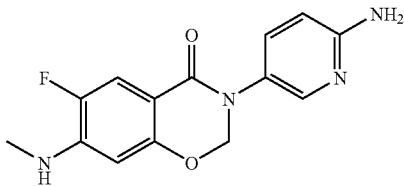

Method B: Using Substituted 4-haloanilines or 5-halo-2-aminopyridines and pyrimidines To 6-fluoro-7-(methylamino)-2,3-dihydrobenzo[e][1,3]oxazin-4-one (0.05 g, 0.25 mmol) and 5-iodopyridin-2-amine (0.067 g, 0.304 mmol) in dioxane (1 ml) was added potassium phosphate (0.08 g, 0.377 mmol). The reaction mixture was degassed for 5 minutes and to this was added trans-diamino cyclohexane (0.004 g, 0.03 mmol) followed by copper (I) iodide (0.006 g, 0.03 mmol) and the mixture heated to 100° C. for 1 hour. Water was added and the product extracted with ethyl acetate (3×10 ml), dried over anhydrous sodium sulfate and concentrated. The product was further purified by reverse phase HPLC (C18) to yield pure 3-(6-aminopyridin-3-yl)-6-fluoro-7-(methylamino)-2,3-dihydrobenzo[e][1,3]oxazin-4-one (0.017 g, 23%). RP-HPLC: 1.5 min; ES-MS (M+H)⁺=289.1; 1H-NMR (MeOH-d₄) δ (ppm): 2.82 (s, 3), 5.4 (s, 2), 6.2 (d, 1), 6.6 (d, 1), 7.3 (d, 1), 7.4 (dd, 1), 7.8 (s, 1).

Example 41

1-(5-chlorothiophen-2-ylsulfonyl)-3-(5-(6-fluoro-7-(methylamino)-4-oxo-2H-benzo[e][1,3]oxazin-3(4H)-yl)pyridin-2-yl)urea

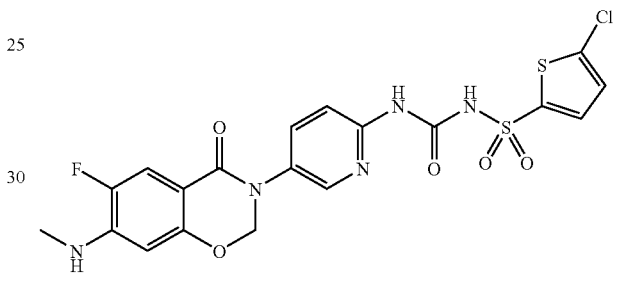

Analogous to the sulfonylurea urea formation described in Ex 5, 3-(6-aminopyridin-3-yl)-6-fluoro-7-(methylamino)-2,3-dihydrobenzo[e][1,3]oxazin-4-one (0.017 g, 0.058 mmol) and (5-Chloro-thiophene-2-sulfonyl)-carbamic acid ethyl ester (0.026 g, 0.096 mmol) were coupled to give 1-(5-chlorothiophen-2-ylsulfonyl)-3-(5-(6-fluoro-7-(methylamino)-4-oxo-2H-benzo[e][1,3]oxazin-3(4H)-yl)pyridin-2-yl)urea (0.007 g, 24%). RP-HPLC: 2.7 min; ES-MS (M+H)⁺=512.0; 1H-NMR (MeOH-d₄) δ (ppm): 2.82 (s, 3), 5.4 (s, 2), 6.2 (d, 1), 6.9 (d, 1), 7.3 (d, 1), 7.6 (dd, 1), 8.0 (d, 1), 8.1 (d, 1).

Example 42

1-(5-chlorothiophen-2-ylsulfonyl)-3-(5-(6-fluoro-7-(methylamino)-4-oxo-2H-benzo [e][1,3]oxazin-3(4H)-yl)-3-methylpyridin-2-yl)urea

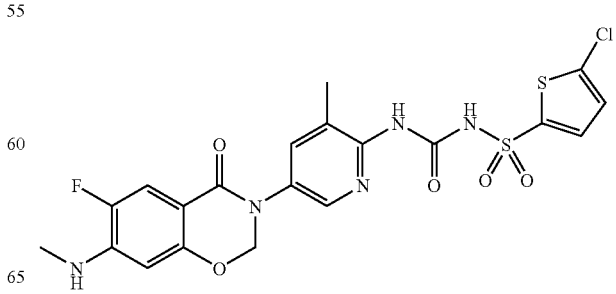

To dioxane (10 mL) was added 5-bromo-3-methylpyridin-2-amine (2 g, 10.6 mmol), sodium iodide (3.2 g, 21.4 mmoL), copper iodide (0.190 g, 1.06 mmol) and the solution degassed followed by addition of tetramethylethane-1,2-diamine (0.803 mL, 1.06 mmol) this mixture heated at 110° C. overnight. After cooling water was added and extracted the crude product with ethyl acetate. The residue was purified by column chromatography to give 5-iodo-3-methylpyridin-2-amine as a beige solid (2.3 g, 93%).

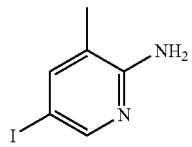

Analogous to the procedure described in Ex. 40, 6-fluoro-7-(methylamino)-2,3-dihydrobenzo[e][1,3]oxazin-4-one (0.100 g, 0.51 mmol) and 5-iodo-3-methylpyridin-2-amine (0.119 g, 0.53 mmol) were coupled to yield pure 3-(6-aminopyridin-3-yl)-6-fluoro-7-(methylamino)-2,3-dihydrobenzo[e][1,3]oxazin-4-one (0.020 g, 13%) after reverse phase HPLC purification. ES-MS (M+H)$^+$=303.

Analogous to the sulfonylurea urea formation described in Ex 5, 3-(6-amino-5-methylpyridin-3-yl)-6-fluoro-7-(methylamino)-2,3-dihydrobenzo[e][1,3]oxazin-4-one (0.010 g, 0.034 mmol) and (5-Chloro-thiophene-2-sulfonyl)-carbamic acid ethyl ester (0.048 g, 0.166 mmol) were coupled to give 1-(5-chlorothiophen-2-ylsulfonyl)-3-(5-(6-fluoro-7-(methylamino)-4-oxo-2H-benzo[e][1,3]oxazin-3(4H)-yl)-3-methylpyridin-2-yl)urea (0.016 g, 85%). RP-HPLC: 2.7 min; ES-MS (M+H)$^+$=526.0; 1H-NMR (DMSO-d$_6$) δ (ppm): 2.2 (s, 3), 2.8 (s, 3), 5.6 (s, 2), 6.2 (d, 1), 6.8 (bs, 1), 7.2 (s, 1), 7.4 (d, 1), 7.6 (s, 1), 7.8 (d, 1), 8.2 (d, 1), 9.6 (bs, 1).

Example 43

1-(5-(6-fluoro-7-(methylamino)-4-oxo-2H-benzo[e][1,3]oxazin-3(4H)-yl)pyridin-2-yl-3-(5-methylthiophen-2-ylsulfonyl)urea

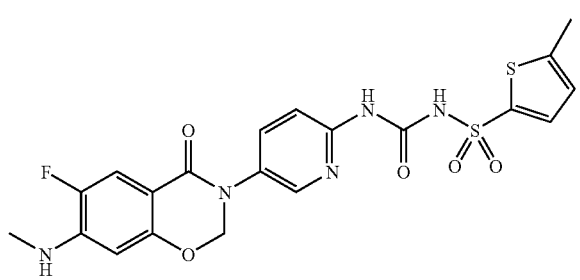

Analogous to the sulfonylurea urea coupling method described in Ex 5, 3-(6-aminopyridin-3-yl)-6-fluoro-7-(methylamino)-2,3-dihydrobenzo[e][1,3]oxazin-4-one was coupled with ethyl 5-methylthiophen-2-ylsulfonylcarbamate to yield 1-(5-(6-fluoro-7-(methylamino)-4-oxo-2H-benzo[e][1,3]oxazin-3(4H)-yl)pyridin-2-yl)-3-(5-methylthiophen-2-ylsulfonyl)urea. RP-HPLC: 2.7 min; ES-MS (M+H)$^+$=492.3; 1H-NMR (MeOH-d$_4$) δ (ppm): 2.5 (s, 3), 2.86 (s, 3), 5.5 (s, 2), 6.2 (d, 1), 6.8 (d, 1), 7.4 (d, 1), 7.46 (d, 1), 7.6 (d, 1), 7.8 (dd, 1), 8.3 (d, 1).

Example 44

1-(5-(6-fluoro-7-(methylamino)-4-oxo-2H-benzo[e][1,3]oxazin-3(4H)-yl)pyridin-2-yl)-3-(5-methoxythiophen-2-ylsulfonyl)urea

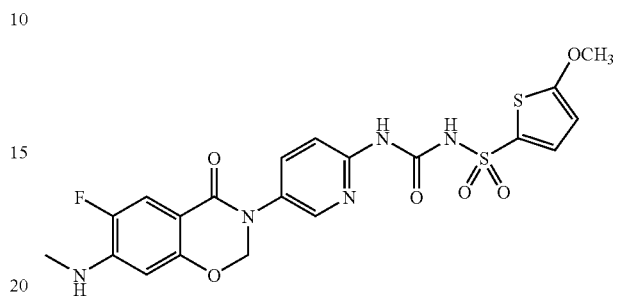

Analogous to the sulfonylurea urea coupling method described in Ex 5, 3-(6-aminopyridin-3-yl)-6-fluoro-7-(methylamino)-2,3-dihydrobenzo[e][1,3]oxazin-4-one was coupled with 3-methoxy-5-methylthiophen-2-ylsulfonylcarbamate to yield 1-(5-(6-fluoro-7-(methylamino)-4-oxo-2H-benzo[e][1,3]oxazin-3(4H)-yl)pyridin-2-yl)-3-(5-methoxythiophen-2-ylsulfonyl)urea. RP-HPLC: 2.7 min; ES-MS (M+H)$^+$=508; 1H-NMR (DMSO-d$_6$) δ (ppm): 2.8 (s, 3), 3.9 (s, 3), 5.6 (s, 2), 6.2 (d, 1), 6.5 (d, 1), 6.7 (d, 1), 7.4 (d, 1), 7.6 (d, 1), 7.8 (d, 1), 8.2 (s, 1), 9.4 (bs, 1).

Example 45

1-(4-(6-fluoro-7-(methylamino)-4-oxo-2H-benzo[e][1,3]oxazin-3(4H)-yl)-3-(5-methoxythiophen-2ylsulfonyl)urea

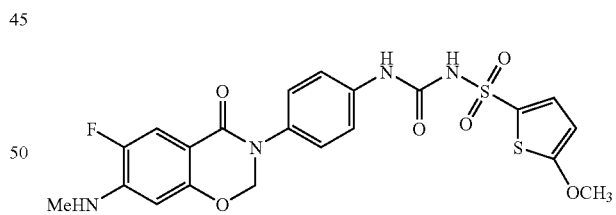

Analogous to the sulfonylurea urea formation described in Ex 34, 5-methoxythiophene-2-sulfonamide was coupled with 3-(4-amino-3-(4-aminophenyl)-6-fluoro-7-(methylamino)-2,3-dihydrobenzo[e][1,3]oxazin-4-one to give crude sulfonylurea. This was purified by HPLC (C-18) to give 1-(4-(6-fluoro-7-(methylamino)-4-oxo-2H-benzo[e][1,3]oxazin-3(4H)-yl)-3-(5-methoxythiophen-2ylsulfonyl)urea (100 mg, 45%). RP-HPLC: 2.77 min; ES-MS (M+H)$^+$=507; 1H-NMR (DMSO-d$_6$) δ (ppm): 2.86 (s, 3), 3.85 (s, 3), 5.5 (s, 2), 6.2 (d, 1), 6.42 (d, 1), 7.24 (d, 1), 7.3 (d, 1), 7.4 (d, 1), 7.4(d, 1), 7.5 (d, 1), 8.98 (s, 1).

Example 46

1-(4-(6-fluoro-7-(methylamino)-4-oxo-2H-benzo[e][1,3]oxazin-3(4H)-yl)-3-5-methylthiophen-2ylsulfonyl)urea

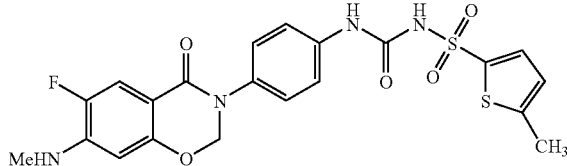

Analogous to the sulfonylurea urea formation described in Ex 5, 3-(4-aminophenyl)-6-fluoro-7-(methylamino)-2,3-dihydrobenzo[e][1,3]oxazin-4-one (Ex. 4) was coupled with 5-methyl-thiophene-2-sulfonyl-carbamic acid ethyl ester to yield 1-(5-methylthiophen-2-ylsulfonyl)-3-(4-(6-fluoro-7-(methylamino)-4-oxo-2H-benzo[e][1,3]oxazin-3(4H)-yl)phenyl)urea. RP-HPLC: 2.49 min; ES-MS $(M+H)^+$ =492.0; 1H-NMR (DMSO-$d_6$) δ (ppm): 2.37 (s, 3), 2.72 (d, 3), 5.4 (s, 2), 6.2 (d, 1), 6.7 (d, 1), 7.01 (dd, 2), 7.15 (d, 1), 7.3 (d, 1), 7.4 (dd, 2), 8.4 (s, 1).

Example 47

5-chloro-4-fluoro-2-hydroxy-N-(4-nitrophenyl)benzamide

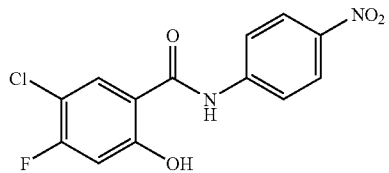

To a solution 4-fluoro-2-hydroxybenzoic acid (1 g, 6.14 mmol, synthesized by a known method from 2,4-difluorobenzoic acid, U.S. Pat. No. 6,166,246) in dioxane (2 mL) was added dichloromethane solution (5 mL) of sulfuryl chloride (2.5 mL, 5 equiv) and the mixture was stirred at room temperature for 24 hr hr. The reaction mixture was diluted with water and collected 4-fluoro-5-chlorosalicylic acid as a white solid (1.2 g, 98%). The solid was suspended in dichloromethane added pyridine (2.5 mL, 5 equiv) followed by acetic anhydride (1.14 mL, 12.07 mmol) and the reaction stirred at room temperature for 1 hr. To this added 10% HCl and extracted the desired acetate with dichloromethane. The dichloromethane was dried (MgSO4), filtered and evaporated to give acetate as a off-white solid To dichloromethane solution (5 mL) of acetate (0.275 g, 1.18 mmol) added oxalyl chloride (0.258 mL, 2.96 mmol) and few drops of dimethylformamide and stirred for 1 hr. The solvent was removed and the acid chloride was re-dissolved in dichloromethane (10 mL) and added slowly to dichloromethane solution (10 mL) of p-nitroaniline (0.163 g, 1.18 mmol). The reaction mixture after 2 hr showed new peak by HPLC and complete disappearance of the starting material. The dichloromethane was removed and the residue (0.300 g, 0.851 mmol) dissolved in methanol and to it added solid potassium carbonate (58 mg, 0.5 eq) and mixture stirred for 1 hr. The methanol was removed and the residue acidified and extracted with ethyl acetate. The ethyl acetate layer was dried, filtered and evaporated to yield 200 mg (77%) of 5-chloro-4-fluoro-2-hydroxy-N-(4-nitrophenyl)benzamide as a tan solid. RP-HPLC: 3.0 min; ES-MS $(M+H)^+$=311.

Example 48

6-chloro-7-fluoro-3-(4-nitrophenyl)-2,3-dihydrobenzo[e][1,3]oxazin-4-one

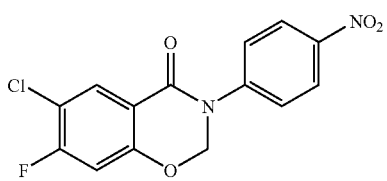

Analogous to ring cyclization procedure in Ex. 2,4-fluoro-5-chloro-2-hydroxy-N-(4-nitrophenyl)benzamide (0.13 g, 0.44 mmol) was treated with paraformadehyde (0.3 g, 10 mmol) and para-toluenesulfonic acid (0.01 g, 0.05 mmol) to give 0.11 mg (81%) of 6-chloro-7-fluoro-3-(4-nitrophenyl)-2,3-dihydrobenzo[e][1,3]oxazin-4-one. RP-HPLC: 2.54 min; ES-MS $(M+H)^+$=307.0; 1H-NMR (MeOH-$d_4$) δ (ppm): 5.84 (s, 2), 7.38 (d, 1), 7.64 (dd, 2), 8.0 (d, 1), 8.27 (d, 2).

Example 49

6-chloro-7-(methylamino)-3-(4-nitrophenyl)-2,3-dihydrobenzo[e][1,3]oxazin-4-one

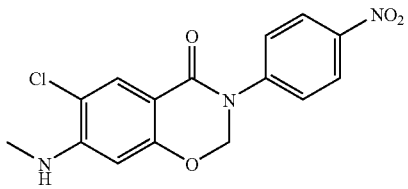

Analogous to Ex. 3, methyl amine displacement was performed using 6-chloro-7-fluoro-3-(4-nitrophenyl)-2,3-dihydrobenzo[e][1,3]oxazin-4-one (0.21 g, 0.16 mmol) and methyl amine (0.3 ml, 2M solution in tetrahydrofuran) to give 0.134 mg (81%) of 6-chloro-7-(methylamino)-3-(4-nitrophenyl)-2,3-dihydrobenzo[e][1,3]oxazin-4-one. RP-HPLC: 2.38 min; ES-MS $(M+H)^+$=334; 1H-NMR (DMSO-$d_6$) δ (ppm): 3.1 (s, 3), 5.73 (s, 2), 6.2 (d, 1), 7.38 (d, 1), 7.61 (d, 2), 8.2 (d, 2).

Example 50

3-(4-aminophenyl)-6-chloro-7-(methylamino)-2,3-dihydrobenzo[e][1,3]oxazin-4-one

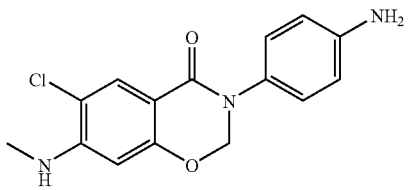

To a suspension of 6-chloro-7-(methylamino)-3-(4-nitrophenyl)-2,3-dihydrobenzo[e][1,3]oxazin-4-one (0.108 g, 0.33 mmol) in ethyl acetate (6 mL) under Ar was added 10% Pt(S)/C (0.04 g). The mixture was hydrogenated under 1 atm H2 overnight, filtered through celite and concentrated to give 0.096 g (98%) of 3-(4-aminophenyl)-6-fluoro-7-(methylamino)-2,3-dihydrobenzo[e][1,3]oxazin-4-one.
RP-HPLC: 1.50 min; ES-MS (M+H)$^+$=304; 1H-NMR (MeOH-d$_4$) δ (ppm): 2.8 (s, 3), 5.5 (s, 2), 6.2 (d, 1), 7.2 (d, 2), 7.3 (d, 2), 7.4 (d, 1).

Example 51

1-(5-chlorothiophen-2-ylsulfonyl)-3-(4-(6-chloro-7-(methylamino)-4-oxo-2H-benzo[e][1,3]oxazin-3(4H)-yl)phenyl)urea

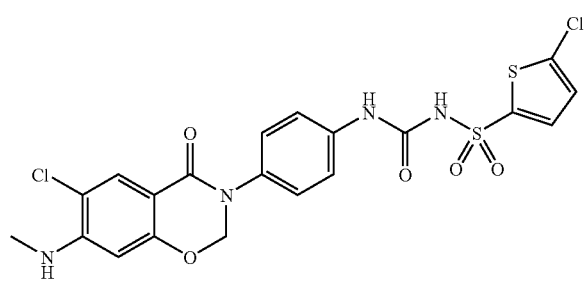

Analogues to the sulfonylurea formation described in Ex. 5, 3-(4-aminophenyl)-6-chloro-7-(methylamino)-2,3-dihydrobenzo[e][1,3]oxazin-4-one (Ex. 47) (44 mg, 0.15 mmol) and (5-Chloro-thiophene-2-sulfonyl)-carbamic acid ethyl ester (59 mg, 0.22 mmol) were coupled to give 1-(5-chlorothiophen-2-ylsulfonyl)-3-(4-(6-chloro-7-(methylamino)-4-oxo-2H-benzo[e][1,3]oxazin-3(4H)-yl)phenyl) urea. RP-HPLC: 2.70 min; ES-MS (M+H)$^+$=528.0; 1H-NMR (MeOH-d$_4$) δ (ppm): 2.8 (s, 3), 5.4 (s, 2), 6.2 (s, 1), 6.9 (d, 1), 7.1 (d, 2), 7.39 (d, 1), 7.48 (d, 2), 7.7 (s, 1).

Example 52

4-(4,5-difluoro-2-hydroxybenzamido)benzoate

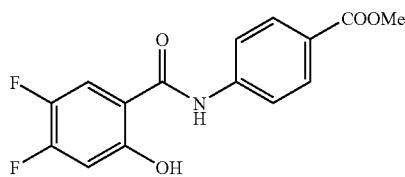

Analogous to the method described in Example 1, 2-(chlorocarbonyl)-4,5-difluorophenyl acetate (0.2 g, 0.85 mmol) and methyl 4-aminobenzoate (0.174 g, 1.1 mmol) were coupled to yield methyl 4-(4,5-difluoro-2-hydroxybenzamido)benzoate (0.186 g, 64%). RP-HPLC: 2.61 min; ES-MS (M+H)$^+$=308.0.

Example 53

Methyl 4-(6,7-difluoro-4-oxo-2H-benzo[e][1,3]oxazin-3(4H)-yl) benzoate

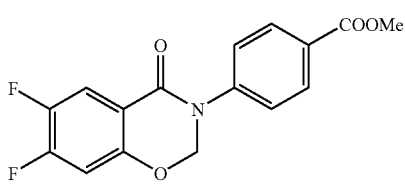

Analogous to the method described in Ex 2, 4-(4,5-difluoro-2-hydroxybenzamido) benzoate (0.08 g, 0.25 mmol) and paraformaldehyde (0.250 g, 9 mmol) were reacted to give methyl 4-(6,7-difluoro-4-oxo-2H-benzo[e][1,3] oxazin-3(4H)-yl) benzoate (0.078 g, 93%). RP-HPLC: 2.5 min; ES-MS (M+H)$^+$=320.0; 1H-NMR (MeOH-d$_4$) δ (ppm): 3.9 (s, 3), 5.7 (s, 2), 7.1 (dd, 1), 7.5 (d, 2), 7.8 (dd, 1), 8.1 (d, 2).

Example 54

Methyl 4-(6-fluoro-7-(methylamino)-4-oxo-2H-benzo[e][1,3]oxazin-3(4H)-yl)benzoate

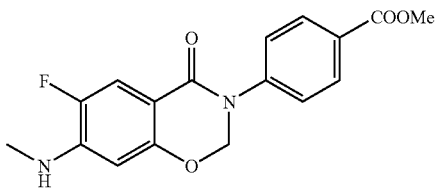

Analogous to the method described in Ex 3, 4-(6,7-difluoro-4-oxo-2H-benzo[e][1,3]oxazin-3(4H)-yl)benzoate (0.1 g, 0.31 mmol) was reacted with methylamine (0.8 ml, 2M in THF, 1.2 mmol) to give methyl 4-(6-fluoro-7-(methylamino)-4-oxo-2H-benzo[e][1,3]oxazin-3(4H)-yl)benzoate (0.092 g, 88%). RP-HPLC: 2.3 min; ES-MS (M+H)$^+$=331.0; 1H-NMR (MeOH-d$_4$) δ (ppm): 2.8 (s, 3), 3.9 (s, 3), 5.6 (s, 2), 6.27 (d, 1), 7.4 (d, 1), 7.5 (d, 2), 8.1 (d, 2).

Example 55

4-(6-fluoro-7-(methylamino)-4-oxo-2H-benzo[e][1,3]oxazin-3(4H)-yl)benzoic acid

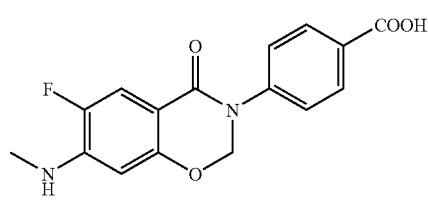

To methyl 4-(6-fluoro-7-(methylamino)-4-oxo-2H-benzo[e][1,3]oxazin-3(4H)-yl)benzoate (0.05 g, 0.15 mmol) was dissolved in dioxan (2 ml) and to it was added sodium hydroxide (0.012 g, 0.3 mmol) in water (0.5 ml) and the mixture stirred for 4 hr at room temperature. The solvent was removed under vacuum and the residue acidified, extracted with ethyl acetate (2×10 ml), dried over anhydrous sodium sulfate and concentrated to provide 4-(6-fluoro-7-(methylamino)-4-oxo-2H-benzo[e][1,3]oxazin-3(4H)-yl)benzoic acid (0.2 g, 41%). RP-HPLC: 1.8 min; ES-MS (M+H)$^+$=317.0.

Example 56

N-(5-chlorothiophen-2-ylsulfonyl)-4-(6-fluoro-7-(methylamino)-4-oxo-2H-benzo[e][1,3]oxazin-3(4H)-yl) benzamide

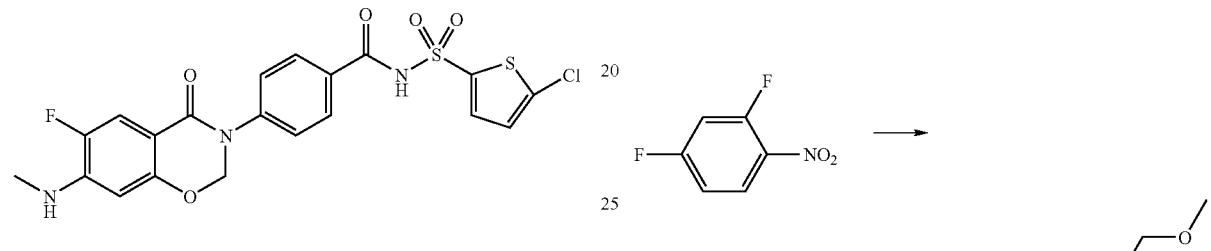

To 4-(6-fluoro-7-(methylamino)-4-oxo-2H-benzo[e][1,3]oxazin-3(4H)-yl)benzoic acid (0.02 g, 0.063 mmol) in methylene chloride (2 ml) was added 1-[3-(dimethylamino)propyl]-3-ethylcarbodiimide hydrochloride (0.013 g, 0.068 mmol), N,N-dimethylpyridin-4-amine (0.008 g, 0.068 mmol) followed by 5-chlorothiophene-2-sulfonamide (0.014 g, 0.07 mmol) and the mixture stirred at room temperature for 8 hr. The solvent was removed and the product purified on HPLC (C18) to give N-(5-chlorothiophen-2-ylsulfonyl)-4-(6-fluoro-7-(methylamino)-4-oxo-2H-benzo[e] [1,3] oxazin-3(4H)-yl) benzamide (0.05 g, 15%). RP-HPLC: 2.58 min; ES-MS (M+H)$^+$=496.0; 1H-NMR (MeOH-d$_4$) δ (ppm): 2.8 (s, 3), 5.6 (s, 2), 6.2 (d, 1), 7.1 (d, 1), 7.3 (d, 1), 7.4 (d, 2), 7.7 (d, 1), 7.9 (d, 2).

Example 57

N-(5-chlorothiophen-2-ylsulfonyl)-2-fluoro-4-(6-fluoro-7-(methylamino)-4-oxo-2H-benzo[e][1,3]oxazin-3(4H)-yl) benzamide

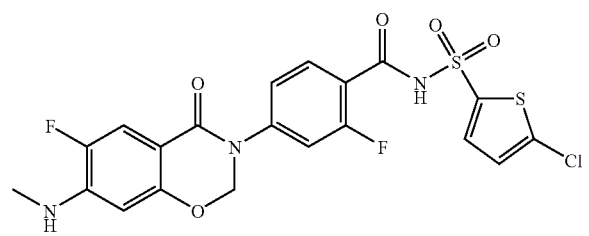

Analogous to the method described in Ex 1, 2-(chlorocarbonyl)-4,5-difluorophenyl acetate (0.2 g, 0.85 mmol) and methyl-2-fluoro-4-aminobenzoate (0.174 g, 1.1 mmol) were coupled to yield methyl 4-(4,5-difluoro-2-hydroxybenzamido)-2-fluorobenzoate (0.186 g, 64%). RP-HPLC: 2.61 min; ES-MS (M+H)$^+$=326.0. This intermediate was cyclized with formaldehyde, followed by displacement of 7-fluoro with methylamine analogues to method above to give methyl 4-(6-fluoro-7-methylamino-4-oxo-2H-benzo[e][1,3]oxazin-3(4H)benzoate. The methyl ester was hydrolyzed as described in Ex. 55 and then which was coupled with 5-chlorothiophene-2-sulfonamide as described in Ex. 56. The solvent was removed and the product purified on HPLC (C18) to give N-(5-chlorothiophen-2-ylsulfonyl)2-fluoro-4-(6-fluoro-7-(methylamino)-4-oxo-2H-benzo[e] [1,3] oxazin-3(4H)-yl) benzamide (0.005 g, 15%). RP-HPLC: 2.78 min; ES-MS (M+H)$^+$=514; 1H-NMR (MeOH-d$_4$) δ (ppm): 2.8 (s, 3), 5.6 (s, 2), 6.2 (d, 1), 7.1 (d, 1), 7.3 (d, 1), 7.4 (dd, 1), 7.5 (dd, 1), 7.7 (dd, 1), 7.9 (dd, 1).

Example 58

3-(2-methoxyethoxy)-4-nitrobenzenamine

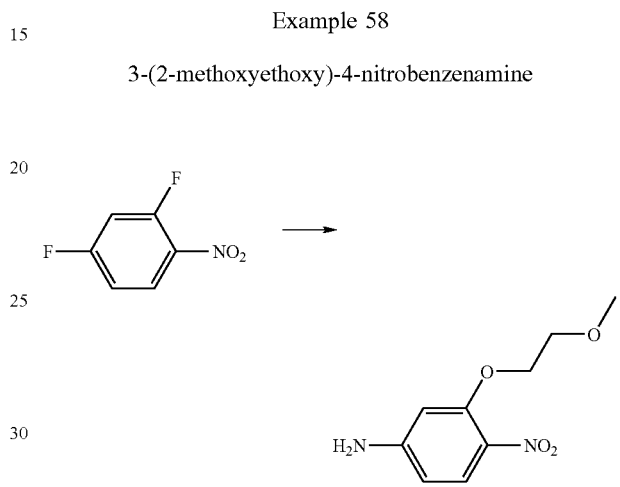

To a solution of 2-methoxy-ethanol in 4 ml dry THF, was added tert-butoxide (378 mg, 3.37 mmol) at 0° C. The resulting mixture was added dropwise to the solution of 2,4-difluoro-1-nitro-benzene (536 mg, 3.37 mmol) in 5 ml dry THF at 0° C. The mixture was stirred at 0° C. for 30 minutes, then diluted with ethyl acetate and washed with brine. The organic layers were combined and concentrated in vacuo to give 4-Fluoro-2-(2-methoxy-ethoxy)-1-nitro-benzene. 4-Fluoro-2-(2-methoxy-ethoxy)-1-nitro-benzene (1.35 g, 6.3 mmol) was treated with p-methoxybenzylamine (1.64 mL, 12.6 mmol) in dimethyl sulfoxide at 80° C. in a sealed tube for 4 hr. After work up with ethyl acetate and water isolated N-(4-methoxybenzyl)3-(2-methoxyethoxy)-4-nitrobenzenamine intermediate. RP-HPLC: 2.13 min; ES-MS (M+H)$^+$=346; To this intermediate added trifluoroacetic acid and heated the reaction mixture at 80° C. for 1 hr to deprotect the p-methoxybenzyl functionality to give final product 3-(2-methoxyethoxy)-4-nitobenzenamine. RP-HPLC: 1.14 min; ES-MS (M+H)$^+$=213; 1H-NMR (MeOH-d$_4$) δ (ppm): 3.4 (s, 3 H), 3.8 (t, 2 H), 4.10 (t, 2 H), 6.2 (dd, 1 H), 6.26 (d, 1 H), 7.76 (d, 1 H).

Example 59

2-(5-fluoro-2-nitrophenoxy)-N,N-dimethylethanamine

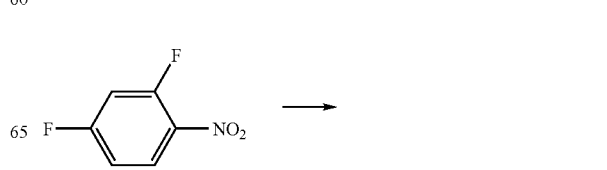

*-continued*

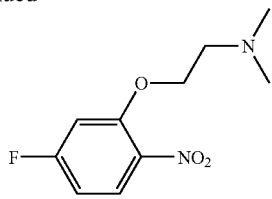

2-(5-fluoro-2-nitrophenoxy)-N,N-dimethylethanamine was obtained from 2-dimethylamino-ethanol using the procedure described in Ex. 58. RP-HPLC: 1.37 min; ES-MS (M+H)$^+$=229; 1H-NMR (MeOH-d$_4$) δ (ppm): 2.19 (s, 3 H), 2.61 (t, 2 H), 4.2 (t, 2 H), 6.95 (ddd, 1 H), 7.34 (dd, 1 H), 7.98 (dd, 1 H).

Example 60

Pharmacological Assays

The pharmacological activity of each of the compounds according to the invention is determined by the following in vitro assays:

I. Inhibition of ADP-Mediated Platelet Aggregation in vitro

The effect of testing the compound according to the invention on ADP-induced human platelet aggregation is preferably assessed in 96-well microtiter assay (see generally the procedures in Jantzen, H. M. et al. (1999) *Thromb. Hemost.* 81:111–117). Human venous blood is collected from healthy, drug-free volunteers into ACD (85 mM sodium citrate, 111 mM glucose, 71.4 mM citric acid) containing PGI$_2$ (1.25 ml ACD containing 1.6 µM PGI$_2$/10 ml blood; PGI$_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730×g and resuspending the platelet pellet in CGS (13 mM sodium citrate, 30 mM glucose, 120 mM NaCl; 2 ml CGS/10 ml original blood volume) containing 1 U/ml apyrase (grade V, Sigma, St. Louis, Mo.). After incubation at 37° C. for 15 minutes, the platelets are collected by centrifugation at 730×g for 10 minutes and resuspended at a concentration of 3×10$^8$ platelets/ml in Hepes-Tyrode's buffer (10 mM Hepes, 138 mM NaCl, 5.5 mM glucose, 2.9 mM KCl, 12 mM NaHCO$_3$, pH 7.4) containing 0.1% bovine serum albumin, 1 mM CaCl$_2$ and 1 mM MgCl$_2$. This platelet suspension is kept >45 minutes at 37° C. before use in aggregation assays.

Inhibition of ADP-dependent aggregation is preferably determined in 96-well flat-bottom microtiter plates using a microtiter plate shaker and plate reader similar to the procedure described by Frantantoni et al., *Am. J. Clin. Pathol.* 94, 613 (1990). All steps are performed at room temperature. The total reaction volume of 0.2 ml/well includes in Hepes-Tyrodes buffer/0.1% BSA: 4.5×10$^7$ apyrase-washed platelets, 0.5 mg/ml human fibrinogen (American Diagnostica, Inc., Greenwich, Conn.), serial dilutions of test compounds (buffer for control wells) in 0.6% DMSO. After about 5 minutes preincubation at room temperature, ADP is added to a final concentration of 2 µM which induces submaximal aggregation. Buffer is added instead of ADP to one set of control wells (ADP$^-$ control). The OD of the samples is then determined at 490 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 490 nm at t=5 minutes compared to t=0 minutes and is expressed as % of the decrease in the ADP control samples after correcting for changes in the unaggregated control samples.

II. Inhibition of [$^3$H]2-MeS-ADP Binding to Platelets

Having first determined that the compounds according to the invention inhibit ADP-dependent platelet aggregation with the above assay, a second assay is used to determine whether such inhibition is mediated by interaction with platelet ADP receptors. Utilizing the second assay the potency of inhibition of such compounds with respect to [$^3$H]2-MeS-ADP binding to whole platelets is determined. [$^3$H]2-MeS-ADP binding experiments are routinely performed with outdated human platelets collected by standard procedures at hospital blood banks. Apyrase-washed outdated platelets are prepared as follows (all steps at room temperature, if not indicated otherwise):

Outdated platelet suspensions are diluted with 1 volume of CGS and platelets pelleted by centrifugation at 1900×g for 45 minutes. Platelet pellets are resuspended at 3-6×10$^9$ platelets/ml in CGS containing 1 U/ml apyrase (grade V, Sigma, St. Louis, Mo.) and incubated for 15 minutes at 37° C. After centrifugation at 730×g for 20 minutes, pellets are resuspended in Hepes-Tyrode's buffer containing 0.1% BSA (Sigma, St. Louis, Mo.) at a concentration of 6.66×10$^8$ platelets/ml. Binding experiments are performed after >45 minutes resting of the platelets.

Alternatively, binding experiments are performed with fresh human platelets prepared as described in I. (Inhibition of ADP-Mediated Platelet Aggregation in vitro), except that platelets are resuspended in Hepes-Tyrode's buffer containing 0.1% BSA (Sigma, St. Louis, Mo.) at a concentration of 6.66×10$^8$ platelets/ml. Very similar results are obtained with fresh and outdated platelets.

A platelet ADP receptor binding assay using the tritiated potent agonist ligand [$^3$H]2-MeS-ADP (Jantzen, H. M. et al. (1999) Thromb. Hemost. 81:111–117) has been adapted to the 96-well microtiter format. In an assay volume of 0.2 ml Hepes-Tyrode's buffer with 0.1% BSA and 0.6% DMSO, 1×10$^8$ apyrase-washed platelets are preincubated in 96-well flat bottom microtiter plates for 5 minutes with serial dilutions of test compounds before addition of 1 nM [$^3$H]2-MeS-ADP ([$^3$H]2-methylthioadenosine-5'-diphosphate, ammonium salt; specific activity 48–49 Ci/mmole, obtained by custom synthesis from Amersham Life Science, Inc., Arlington Heights, Ill., or NEN Life Science Products, Boston, Mass.). Total binding is determined in the absence of test compounds. Samples for nonspecific binding may contain 10$^{-5}$ M unlabelled 2-MeS-ADP (RBI, Natick, Mass.). After incubation for 15 minutes at room temperature, unbound radioligand is separated by rapid filtration and two washes with cold (4–8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glassfiber filtermats (Printed Filtermat A, for 1450 Microbeta, Wallac Inc., Gaithersburg, Md.). The platelet-bound radioactivity on the filtermats is determined in a scintillation counter (Microbeta 1450, Wallac Inc., Gaithersburg, Md.). Specific binding is determined by subtraction-specific binding from total binding, and specific binding in the presence of test compounds is expressed as % of specific binding in the absence of test compounds dilutions.

TABLE 1

ACTIVITY OF THE SYNTHESIZED
COMPOUNDS IN ARB and PRP ASSAYS
In the table below, activity in the PRP assay is provided as
follows: +++, $IC_{50} < 10$ µM; ++, $10$ µM $< IC_{50} < 30$ µM; and +,
$IC_{50} > 30$ µM. Activity in the ARB assay is provided
as follows: +++, $IC_{50} < 0.05$ µM; ++, $0.05$ µM $<$
$IC_{50} < 0.5$ µM; and +, $IC_{50} > 0.5$ µM.

| Example | ARB (µM) | PRP (µM) |
|---|---|---|
| 5 | +++ | +++ |
| 10 | ++ | ++ |
| 15 | +++ | +++ |
| 20 | + | ND |
| 25 | + | ND |
| 26 | +++ | +++ |
| 27 | +++ | + |
| 28 | +++ | +++ |
| 34 | ++ | ++ |
| 37 | ++ | ND |
| 39 | +++ | +++ |
| 41 | +++ | +++ |
| 42 | +++ | +++ |
| 43 | +++ | +++ |
| 44 | ++ | + |
| 45 | +++ | + |
| 46 | +++ | ++ |
| 51 | +++ | + |
| 56 | +++ | +++ |
| 57 | +++ | + |

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound having the formula:

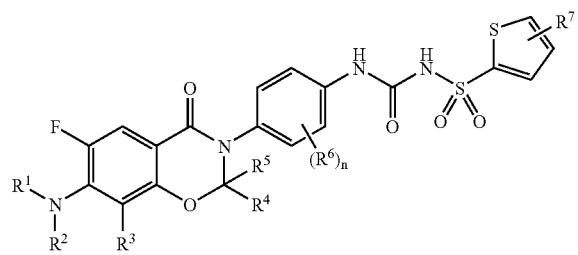

wherein
  $R^1$ is a member selected from the group consisting of $C_{1-6}$ alkyl, $C_{1-6}$ haloalkyl, $C_{3-5}$ cycloalkyl, $C_{3-5}$ cycloalkyl-alkyl, benzyl, and substituted benzyl;
  $R^2$ is a member selected from the group consisting of H, and $C_{1-6}$ alkyl;
  $R^3$ is a member selected from the group consisting of H, $C_{1-6}$ alkyl, $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, halogen, cyano and —C(O)$R^{3a}$, wherein $R^{3a}$ is a member selected from the group consisting of H, hydroxy, $C_{1-6}$ alkyl, $C_{1-6}$ alkoxy, amino, $C_{1-6}$ alkylamino and di-$C_{1-6}$ alkylamino;
  $R^4$ is a member selected from the group consisting of H and $C_{1-6}$ alkyl;
  $R^5$ is a member selected from the group consisting of H, $C_{1-6}$ alkyl, $C_{1-6}$ haloalkyl, benzyl, aryl, $C_{1-6}$ alkyl-N—$(R^{5a})_2$; $C_{1-6}$ alkyl-O—$(R^{5a})$; wherein each $R^{5a}$ is a member independently selected from the group consisting of H, $C_{1-6}$ alkyl, and optionally, two $R^{5a}$ groups attached to nitrogen are combined with the nitrogen atom to form an azetidine, pyrrolidine, piperidine or morpholine ring;
  Ar is an aromatic ring selected from the group consisting of benzene, pyridine, pyrazine and pyrimidine, each of which is optionally substituted with from 1–2 $R^6$ substituents,
    wherein each $R^6$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl-alkoxy, amino, $C_{1-6}$ alkylamino, di-$C_{1-6}$ alkylamino, —C(=N$R^{6a}$)—N($R^{6b}$)$_2$, —C(O)$R^{6a}$, —O(CH$_2$)$_m$OR$^{6b}$, —(CH$_2$)$_m$OR$^{6b}$, —O(CH$_2$)$_m$N($R^{6b}$)$_2$ and —(CH$_2$)$_m$N($R^{6b}$)$_2$,
      wherein each subscript m is independently an integer of from 1 to 3, each $R^{6a}$ is a member independently selected from the group consisting of H, hydroxy, $C_{1-6}$ alkyl, $C_{1-6}$ alkoxy, amino, $C_{1-6}$ alkylamino and di-$C_{1-6}$ alkylamino, and each $R^{6b}$ is a member independently selected from the group consisting of H, $C_{1-4}$ alkyl and $C_{1-4}$ alkanoyl, and optionally, two $R^{6b}$ groups attached to nitrogen are combined with the nitrogen atom to form an azetidine, pyrrolidine, piperidine or morpholine ring;
  L is a linking group selected from the group consisting of a bond and —NH—;
  $R^7$ is a member selected from the group consisting of H, halogen, cyano, $C_{1-6}$ alkyl, $C_{2-6}$ alkenyl, $C_{2-6}$ alkynyl, $C_{1-6}$ alkoxy and $C_{1-6}$ haloalkyl;
and pharmaceutically acceptable salts thereof.

2. A compound of claim 1, having the formula:

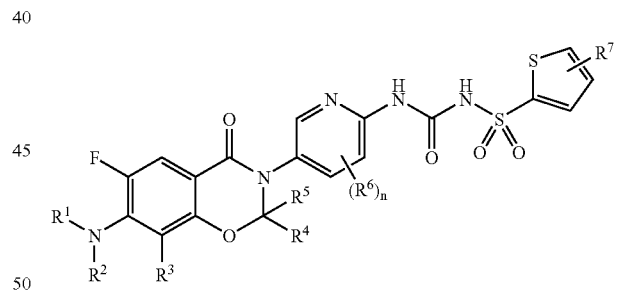

wherein the subscript n is an integer of from 0 to 2.

3. A compound of claim 1, having the formula:

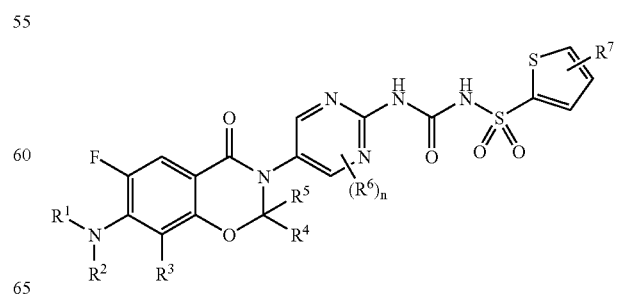

wherein the subscript n is an integer of from 0 to 2.

4. A compound of claim 1, having the formula:

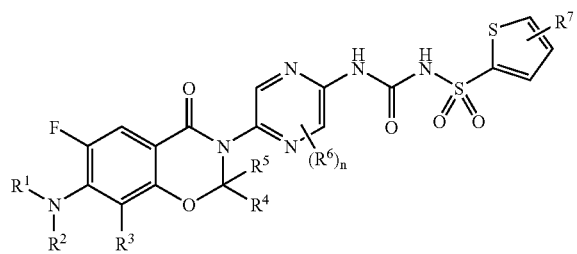

wherein the subscript n is an integer of from 0 to 2.

5. A compound of claim 1, having the formula:

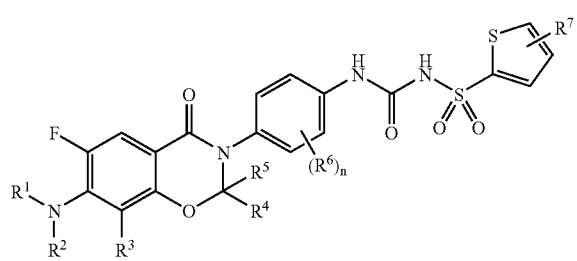

wherein the subscript n is an integer of from 0 to 2.

6. A compound of claim 2, wherein n is 0 or 1; $R^1$ is $C_{1-4}$ alkyl, $C_{3-5}$ cycloalkyl, $C_{3-5}$ cycloalkyl-alkyl, or halosubstituted benzyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is H or $C_{1-4}$ alkyl, $C_{1-4}$ haloalkyl, —CN, —C≡CH or —CONH$_2$; $R^6$, when present is selected from the group consisting of halogen, $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl; $R^7$ is H, $C_{1-4}$ alkyl or halogen.

7. A compound of claim 6, wherein $R^1$ is $C_{1-4}$ alkyl; $R^4$ is H or CH$_3$; $R^5$ is H or CH$_3$; $R^6$, when present is selected from the group consisting of halogen, $C_{1-4}$ alkyl, $C_{1-4}$ alkoxy; $R^7$ is halogen or $C_{1-4}$ alkyl.

8. A compound of claim 7, wherein $R^1$ is methyl; $R^4$ is H; $R^5$ is H or CH$_3$; $R^7$ is chloro, and is attached at the 5-position of the thienyl ring; n is 0 or 1, and $R^6$ when present is selected from the group consisting of halogen, $C_{1-4}$ alkyl, —OCH$_2$CH$_2$OH, —OCH$_2$CH$_2$OCH$_3$, —OCH$_2$OCH$_3$, —OCH$_2$CH$_2$OC(O)CH$_3$ and —O(CH$_2$)$_2$N(CH$_3$)$_2$.

9. A compound of claim 1, having the formula:

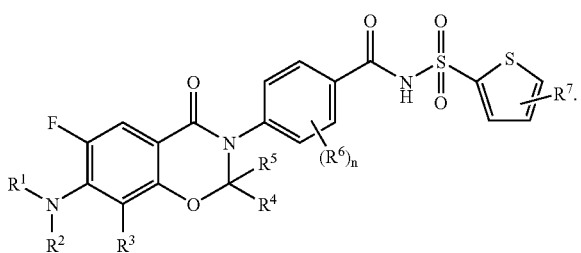

10. A compound of claim 1, selected from the group consisting of:

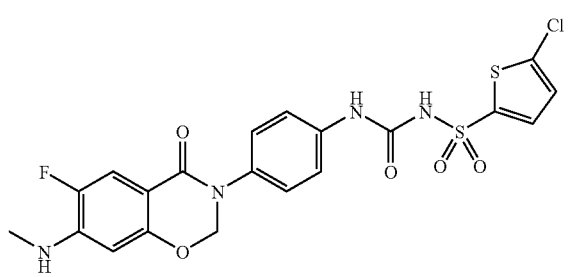

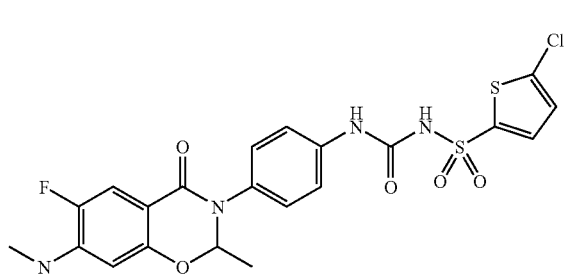

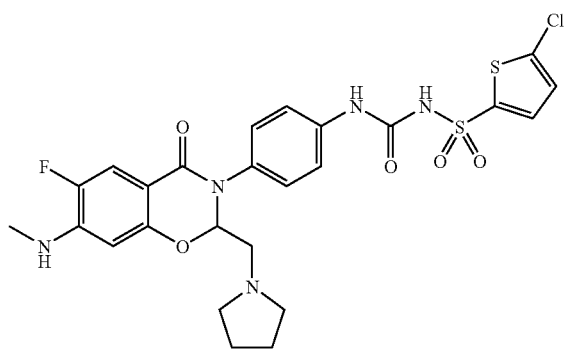

-continued
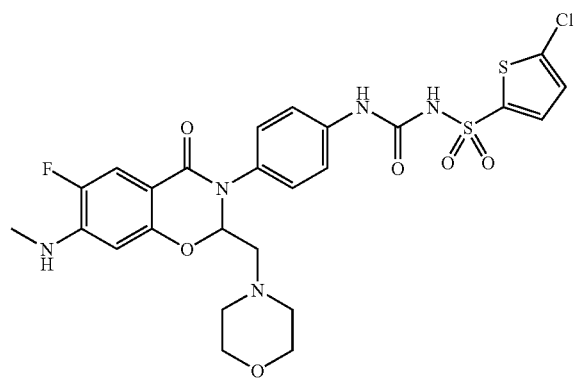
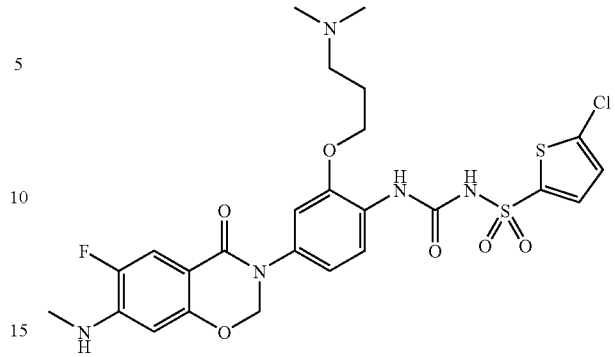
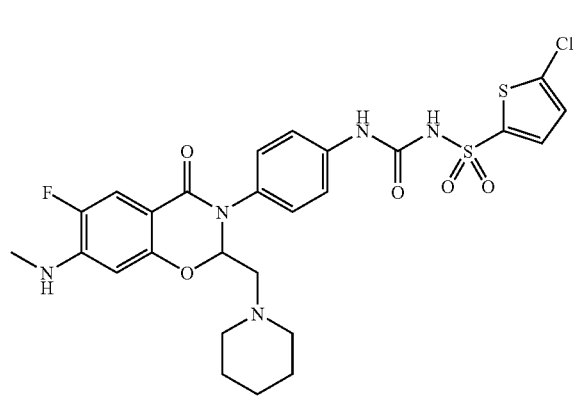
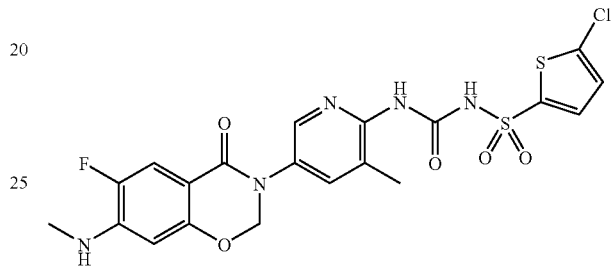
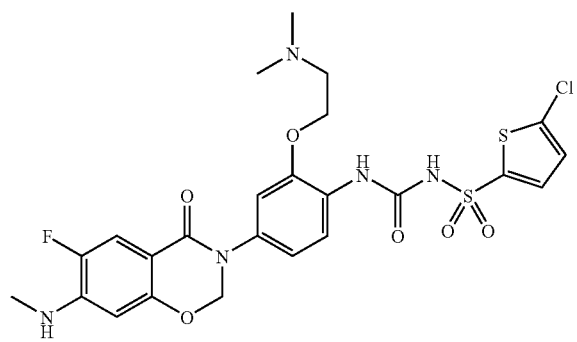
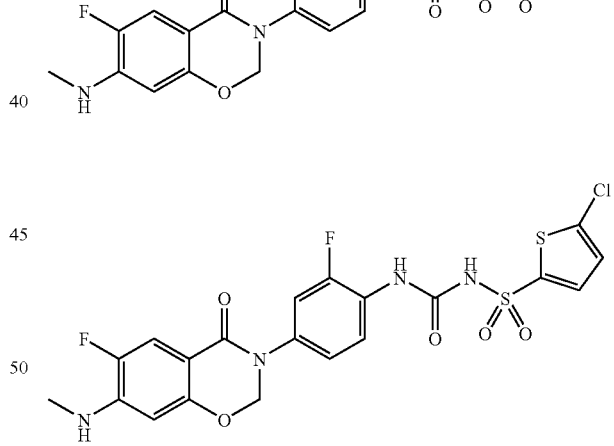
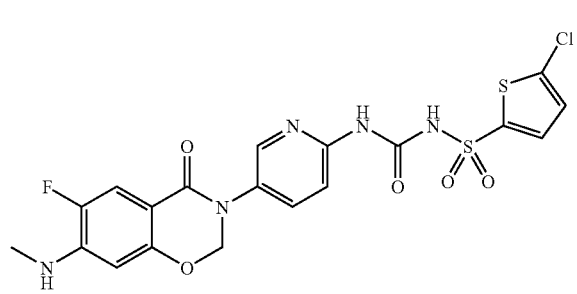
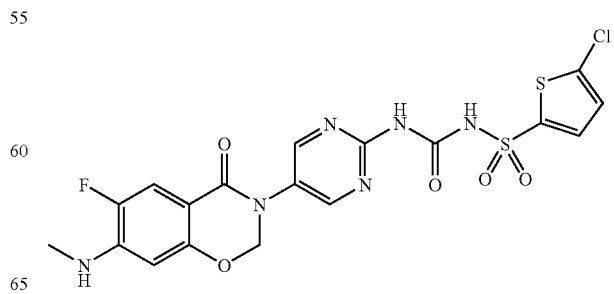

57
-continued
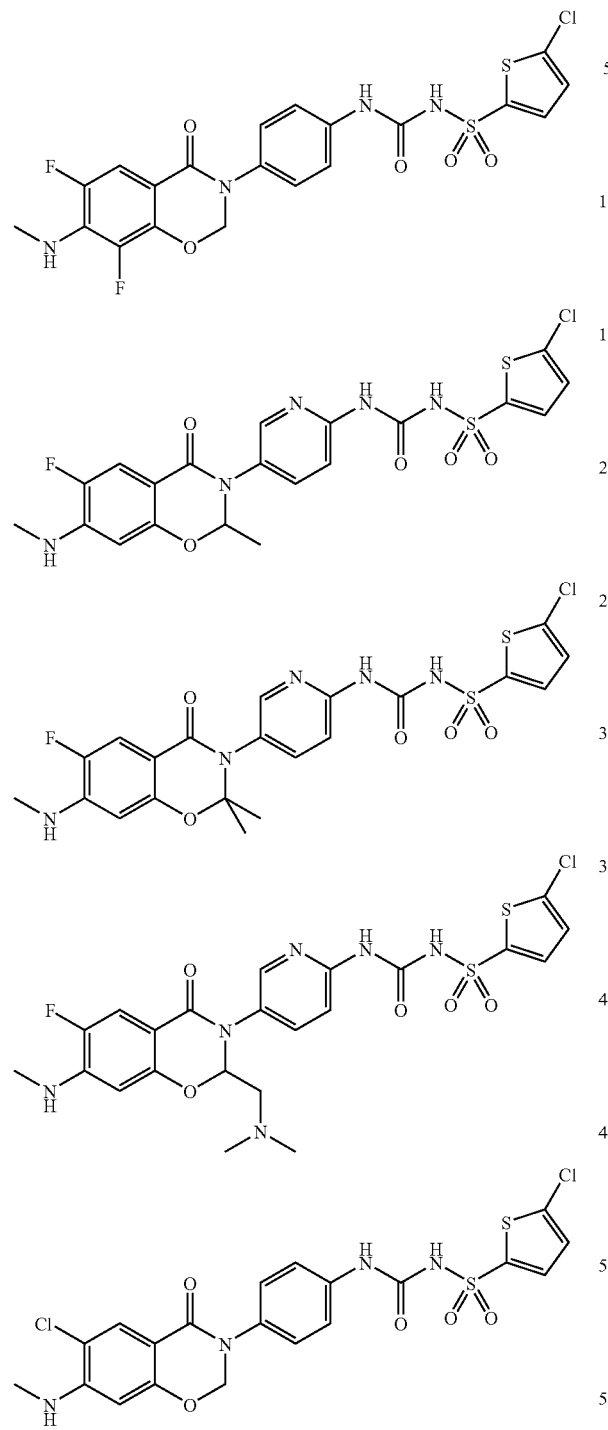
58
-continued
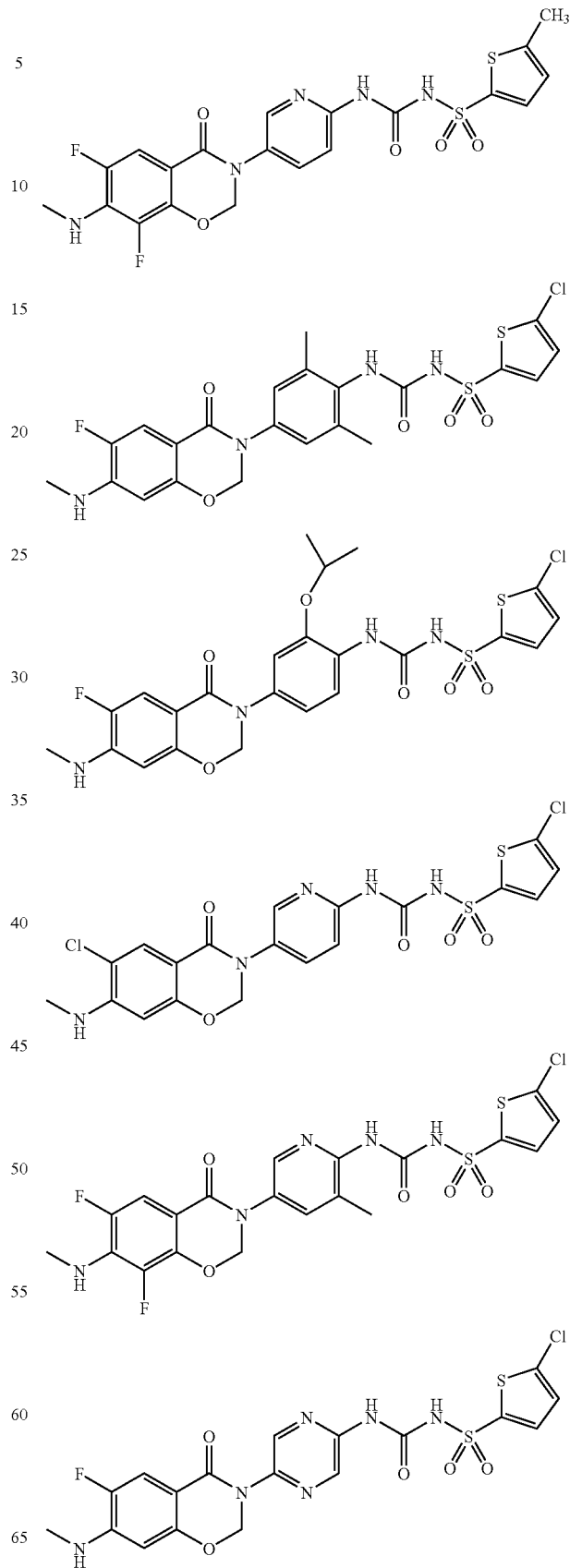

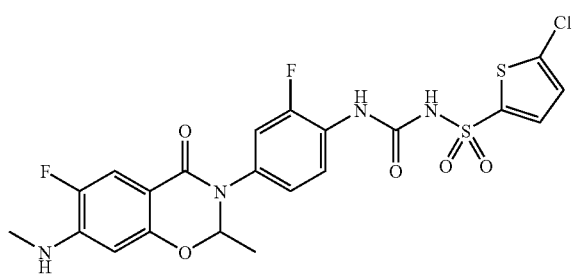
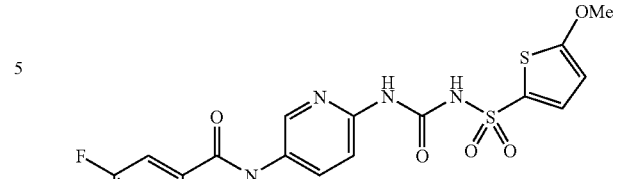
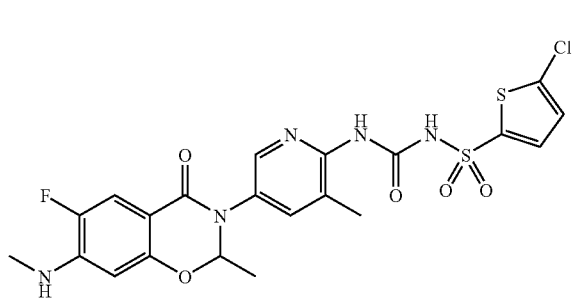
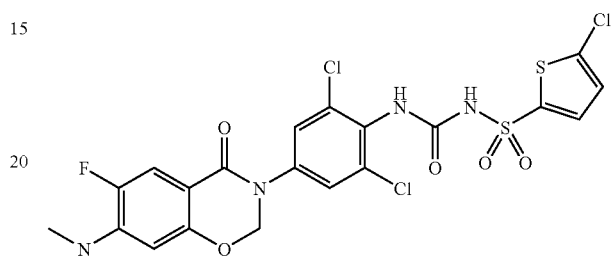
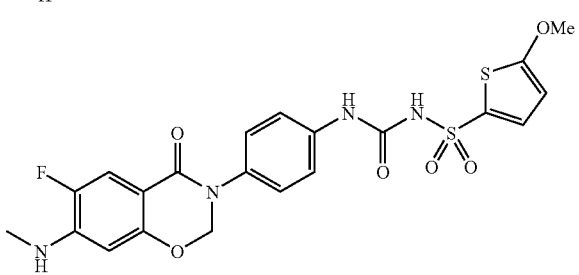
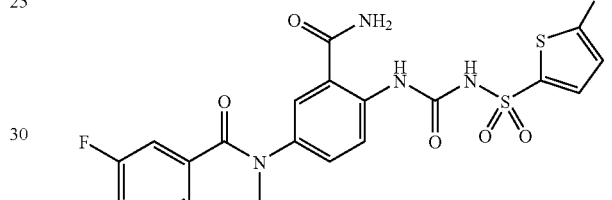
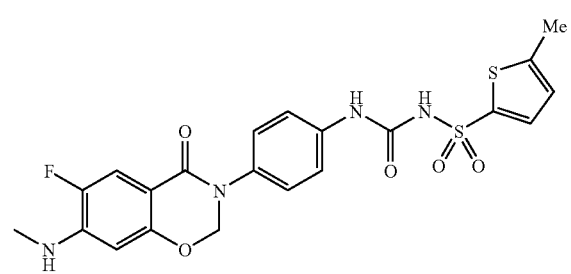
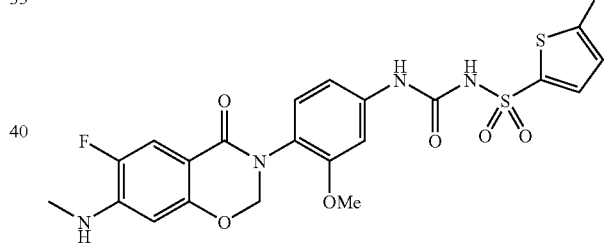
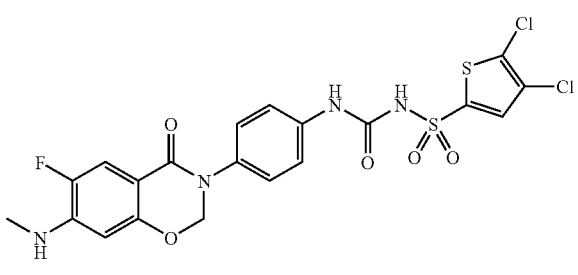
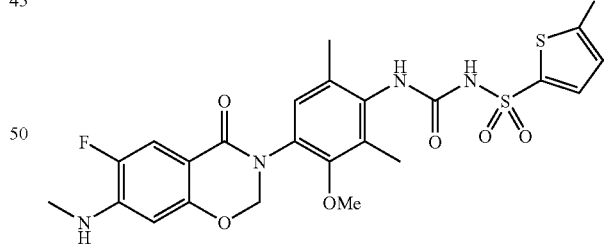
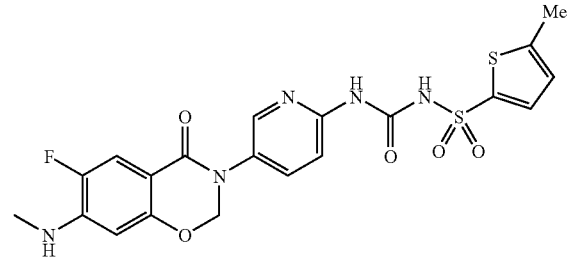
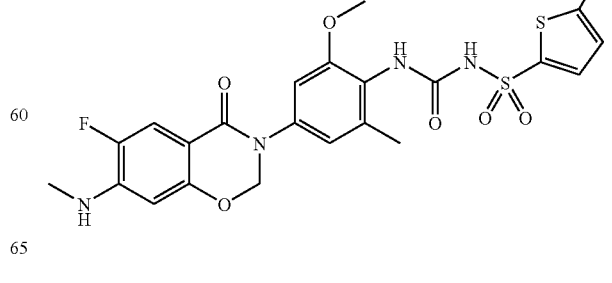

-continued

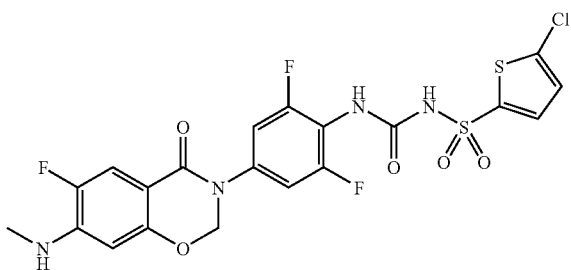

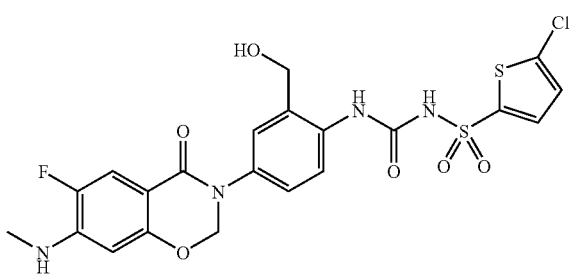

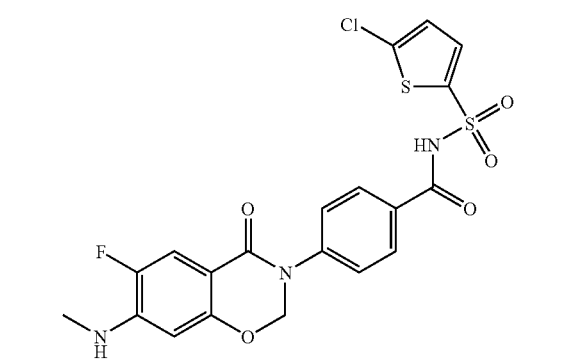

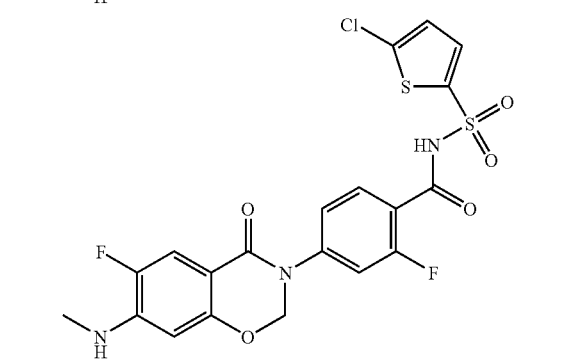

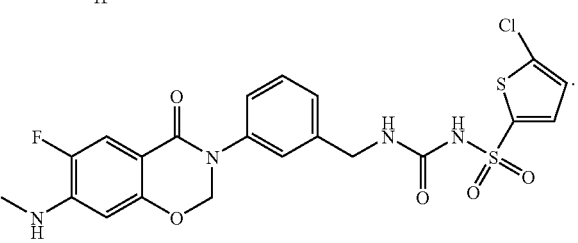

11. A pharmaceutical composition comprising a pharmaceutically acceptable carrier and a compound having the formula:

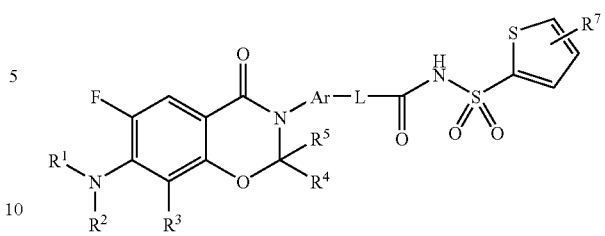

or a pharmaceutically acceptable salt thereof, wherein
$R^1$ is a member selected from the group consisting of $C_{1-6}$ alkyl, $C_{1-6}$ haloalkyl, $C_{3-5}$ cycloalkyl, $C_{3-5}$ cycloalkyl-alkyl, benzyl, and substituted benzyl;
$R^2$ is a member selected from the group consisting of H, and $C_{1-6}$ alkyl;
$R^3$ is a member selected from the group consisting of H, $C_{1-6}$ alky $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, halogen, cyano and —C(O)$R^{3a}$, wherein $R^{3a}$ is a member selected from the group consisting of H, hydroxy, $C_{1-6}$ alkyl, $C_{1-6}$ alkoxy, amino, $C_{1-6}$ alkylamino and di-$C_{1-6}$ alkylamino;
$R^4$ is a member selected from the group consisting of H and $C_{1-6}$ alkyl;
$R^5$ is a member selected from the group consisting of H, $C_{1-6}$ alkyl, $C_{1-6}$ haloalkyl, benzyl, aryl, $C_{1-6}$ alkyl-N—($R^{5a}$)$_2$; $C_{1-6}$ alkyl-O—($R^{5a}$); wherein each $R^{5a}$ is a member independently selected from the group consisting of H, $C_{1-6}$ alkyl, and optionally, two $R^{5a}$ groups attached to nitrogen are combined with the nitrogen atom to form an azetidine, pyrrolidine, piperidine or morpholine ring;
Ar is an aromatic ring selected from the group consisting of benzene, pyridine, pyrazine and pyrimidine, each of which is optionally substituted with from 1–2 $R^6$ substituents,
wherein each $R^6$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl-alkoxy, amino, $C_{1-6}$ alkylamino, di-$C_{1-6}$ alkylamino, —C(=N$R^{6a}$)—N($R^{6b}$)$_2$, —C(O)$R^{6a}$, —O(CH$_2$)$_m$ O$R^{6b}$, —(CH$_2$)$_m$O$R^{6b}$, —O(CH$_2$)$_m$N($R^{6b}$)$_2$ and —(CH$_2$)$_m$N($R^{6b}$)$_2$,
wherein each subscript m is independently an integer of from 1 to 3, each $R^{6a}$ is a member independently selected from the group consisting of H, hydroxy, $C_{1-6}$ alkyl, $C_{1-6}$ alkoxy, amino, $C_{1-6}$ alkylamino and di-$C_{1-6}$ alkylamino, and each $R^{6b}$ is a member independently selected from the group consisting of H, $C_{1-4}$ alkyl and $C_{1-4}$ alkanoyl, and optionally, two $R^{6b}$ groups attached to nitrogen are combined with the nitrogen atom to form an azetidine, pyrrolidine, piperidine or morpholine ring;
L is a linking group selected from the group consisting of a bond and —NH—;
$R^7$ is a member selected from the group consisting of H, halogen, cyano, $C_{1-6}$ alkyl, $C_{2-6}$ alkenyl, $C_{2-6}$ alkynyl, $C_{1-6}$ alkoxy and $C_{1-6}$ haloalkyl;
and pharmaceutically acceptable salts thereof.

12. A pharmaceutical composition of claim 11, wherein said compound has a formula selected from the group consisting of:

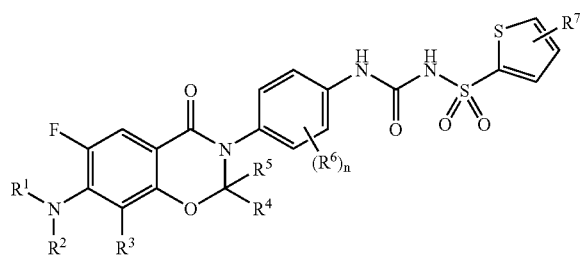

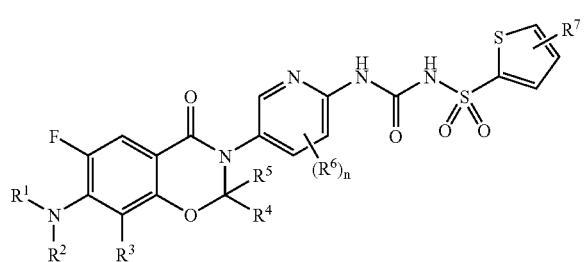

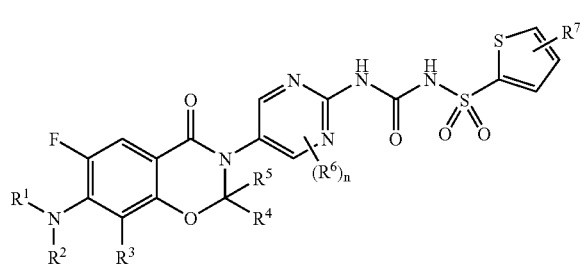

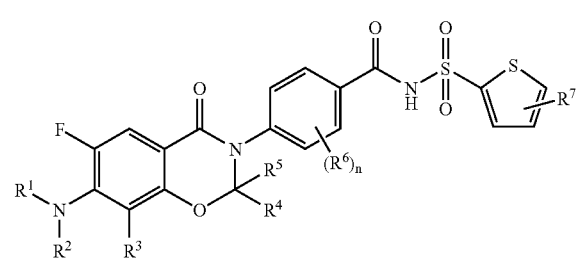

wherein subscript n is an integer from 0 to 2.

13. A pharmaceutical composition as in claim 12, wherein subscript n is 0 or 1; $R^1$ is $C_{1-4}$ alkyl, $C_{3-5}$ cycloalkyl, $C_{3-5}$ cycloalkyl-alkyl, or halosubstituted benzyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is H or $C_{1-4}$ alkyl, $C_{1-4}$ haloalkyl, —CN, —C≡CH or —CONH$_2$; $R^6$, when present is selected from the group consisting of halogen, $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl; $R^7$ is H, $C_{1-4}$ alkyl or halogen.

14. A pharmaceutical composition of claim 13, wherein $R^1$ is $C_{1-4}$ alkyl; $R^4$ is H or CH$_3$; $R^5$ is H or CH$_3$; $R^6$, when present is selected from the group consisting of halogen, $C_{1-4}$ alkyl, $C_{1-4}$ alkoxy; $R^7$ is halogen or $C_{1-4}$ alkyl.

15. A pharmaceutical composition of claim 14, wherein $R^1$ is methyl; $R^4$ is H; $R^5$ is H or CH$_3$; $R^7$ is chloro, and is attached at the 5-position of the thienyl ring; n is 0 or 1, and $R^6$ when present is selected from the group consisting of halogen, $C_{1-4}$ alkyl, —OCH$_2$CH$_2$OH, —OCH$_2$CH$_2$OCH$_3$, —OCH$_2$OCH$_3$, —OCH$_2$CH$_2$OC(O)CH$_3$ and —O(CH$_2$)$_2$N(CH$_3$)$_2$.

16. A pharmaceutical composition of claim 11, wherein said compound is selected from the group consisting of:

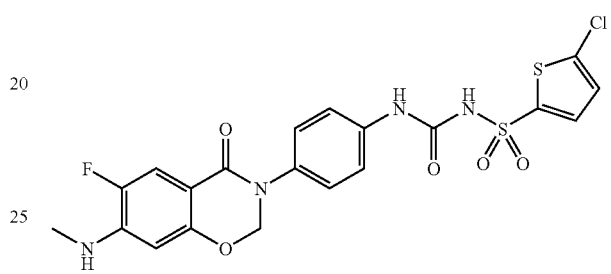

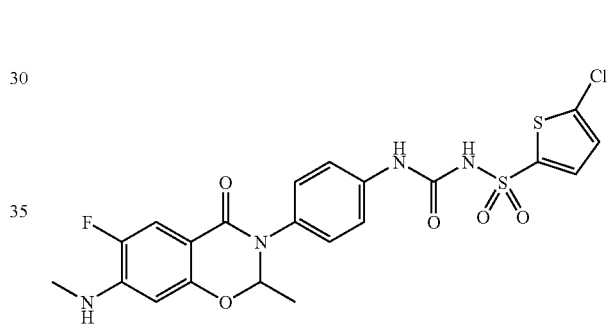

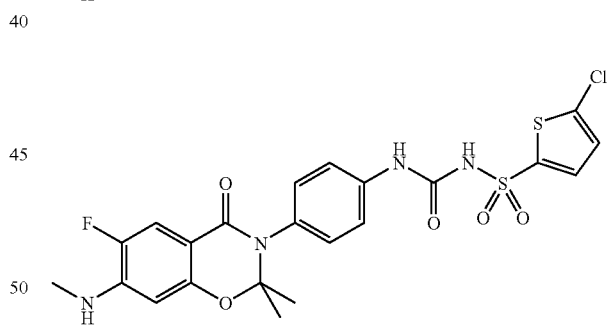

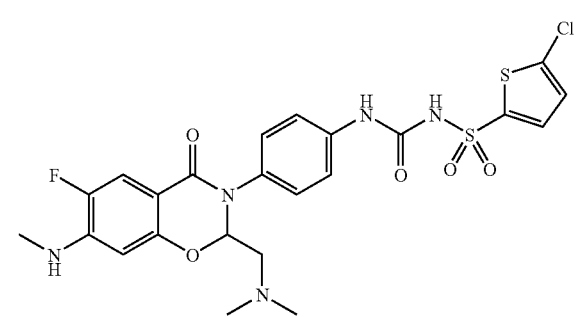

-continued
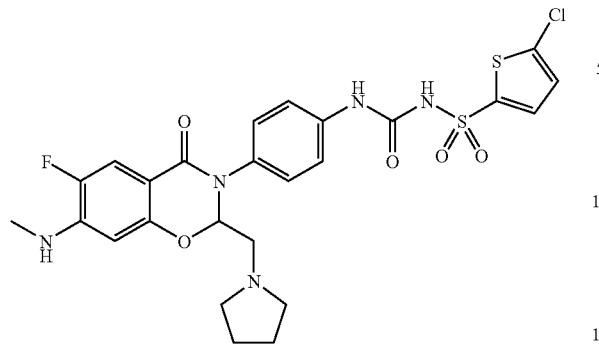
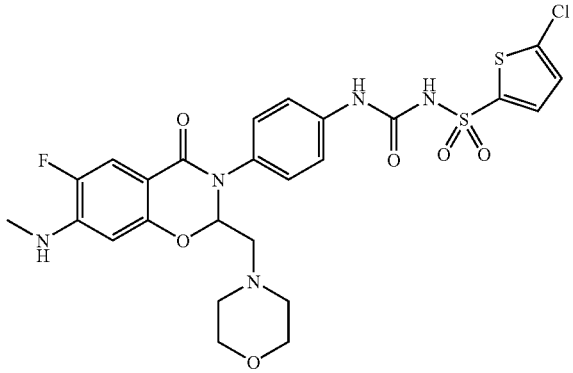
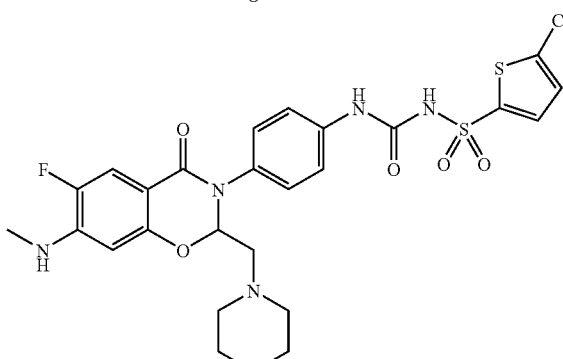
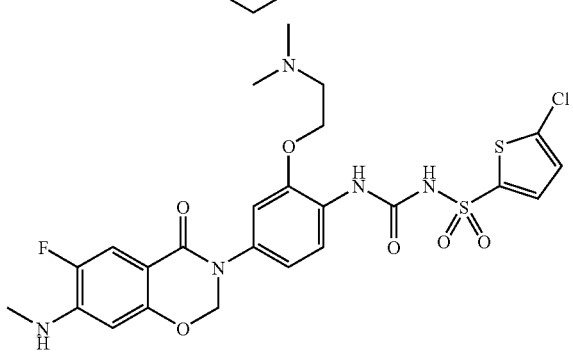
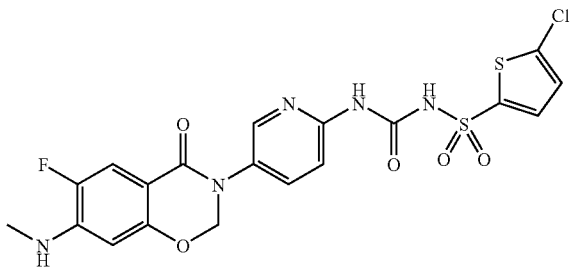
-continued
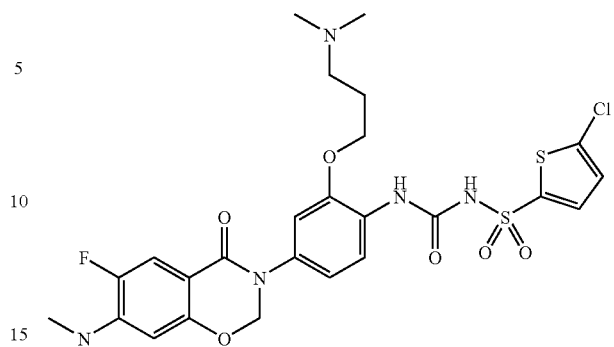
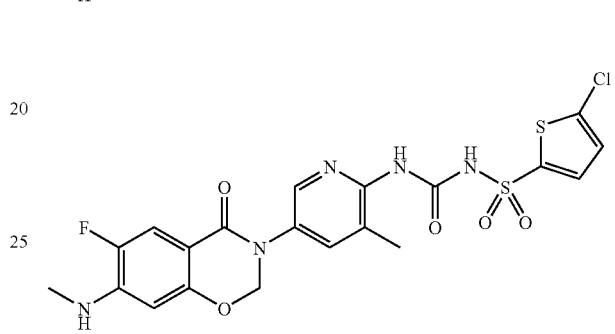
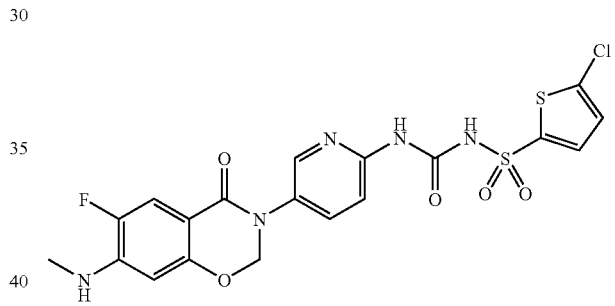
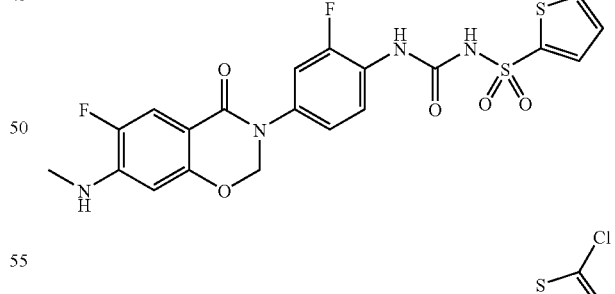
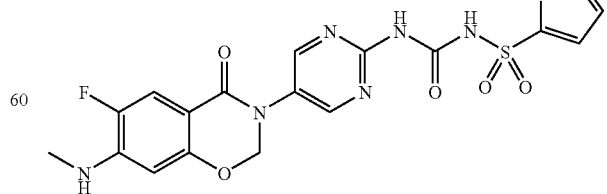

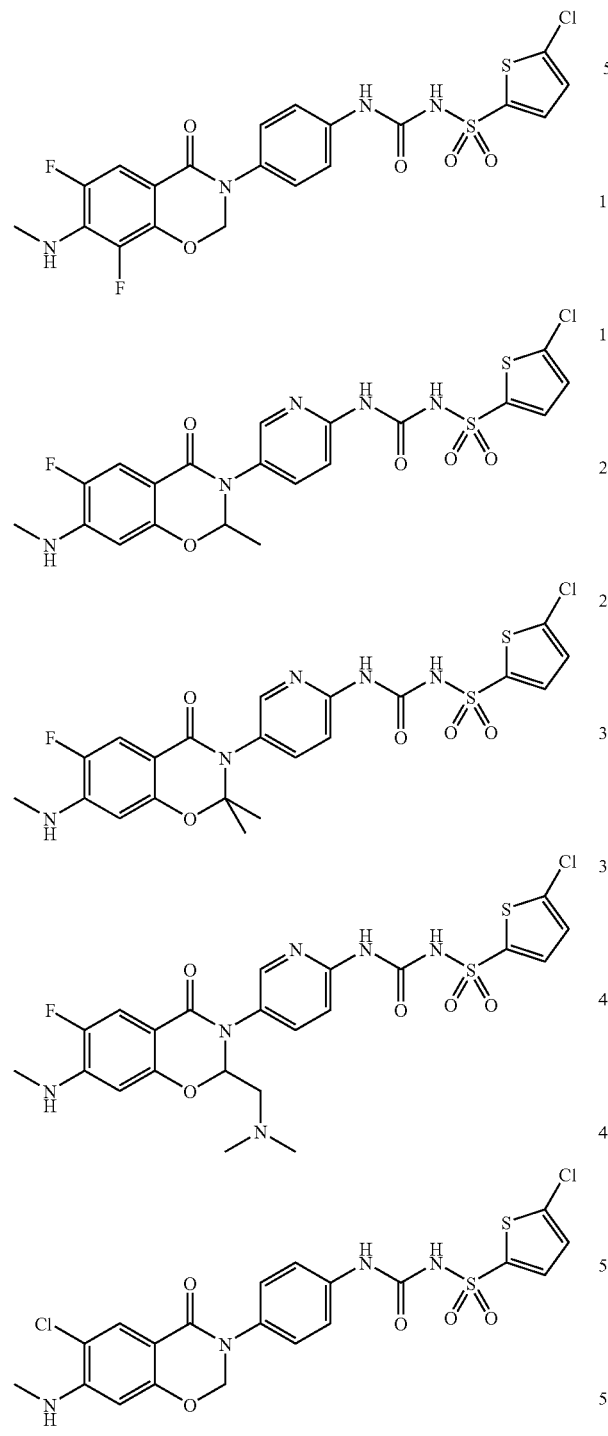
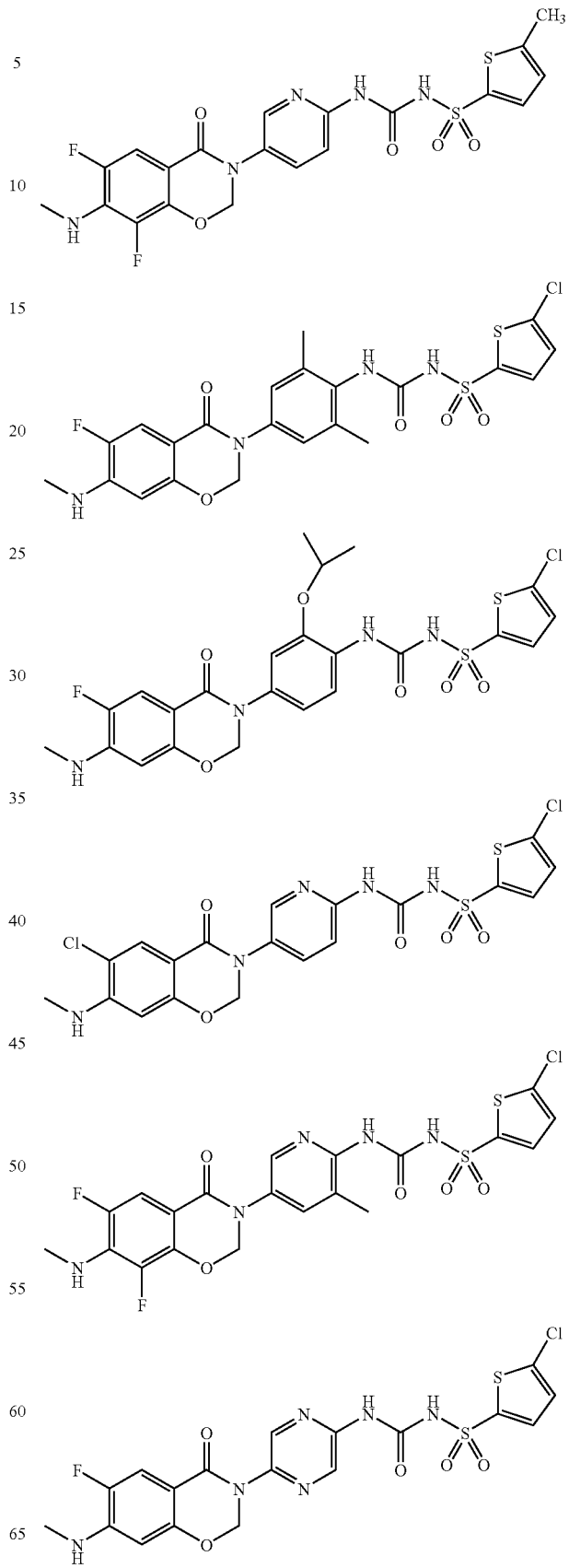

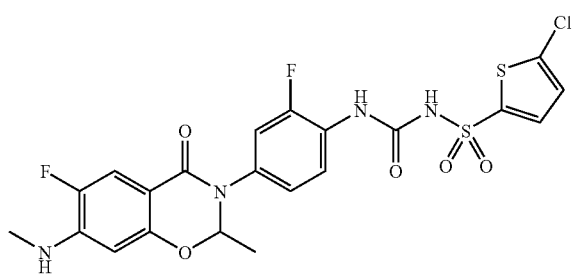
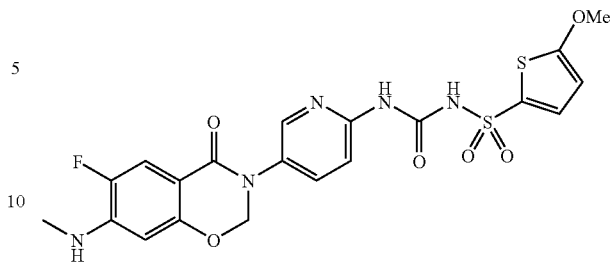
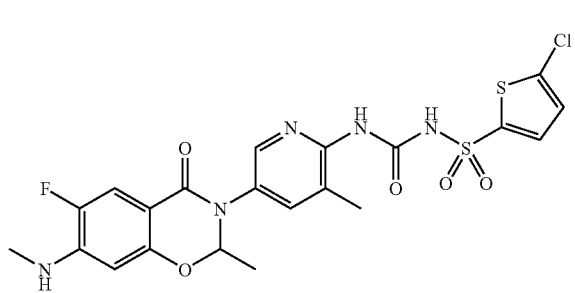
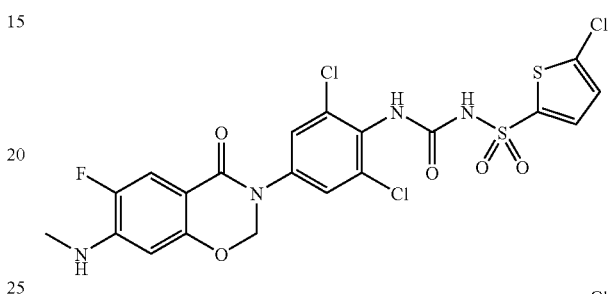
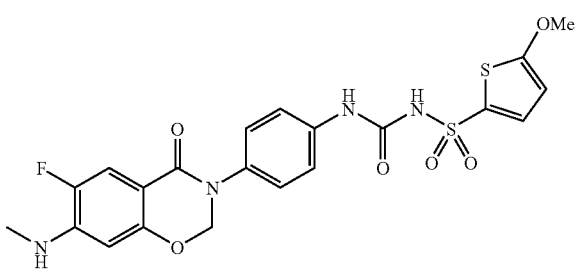
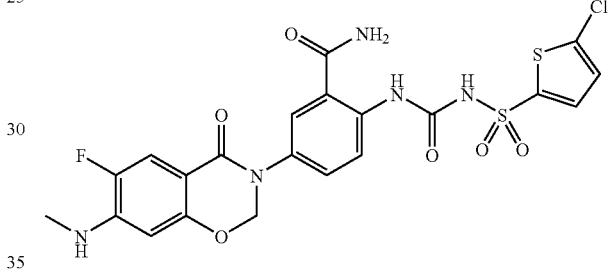
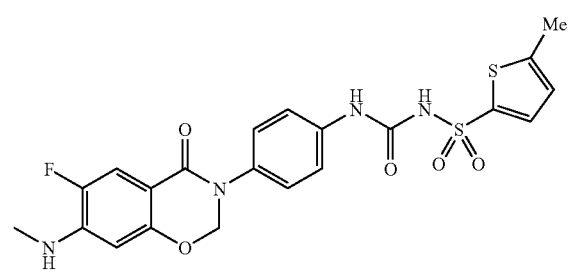
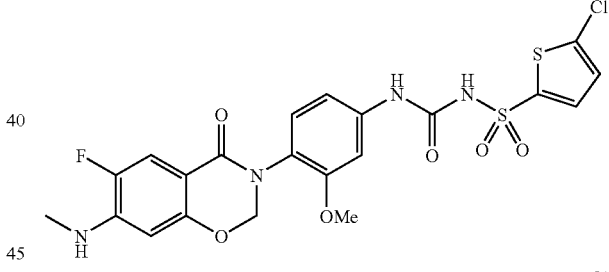
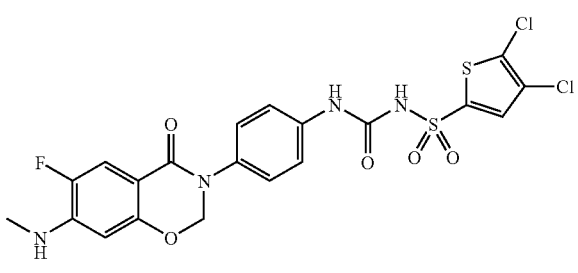
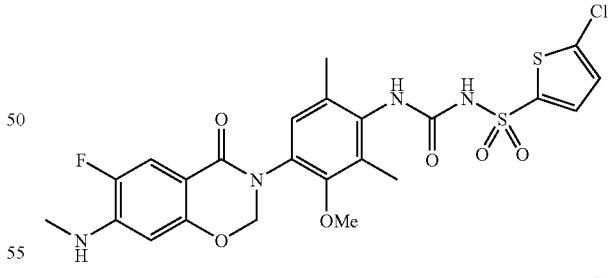
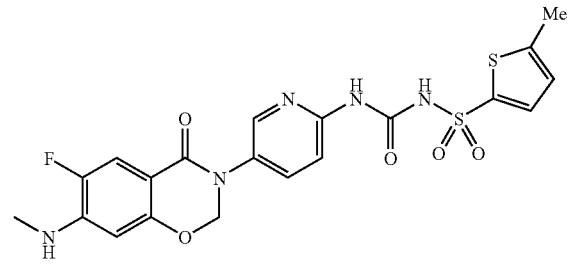
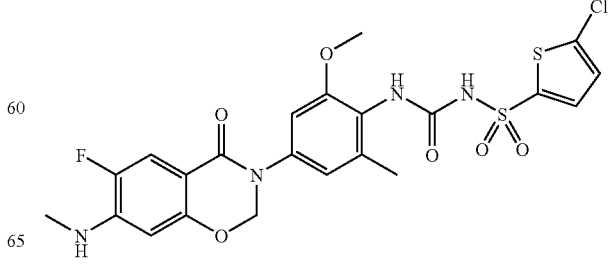

-continued

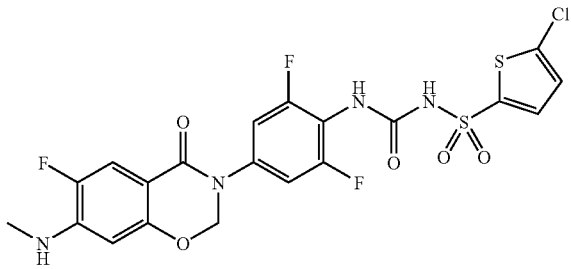

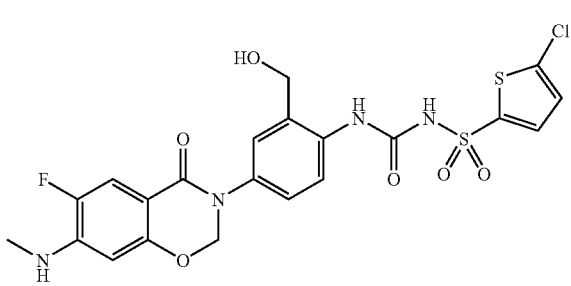

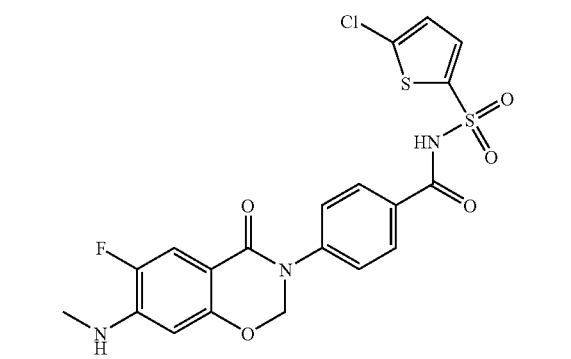

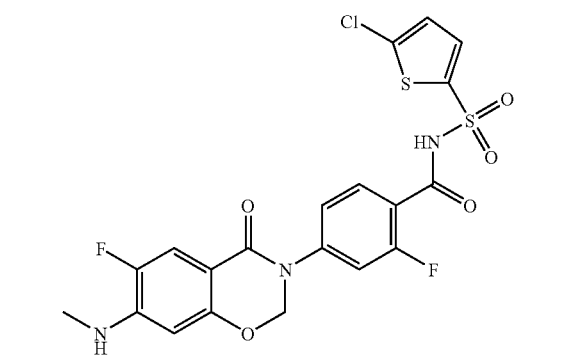

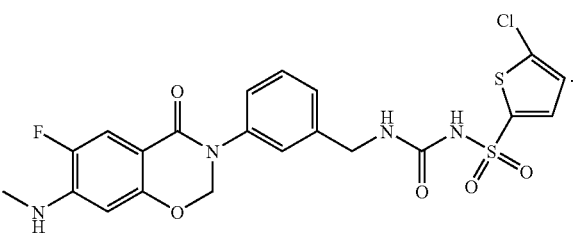

17. A method of treating a thrombosis by inhibiting a platelet ADP receptor in a subject comprising administering to a subject in need thereof, a therapeutically effective amount of a compound having the formula:

wherein
$R^1$ is a member selected from the group consisting of $C_{1-6}$ alkyl, $C_{1-6}$ haloalkyl, $C_{3-5}$ cycloalkyl, $C_{3-5}$ cycloalkyl-alkyl, benzyl, and substituted benzyl;

$R^2$ is a member selected from the group consisting of H, and $C_{1-6}$ alkyl;

$R^3$ is a member selected from the group consisting of H, $C_{1-6}$ alky $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, halogen, cyano and $-C(O)R^{3a}$, wherein $R^{3a}$ is a member selected from the group consisting of H, hydroxy, $C_{1-6}$ alkyl, $C_{1-6}$ alkoxy, amino, $C_{1-6}$ alkylamino and di-$C_{1-6}$ alkylamino;

$R^4$ is a member selected from the group consisting of H and $C_{1-6}$ alkyl;

$R^5$ is a member selected from the group consisting of H, $C_{1-6}$ alkyl, $C_{1-6}$ haloalkyl, benzyl, aryl, $C_{1-6}$ alkyl-N—$(R^{5a})_2$; $C_{1-6}$ alkyl-O—$(R^{5a})$; wherein each $R^{5a}$ is a member independently selected from the group consisting of H, $C_{1-6}$ alkyl, and optionally, two $R^{5a}$ groups attached to nitrogen are combined with the nitrogen atom to form an azetidine, pyrrolidine, piperidine or morpholine ring;

Ar is an aromatic ring selected from the group consisting of benzene, pyridine, pyrazine and pyrimidine, each of which is optionally substituted with from 1–2 $R^6$ substituents, wherein each $R^6$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl-alkoxy, amino, $C_{1-6}$ alkylamino, di-$C_{1-6}$ alkylamino, $-C(=NR^{6a})-N(R^{6b})_2$, $-C(O)R^{6a}$, $-O(CH_2)_m OR^{6b}$, $-(CH_2)_m OR^{6b}$, $-O(CH_2)_m N(R^{6b})_2$ and $-(CH_2)_m N(R^{6b})_2$, wherein each subscript m is independently an integer of from 1 to 3, each $R^{6a}$ is a member independently selected from the group consisting of H, hydroxy, $C_{1-6}$ alkyl, $C_{1-6}$ alkoxy, amino, $C_{1-6}$ alkylamino and di-$C_{1-6}$ alkylamino, and each $R^{6b}$ is a member independently selected from the group consisting of H, $C_{1-4}$ alkyl and $C_{1-4}$ alkanoyl, and optionally, two $R^{6b}$ groups attached to nitrogen are combined with the nitrogen atom to form an azetidine, pyrrolidine, piperidine or morpholine ring;

L is a linking group selected from the group consisting of a bond and —NH—; and $R^7$ is a member selected from the group consisting of H, halogen, cyano, $C_{1-6}$ alkyl, $C_{2-6}$ alkenyl, $C_{2-6}$ alkynyl, $C_{1-6}$ alkoxy and $C_{1-6}$ haloalkyl; or a pharmaceutically acceptable salt thereof.

18. A method in accordance with claim 17, wherein said compound is administered in combination with a second therapeutic agent selected from the group consisting of antiplatelet compounds, anticoagulants, fibrinolytics, anti-inflammatory compounds, cholesterol-lowering agents, blood pressure-lowering agents and serotonin blockers.

19. A method in accordance with claim 18, wherein said second therapeutic agent is an antiplatelet compound selected from the group consisting of GPIIB-IIIa antagonists, aspirin, phosphodiesterase III inhibitors and thromboxane A2 receptor antagonists.

20. A method in accordance with claim 18, wherein said second therapeutic agent is an anticoagulant selected from the group consisting of thrombin inhibitors, coumadin, heparin and enoxaparin sodium injection.

21. A method in accordance with claim 18, wherein said second therapeutic agent is an anti-inflammatory compound selected from the group consisting of non-steroidal anti-inflammatory agents, cyclooxygenase-2 inhibitors and rheumatoid arthritis agents.

22. A method in accordance with claim 18, wherein said compound is administered orally or intravenously.

23. A method in accordance with claim 17, wherein said compound has a formula selected from the group consisting of:

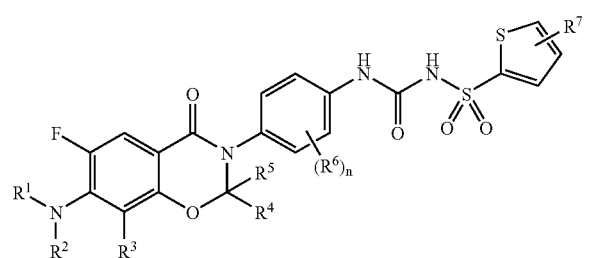

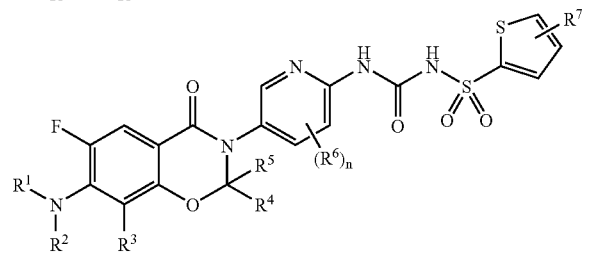

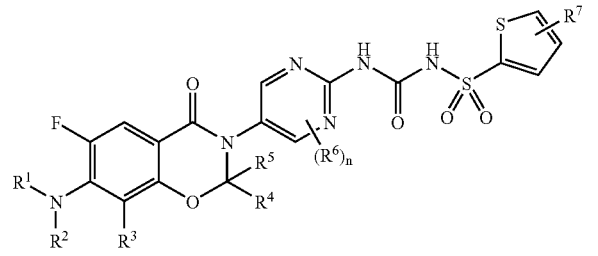

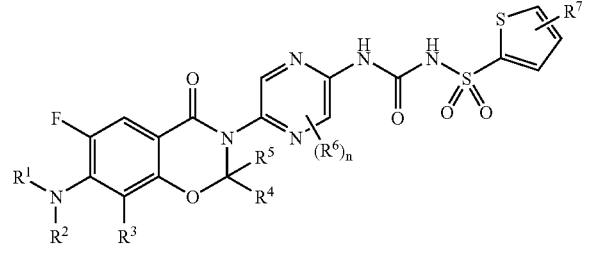

-continued

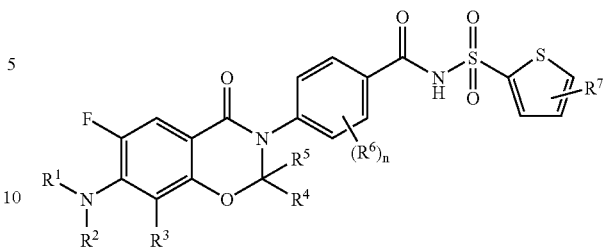

wherein subscript n is from 0 to 2.

24. A method in accordance with claim 23, wherein n is 0 or 1; $R^1$ is $C_{1-4}$ alkyl, $C_{3-5}$ cycloalkyl, $C_{3-5}$ cycloalkyl-alkyl, or halosubstituted benzyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is H or $C_{1-4}$ alkyl, $C_{1-4}$ haloalkyl, —CN, —C≡CH or —CONH$_2$; $R^6$, when present is selected from the group consisting of halogen, $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl; $R^7$ is H, $C_{1-4}$ alkyl or halogen.

25. A method in accordance with claim 24, wherein $R^1$ is $C_{1-4}$ alkyl; $R^4$ is H or CH$_3$; $R^5$ is H or CH$_3$; $R^6$, when present is selected from the group consisting of halogen, $C_{1-4}$ alkyl, $C_{1-4}$ alkoxy; $R^7$ is halogen or $C_{1-4}$ alkyl.

26. A method in accordance with claim 25, wherein $R^1$ is methyl; $R^4$ is H; $R^5$ is H or CH$_3$; $R^7$ is chloro, and is attached at the 5-position of the thienyl ring; n is 0 or 1, and $R^6$ when present is selected from the group consisting of halogen, $C_{1-4}$ alkyl, —OCH$_2$CH$_2$OH, —OCH$_2$CH$_2$OCH$_3$, —OCH$_2$OCH$_3$, —OCH$_2$CH$_2$OC(O)CH$_3$ and —O(CH$_2$)$_2$N(CH$_3$)$_2$.

27. A method in accordance with claim 17, wherein said compound is selected from the group consisting of:

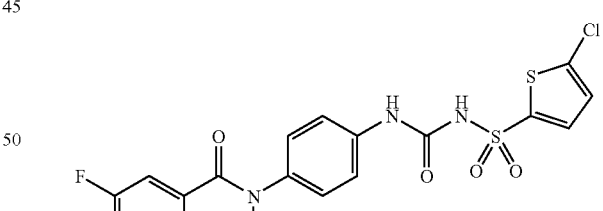

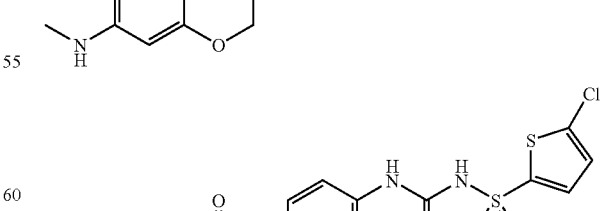

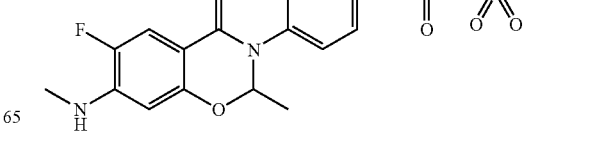

75
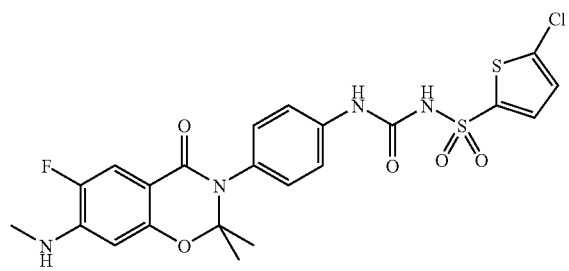
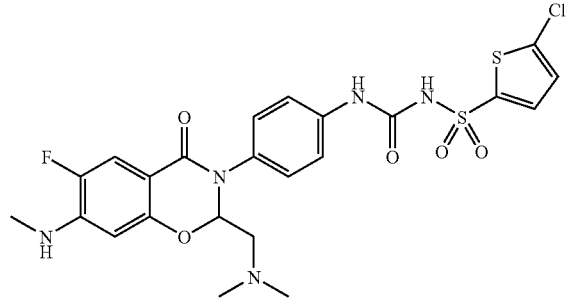
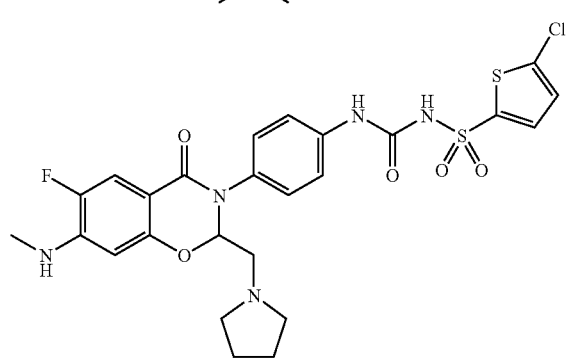
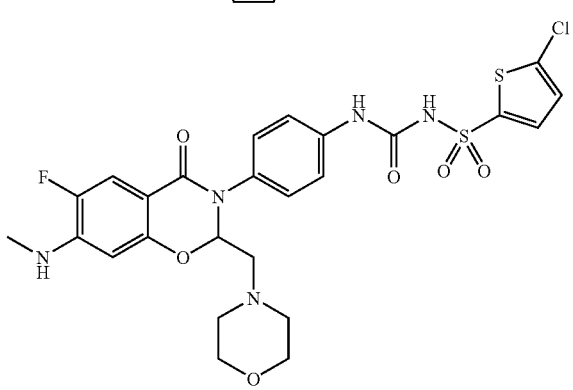
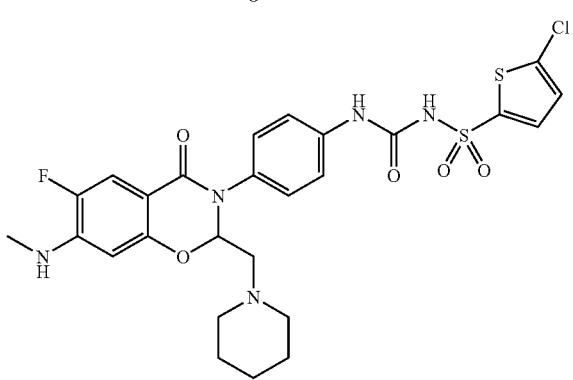
76
-continued
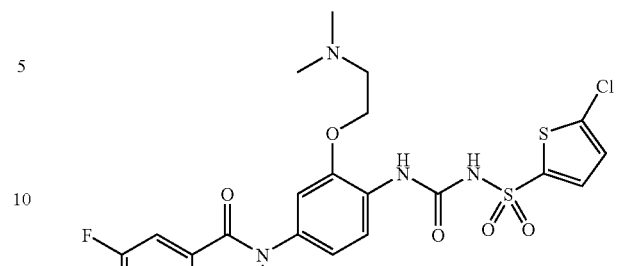
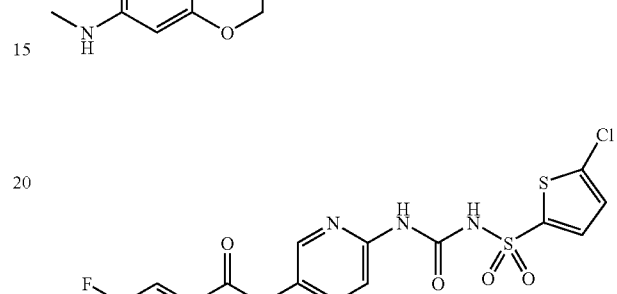
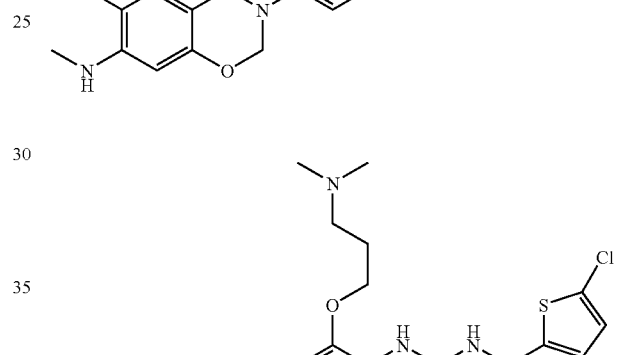
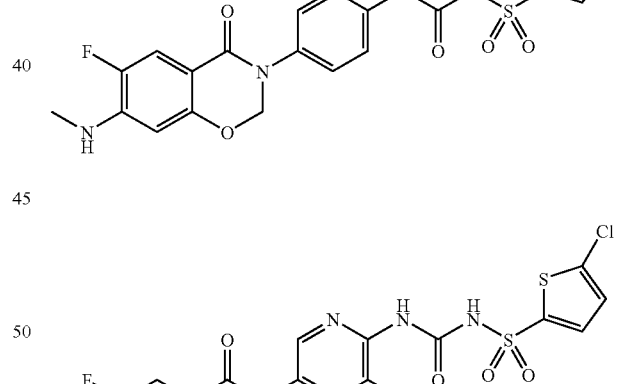
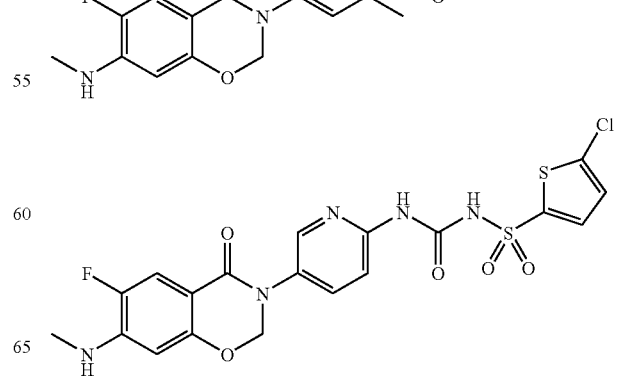

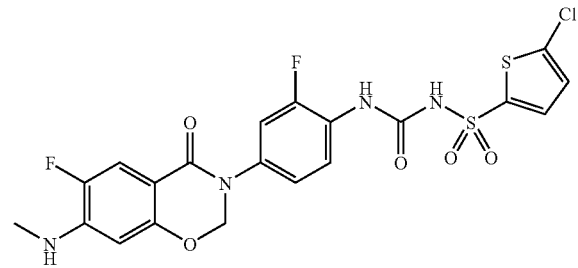
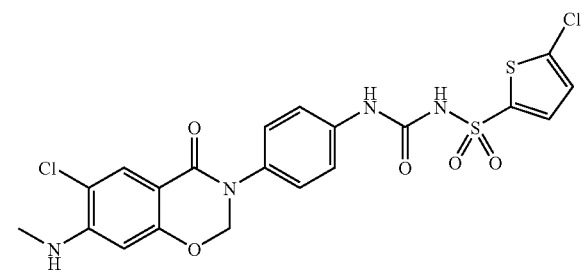
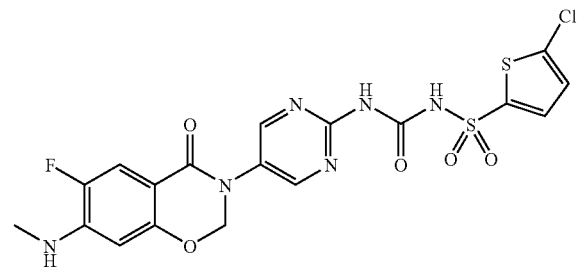
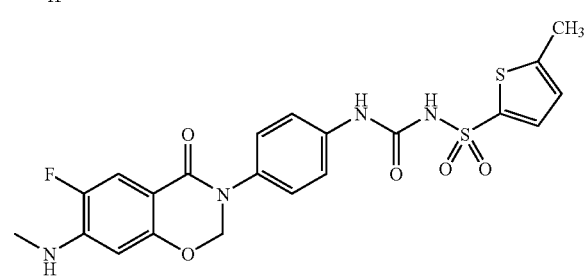
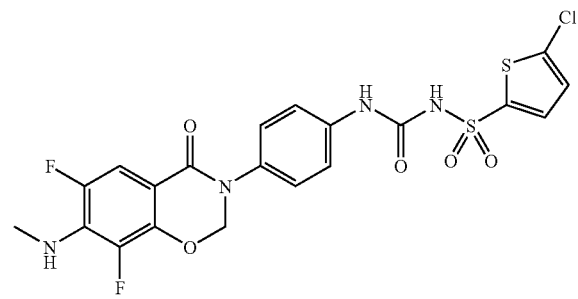
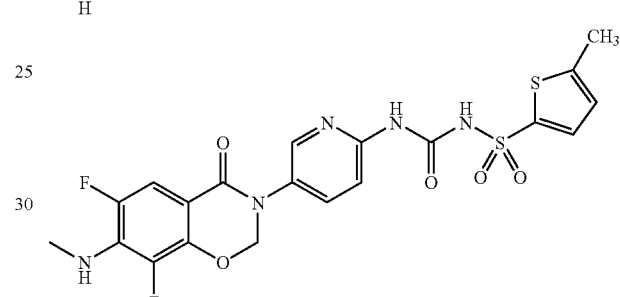
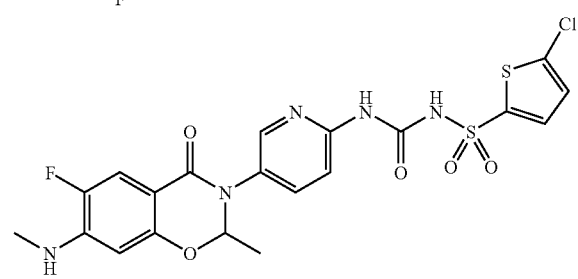
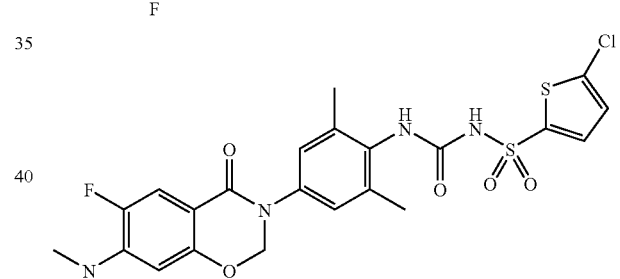
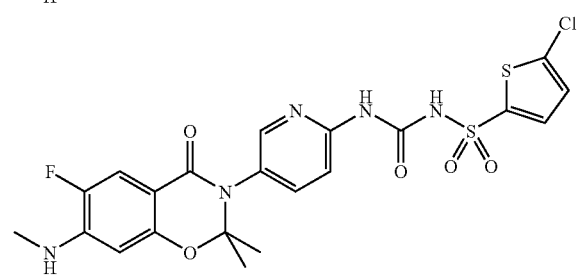
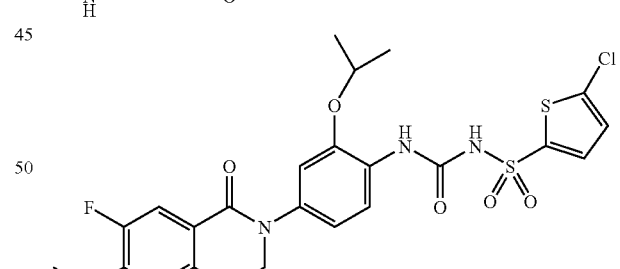
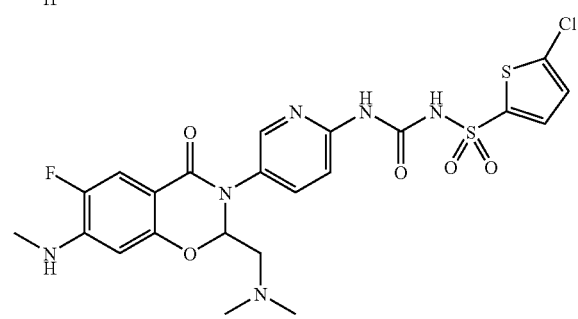
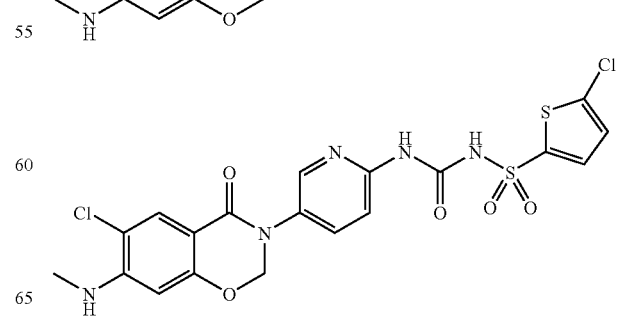

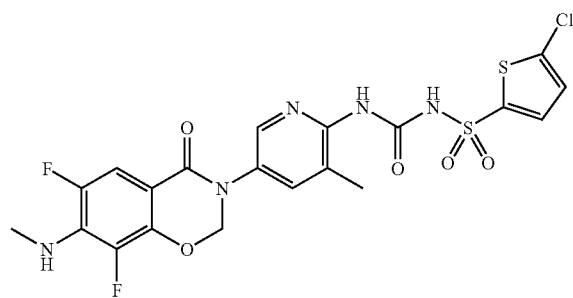
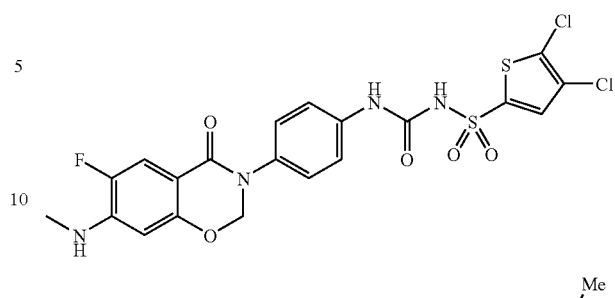
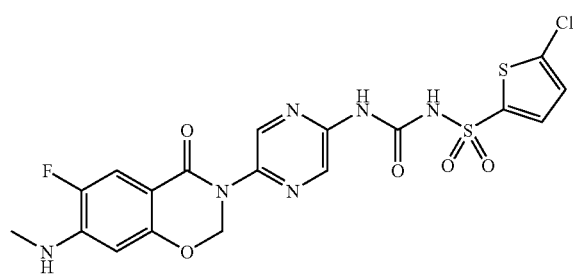
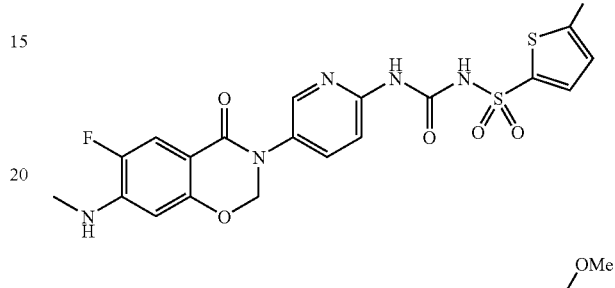
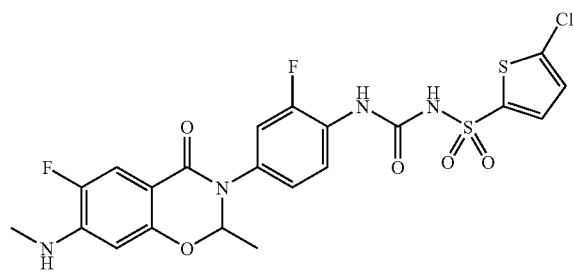
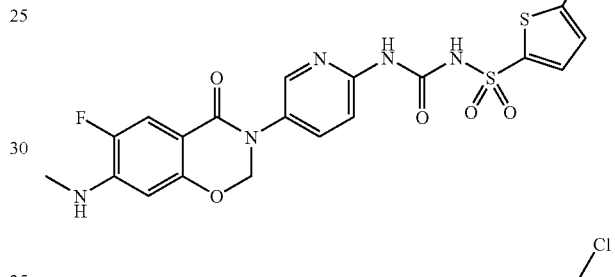
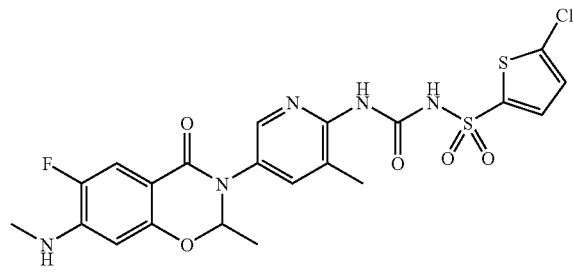
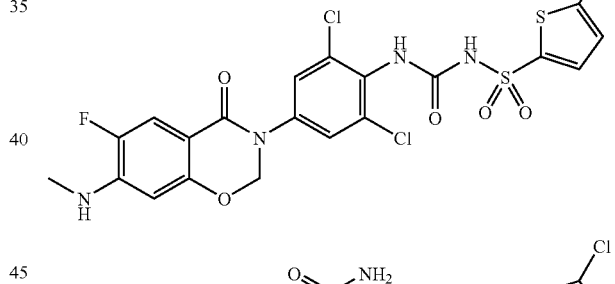
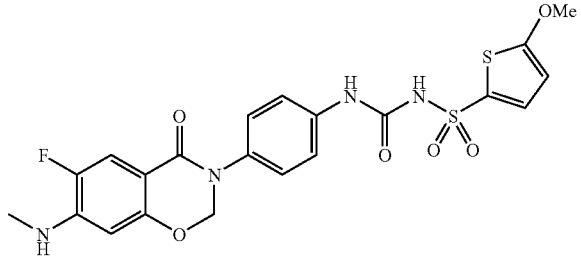
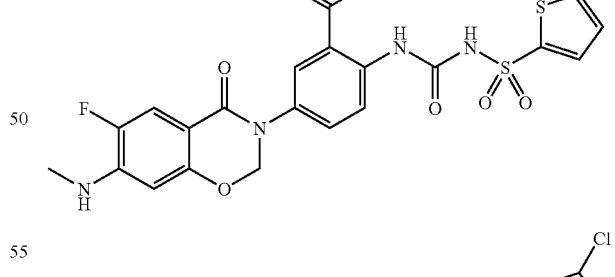
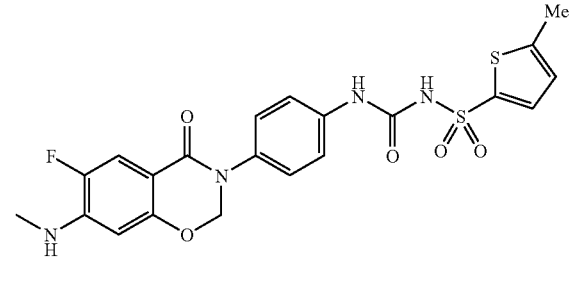

-continued
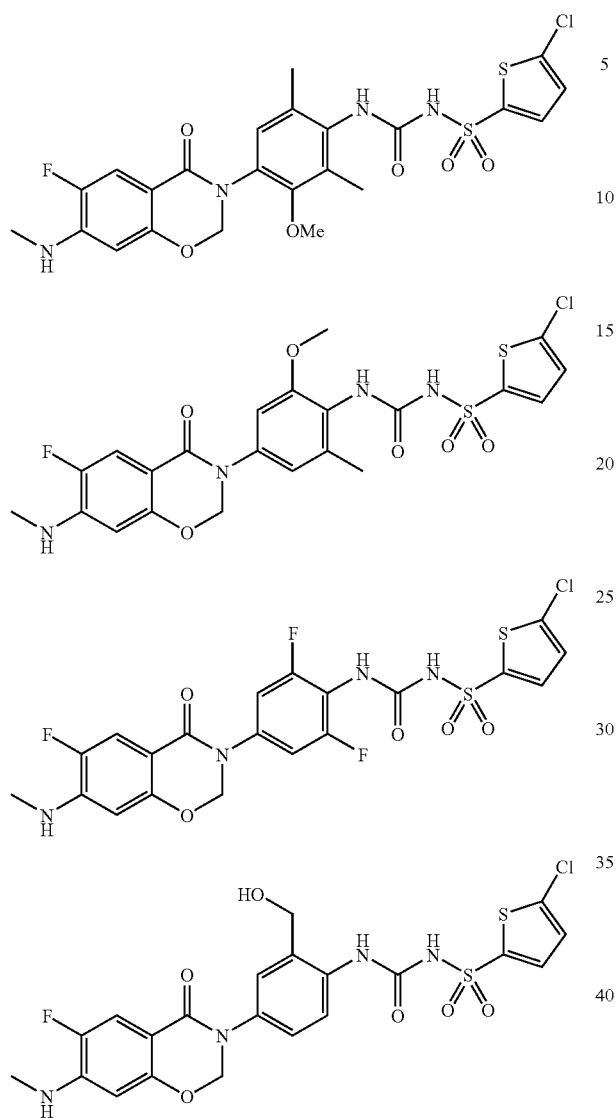
-continued
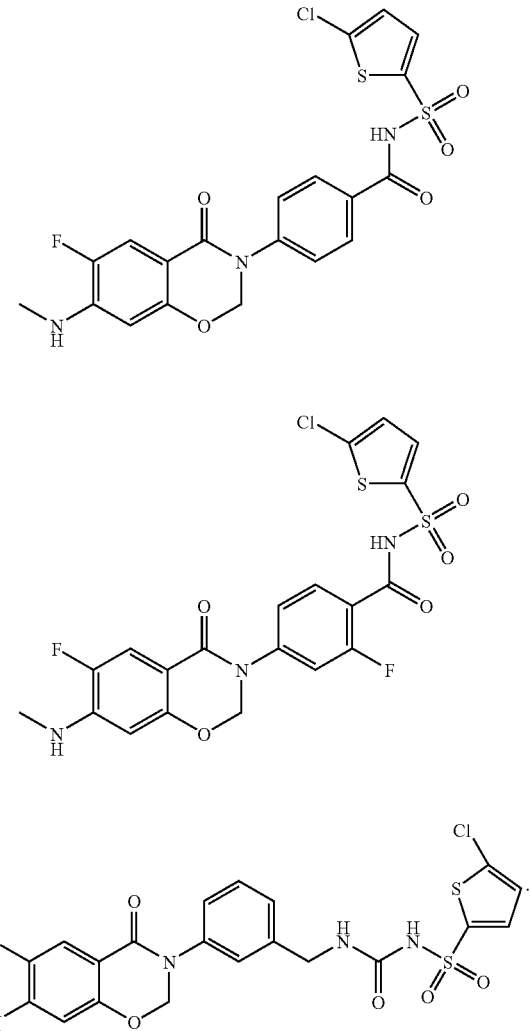
* * * * *

UNITED STATES PATENT AND TRADEMARK OFFICE
CERTIFICATE OF CORRECTION

PATENT NO. : 7,205,296 B2
APPLICATION NO. : 11/236051
DATED : April 17, 2007
INVENTOR(S) : Scarborough et al.

It is certified that error appears in the above-identified patent and that said Letters Patent is hereby corrected as shown below:

In the Claims:

Claim 1, Column 51, Lines 40-50, please delete the compound formula

"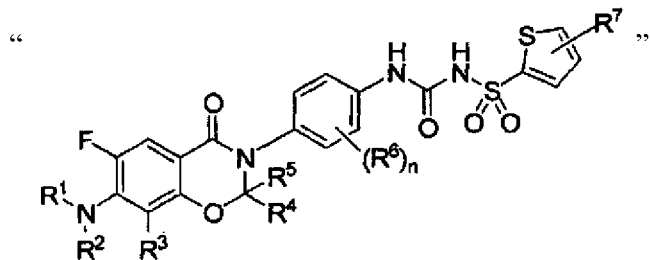"

and replace with the following compound formula

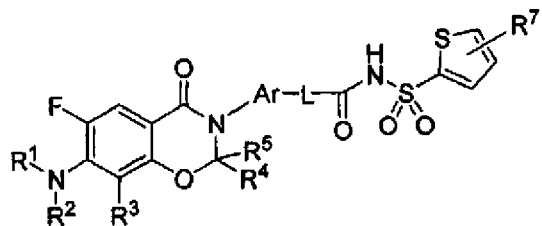

Claim 2, Column 52, Lines 40-50, please delete the compound formula

"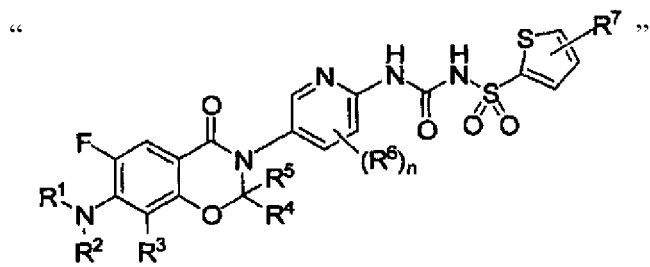"

UNITED STATES PATENT AND TRADEMARK OFFICE
CERTIFICATE OF CORRECTION

PATENT NO. : 7,205,296 B2
APPLICATION NO. : 11/236051
DATED : April 17, 2007
INVENTOR(S) : Scarborough et al.

It is certified that error appears in the above-identified patent and that said Letters Patent is hereby corrected as shown below:

and replace with the following compound formula

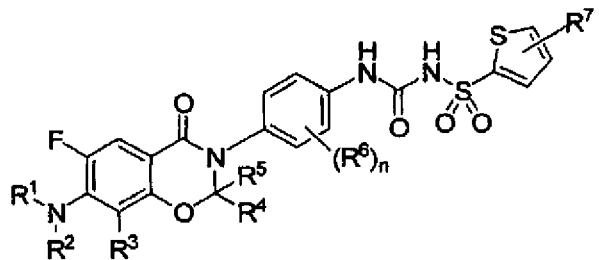

Claim 5, Column 53, Lines 20-30, please delete the compound formula

"
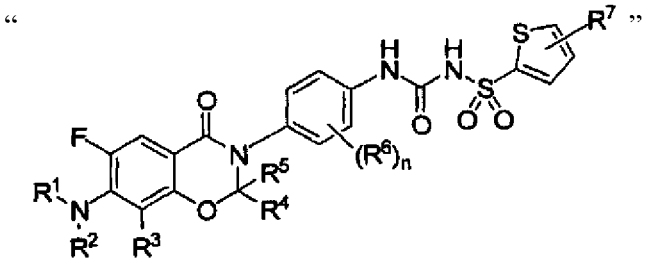
"

UNITED STATES PATENT AND TRADEMARK OFFICE
CERTIFICATE OF CORRECTION

PATENT NO.       : 7,205,296 B2
APPLICATION NO.  : 11/236051
DATED            : April 17, 2007
INVENTOR(S)      : Scarborough et al.

It is certified that error appears in the above-identified patent and that said Letters Patent is hereby corrected as shown below:

and replace with the following compound formula

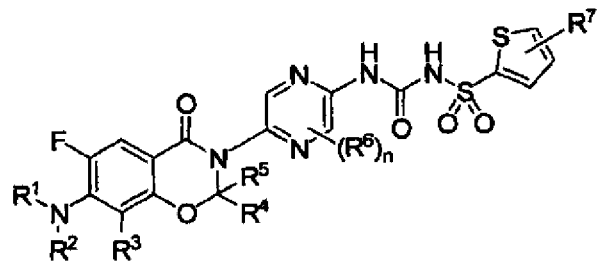

Signed and Sealed this

Eighth Day of December, 2009

David J. Kappos
*Director of the United States Patent and Trademark Office*